United States Patent
Opekun, Jr.

(10) Patent No.: US 11,690,392 B2
(45) Date of Patent: Jul. 4, 2023

(54) DEVELOPMENT OF AMYLOGLUCOSIDASE AS A MEDICINAL FOOD OR DIETARY SUPPLEMENT

(71) Applicant: Baylor College of Medicine, Houston, TX (US)

(72) Inventor: Antone Robert Opekun, Jr., Houston, TX (US)

(73) Assignee: Baylor College of Medicine, Houston, TX (US)

( * ) Notice: Subject to any disclaimer, the term of this patent is extended or adjusted under 35 U.S.C. 154(b) by 157 days.

(21) Appl. No.: 17/048,055

(22) PCT Filed: Apr. 17, 2019

(86) PCT No.: PCT/US2019/027925
§ 371 (c)(1),
(2) Date: Oct. 15, 2020

(87) PCT Pub. No.: WO2019/204486
PCT Pub. Date: Oct. 24, 2019

(65) Prior Publication Data
US 2021/0145035 A1 May 20, 2021

Related U.S. Application Data

(60) Provisional application No. 62/659,459, filed on Apr. 18, 2018.

(51) Int. Cl.
*A23L 29/00* (2016.01)
*A23L 33/00* (2016.01)
*A61K 38/47* (2006.01)

(52) U.S. Cl.
CPC .............. *A23L 29/06* (2016.08); *A23L 33/30* (2016.08); *A61K 38/47* (2013.01); *C12Y 302/01003* (2013.01)

(58) Field of Classification Search
CPC .......... A23L 29/06; A23L 33/30; A23L 33/10; A61K 38/47; C12Y 302/01003; C12N 9/242; A23V 2002/00; A61P 1/00; A61P 1/14
See application file for complete search history.

(56) References Cited

U.S. PATENT DOCUMENTS

| | | |
|---|---|---|
| 3,335,066 A | 8/1967 | Corman |
| 2009/0035293 A1 | 2/2009 | Svendsen et al. |
| 2016/0114012 A1 | 4/2016 | Farnum |
| 2017/0319668 A1 | 11/2017 | Wyrobnik et al. |

OTHER PUBLICATIONS

Global Healing, The health Benefits of Glucoamylase, Written by Dr. Group, DC Founder, 2014, 5 pages of PDF, retrieved from explore.globalhealing.com.*
Money et al: "Review: Management of Postprandial Diarrhea Syndrome", American Journal of Medicine, vol. 125, No. 6, Jun. 2012 (Jun. 2012), pp. 538-544.
Ismail et al. "Aflatoxin in foodstuffs: Occurrence and recent advances in decontamination" Food Research International, vol. 113 (Jun. 30, 2018): pp. 74-85.
Koc et al. "Purification and characterization of a thermostable glucoamylase produced by Aspergillus flavus HBF34" African Journal of Biotechnology, vol. 9 Issue 23 (Jun. 7, 2010): pp. 3414-3424.
Negi et al. "Extraction and Purification of Glucoamylase and Protease Produced by Aspergillus awamori in a Single-Stage Fermentation" Food Technology and Biotechnology, vol. 49 Issue 3 (2011 ): pp. 310-315.
Reddy et al. "Mycotoxigenic Fungi, Mycotoxins, and Management of Rice Grains" Toxin Reviews, vol. 27 Issue 3-4 (Dec. 2, 2008).
George F. Longstreth, et al; "Functional Bowel Disorders"; The American Gastroenterological Association Insistute: 2006; 130:1480-1491.
N.J. Talley, et al; "Functional Gastronduodenal Disorders"; Gut 1999;45 (Suppl II) 1137-1142; Sep. 1, 1999.

* cited by examiner

*Primary Examiner* — Kade Ariani
(74) *Attorney, Agent, or Firm* — Norton Rose Fulbright US LLP

(57) ABSTRACT

Embodiments of the disclosure include particular amyloglucosidase (AMG) compositions formulated as a nutriceutical or medicinal food, for example. The AMG compositions are formulated at a specific dosage and/or are lacking in one or more toxins or have substantially reduced levels of toxin, such as deoxynivalenol (vomit toxin). The AMG compositions are provided to individuals in need thereof, such as an individual with or at risk for congenital sucrase isomaltase syndrome, functional bowel disorders, small bowel bacterial overgrowth, protein-calorie malnutrition (marasmus), radiochemotherapy-induced mucositis and/or short-gut syndrome.

14 Claims, 18 Drawing Sheets

AMG/Rice Activity

Glucose concentration in mg/dL vs Time in minutes

— AMG Suspension
— AMG Capsule

Data: Don-V toxin NEGATIVE

A) For 1 ml AMG suspension:

Δ Glucose increase at 1 minute =+ 84.9 mg/dL
Δ Glucose increase at 2.5 minutes =+ 89.7 mg/dL
Δ Glucose increase at 5 minutes =+ 123 mg/dL
Δ Glucose increase at 10 minutes =+ 143 mg/dL B) For 1 AMG Capsule:

Δ Glucose increase at 1 minute =+ 48.5 mg/dL
Δ Glucose increase at 2.5 minutes =+ 69.9 mg/dL
Δ Glucose increase at 5 minutes =+ 78.7 mg/dL
Δ Glucose increase at 10 minutes =+ 81.6 mg/dL

FIG. 10

AMG/Maize Activity

[Graph: Glucose concentration in mg/dL vs Time in minutes, showing AMG Suspension (♦) and AMG Capsule (■)]

Data: Don-V toxin NEGATIVE

A) For 1 ml AMG suspension:
Δ Glucose increase at 1 minute =+ 227.4 mg/dL
Δ Glucose increase at 5 minutes =+ 510.3 mg/dL
Δ Glucose increase at 10 minutes =+ 530.9 mg/dL B) For 1 AMG Capsule:
Δ Glucose increase at 1 minute =+ 136.9 mg/dL
Δ Glucose increase at 5 minutes =+ 307.7 mg/dL
Δ Glucose increase at 5 minutes =+ 383.3 mg/dL

FIG. 12

DEVELOPMENT OF AMYLOGLUCOSIDASE AS A MEDICINAL FOOD OR DIETARY SUPPLEMENT

This application is a national phase application under 35 U.S.C. § 371 that claims priority to International Application No. PCT/US2019/027925 filed Apr. 17, 2019, which claims priority to U.S. Provisional Patent Application Ser. No. 62/659,459, filed Apr. 18, 2018, both of which are incorporated by reference herein in their entirety.

TECHNICAL FIELD

Embodiments of the present disclosure concern at least the fields of cell biology, nutrition, biochemistry, molecular biology, gastroenterology, endocrinology, and medicine.

BACKGROUND

In health, the intestinal mucosal cells function to absorb monosaccharides from hydrolyzed complex dietary carbohydrates and, when damaged, are significantly impaired from completely hydrolyzing oligosaccharides during an illness that often results with chronic diarrhea. The mucosal cells are dynamic and assimilate the luminal digestive products and transfer nutrients to various endogenous metabolic processes (Ravich and Bayless, 1983). At the earliest level, food digestion critically depends upon secretion of salivary and pancreatic α-amylase and cellular expression of several other apical digestive enzymes. First, dietary starch is 'coarsely' hydrolyzed in the duodenum and jejunum, by intraluminal pancreatic alpha-amylase to release soluble maltotriose, oligosaccharides and alpha-limit dextrins (oligomers). These intermediate by-products of partial digestion are not directly absorbable and must undergo further enzymatic hydrolysis (cleavage) at the apical enterocyte surface to monosaccharides (glucose, fructose, and galactose) by expressed a cadre of disaccharidases including sucrase-isomaltase (SI), maltase-glucoamylase (MGAM), and lactase. These enzymes, along with trehalase (a minor player), are continuously produced by healthy luminal enterocytes that constitute the apical mucosal surface, also referred to as the brush border because of the exposed velveteen-appearing microvilli. Released monosaccharides, mostly free glucose, enter the absorbing enterocyte at the apical surface by specific transport mechanisms ("carriers") and are distributed to the body and inhibit hepatic gluconeogenesis. It is well known that mucosal enzyme activity is frequently reduced in states of malnutrition (Mehra et al., 1994) and mucosal injury. Except for lactase and sucrase, this mucosal-level enzyme insufficiency that completes starch and fructan hydrolysis (maltase and isomaltase) is a largely unaddressed clinical and therapeutic concern.

The complete digestion of starch is thought to be predominantly reliant on the proper expression and function of the sucrase-isomaltase (SI) enzyme complex (Auricchio et al., 1963). The SI is a complex composed of two [alpha]-glucosidase units, sucrase, and isomaltase (Conklin et al., 1975). The isomaltase component demonstrates considerable [alpha]-glycosidic activity on starch-derived glucose oligomers, and the SI complex together contributes to 60 to 80 percent of total intestinal maltase activity (Gericke et al., 2016). The isomaltase component of the SI complex hydrolyzes [alpha]-1,6 linkages of the [alpha]-limit dextrins after primary luminal pancreatic amylase has reduced the ingested starch to soluble subunits (Galand, 1989). Generally, mucosal maltase-glucoamylase (MGAM) is relatively restricted to hydrolyze alpha 1-4 bonds of soluble oligosaccharides and together with the SI component works to hydrolyze alpha 1-6 bonds and complete starch digestion to glucose with some cross activity between enzymes (Diaz-Sotomayor et al., 2013). MGAM is noted to have a significant amount of compositional amino acid sequence homology that appears responsible for some evolutionary redundancy for survival. Congenital mucosal enzyme deficiency syndromes have been reported due to primary gene mutations (Geng et al., 2014) and secondary transport errors (Jacob et al., 2000).

In western societies, where dairy products remain part of the habitual diet, adult-type hypolactasia presents a challenge to those unwilling to refrain from non-fermented/cured products containing lactose. Symptoms of gastrointestinal distress, identical to those described above, may be mitigated by a nutritional enzyme supplement, called LACTAID® that contains the microbial-produced enzyme lactase-phlorizin hydrolase. The oral supplement is typically a gel-capsule containing microbial produced lactase (~9000 LU/capsule) and is a model approach to alleviating symptoms of other digestive enzyme insufficiency syndromes. Two ubiquitous, GRAS-listed, filamentous fungi, *Aspergillus oryzae* and *Aspergillus niger*, or recombinant yeast organisms are used to commercially produce lactase for human dietary supplementation without objection from the US Food & Drug Administration.

In a manner similar; a yeast-derived enzyme product, sacrosidase, has been put forth to aid in the digestion of sucrose (Puntis and Zamvar, 2015), but it has virtually no starch or fructan hydrolyzing activity (Kasperowicz et al., 2012). The utility of sacrosidase is adjunctive since it is often easier to restrict dietary sucrose, but a similar approach cannot be applied to dietary starch maldigestion because dietary starch is a human staple. Recombinant human SI and MGAM are not widely available, and stability has not yet been determined, so other exogenous alternatives are needed clinically to aid faulty starch digestion when symptomatic problems occur.

Enteritis is a dysfunctional state in which destruction of the gastrointestinal epithelial mucosa (small intestine) occurs with the resultant loss of digestive enzyme expression with severe symptoms, and this typically occurs as a consequence of enteric infection, such as rotavirus (Langman and Rowland, 1990). The mucosal cells of the small bowel are highly metabolic, are known to turn over rapidly and are particularly vulnerable to the toxic effects of viruses, parasites, and to some medications used to treat infections and malignancies. Mucosal surface enterocytes are not the only primary digestive agents but are a primary line of defense against gastrointestinal infections, such a secondary cryptosporidiosis or giardiasis. In a manner of speaking, enterocytes take the first hit. In addition to various infections, interruption of mucosal digestive processes by toxins, and protein-calorie malnutrition can further impact normal digestive processes and predispose to protracted disease (Custodio et al., 2000; Hlaysa et al., 2016). For example, HIV infection is a major predisposing factor leading to secondary infections and resultant wasting and secondary intestinal disaccharidase deficiency (Taylor et al., 2000). Enzyme deficiency may idiopathically occur in the absence of visible mucosa injury. Enzyme inhibition by binding (e.g., acarbose) (Singla et al., 2016), and substrate mimicry (Bompard-Giolles et al., 1996), also interferes with starch hydrolysis and may cause significant morbidity due to food maldigestion.

The use of combination radiochemotherapy for the management of rectal cancer, pancreatic adenocarcinoma (Wang-Gillam et al., 2013), and other abdominal tumors (Mundt et al., 1999) is known to produce predictable adverse side effects such as mucositis-associated diarrhea. Enterocyte damage appears to worsen in severity with the type of oncotherapy (Reis et al., 2015). The high rate of gastrointestinal mucosal cellular replication affords the mucosa a particular-susceptibility to this type of cytotoxicity. The condition is similar, but often greater severity than infectious enteritis, and reflects another unmet clinical need to aid or replace digestive enzyme activities at the mucosal surface level. Like infectious enteritis, mucositis is characterized by reduced proliferation of epithelial cells in the intestinal crypts and villous atrophy, which results in a loss of absorptive capacities (Keefe et al., 2000). Recovery is variable and appears dependent upon multiple factors inherent to the primary disease in addition to inadequate nutrient digestion and absorption.

Mucositis may be very severe in patients who receive aggressive myeloablative chemotherapy and for some aggressive gastrointestinal and pelvic malignancies. It is a significant problem that affects approximately one-third of patients treated with adjunctive pelvic radiochemotherapy for rectal cancer which often prompts a modification in primary treatment (Roh et al., 2009). Mucositis predisposes to supra-infections (Honda et al., 2010). During the time of malignant proliferation or infectious insult, glucose and other nutrients needed for cell expansion are derived, in-part, from accelerated apoptosis of healthy cells and breakdown of lean body mass to capture recycled nutrients (cannibalistic wasting secondary to inflammatory processes) (Fearon et al., 2011). In summary, malignancy inherently creates an energy deficit (cachexia), immune suppression and mucositis impairs absorption of nutrients including glucose derived from dextrin and oligosaccharides to compound the scene. In health, the small intestinal glucose transporter is efficient (Wright et al., 2011) and in disease is among the first apical surface turnover proteins to be expressed in recovery (Klish et al., 1980) and appears to precede expression of mucosal enzymes and deserving of exploitation. It appears that specific adjunctive digestive enzyme therapy that releases glucose from starch-derived oligosaccharides could be beneficial toward restoring positive energy balance, and demand for this type of therapy would be great.

The loss of small bowel enterocytes decreases the availability of mucosal bound and mucosal secreted digestive enzymes and results in maldigestion of food substrates that ultimately leads to excessive colonic fermentation of unabsorbed nutrients, including startch, and resultant manifested symptoms include bloating, pain, fatigue, and diarrhea (Stringer et al., 2007). These distal events may be associated with loss of structural collagen and macroscopic ulcerations with bleeding and loss of iron stores. Furthermore, the onset of diarrhea can further alter dietary patterns, lead to dehydration, electrolyte imbalance, and lead to perirectal skin breakdown, local pain, and cellulitis (Peterson et al., 2011). As such, enteritis and mucositis are significant clinical problems because the effects predispose the patient to comorbidities including malnutrition, anemia and additional opportunistic infection (Andreyev et al., 2014). With these comorbidities comes further net loss of mucosal enzyme expression to compound the disease process.

The features of enteritis are similar to those of irritable bowel syndrome, parasitic enteritis, small bowel bacterial overgrowth, or runner's diarrhea (de Oliveira et al., 2017) and associated with less morbidity. Symptoms may include abdominal pain, bloating, changes in stool patterns and variable central nervous system disturbance (e.g. headaches), and the symptoms may be incapacitating (Marteau and Flourie, 2001). In lieu of endoscopy, substrate-specific, tracer breath test technology may be used to identify patients that have lost enzymatic digestive functions for starch-derived oligosaccharides but these tests are not widely available, but have been optimized for use in clinical field studies (Opekun et al., 2014).

Proximal maldigestion leads to excessive distal colonic fermentation and production of fatty acids that, when absorbed, may indirectly contribute to anorexia to complicate a clinical condition (Petersen and Forsmark, 2002) and colitis. Proximal maldigestion can also lead to adverse changes in the distal colonic microbiota (Nielsen et al., 2016). The loss of mucosal integrity also contributes to inflammatory responses that further impede enterocyte recovery, including loss of the expression of nutrient transporter expression with concomitant non-passage of free luminal D-glucose (Cardani et al., 2014). Enterocyte Na—K-ATPase activity that drives co-transporters become diminished (Saha et al., 2015) and may contribute to increased vulnerability to lipopolysaccharide-induced mucosal injury and exacerbation of malabsorptive conditions. As such, it stands to reason that the availability of free D-glucose to some of the spared enterocytes, where the normal sodium glucose transporter 1 (SGLT-1) persists, would be critical to restoring mucosal health. Amelioration of the malabsorptive condition could limit further injury. Simply stated, local cells in the intestines need energy from free glucose to survive and heal, and a targeted digestive aid for starch-derived oligosaccharides should be very useful in gut rehabilitation. As such, increasing starch digestibility appears to be a sound approach to therapeutically increasing mucosal glucose availability when endogenous mucosal enzymes are insufficient and when glucose transporters remain intact or are first to recover.

Treatment of enteritis, a primary cause of carbohydrate intolerance, mainly consists of controlling symptoms by inhibiting motility and secretions with highly variable results (Schiller, 2017). Agents that suppress intestinal motility (e.g., loperimide) and octreotide are the mainstay-treatment that inhibits secretions, assisting with the limitation of volume depletion, but these agents do so without improving digestive capacities. At present, there is no widely accepted approach to aid digestion of dietary carbohydrate oligomers (oligosaccharides dextrins, starches). In advanced settings, elemental feeding and intravenous feeding may be implemented at great cost and iatrogenic risk. Yeast derived sacrosidase (aka: invertase) has been used to assist those with congenital sucrase deficiencies and other mucosal inflammatory conditions and is a parallel model (different substrate and different enzyme) to approach the current starch maldigestion problem (Cohen, 2016; Puntis and Zamvar, 2015). Numerous, low-dose supplements have been marketed without specific indications, activity, or purity and efficacy remains to be proven. Effective facilitation of compromised carbohydrate digestion would be expected to limit aberrant colonic fermentation and its associated osmotic and inflammatory effects, and therefore decrease diarrhea and related mucositis symptoms. Furthermore, and conversely, enhancement of digestion of nutritionally sparse starchy-grains, such as sorghum, *quinoa*, spelt, and amaranth could enhance caloric yield among the undernourished populations living in arid conditions.

This application and disclosure encompasses the embodiment that ingestion of non-toxic fungal-derived enzymes (e.g., amyloglucosidase, AMG) could significantly aid in the hydrolysis of dietary starches when delivered and dosed appropriately (CAS Number: 9032-08-0). Administration of AMG should be helpful as a nutraceutical or medical food to release glucose in the stomach or small intestine, with or without the addition of invertase (sacrosidase) (CAS Number: 9001-57-4) (del Castillo Agudo and Gozalbo, 1994). Numerous dietary supplements are marketed that contain small amounts of AMG to aid starch digestion. There is one, small double-blind clinical trial, from 1971 by Karina et al., that reported symptom improvement with the use of a crude, fungal-derived enzyme concentrate that contained AMG (Karani et al., 1971). As such, the concept of specifically using AMG to aid the complete digestion of starch has not been thoroughly pursued. Furthermore, the concept has been suggested for use in animals that ingest crude plant cell wall grains (B-glucans in barley and oats and arabinoxylans (pentosans) in rye and wheat) to improve digestibility and, to that end, weight gain (Cambell G L and Bedford M R, 1992), but not specifically nor conclusively for dietary starch contained within the kernels.

Invertase is biosynthesized by many microorganisms including yeast strains of *Saccharomyces cerevisiae* and *Saccharomyces carlsbergensis* (Para et al., 1980) and two forms of invertase exist, with and without carbohydrate moieties. It is loosely understood that sucrose-hydrolyzing enzymes, derived from plants, are called invertase because a sucrose substrate solution polarizes light in a positive direction, but after hydrolysis to fructose and glucose, the net light rotation is −20 degrees. The external form of invertase is predominant; it is a glycoprotein containing 50% mannan and 2-3% glucosamine with a molecular weight of ~260 kD. The intracellular invertase has a molecular weight of 135 kD and is relatively void of carbohydrates. It is unlikely that the addition of invertase could offer any clinically significant advantages where starch maldigestion is thought to be the main problem. It is unclear if invertase that hydrolyzes sucrose ($\alpha$-D-glucopyranosyl-(1→2)-$\beta$-D-fructofuranoside, EC 200-334-9), could, in combination, offer additional benefit as sucrose is also pervasive in the diet of western populations, but whereas sucrose is relatively void from the diet elsewhere (Wittekind and Walton, 2014). Invertase, from some sub-species of *Saccharomyces*, may have some inherent glycosidic activity for polysaccharides because it has been shown to hydrolyze inulin (Latorre-Garcia et al., 2005; Yuan and Wang, 2013), but its utility to aid in starch or dextrin hydrolysis is minimal or null. Sacrosidase activity is commonly measured as Sumner units, and this is the activity of the enzyme which, under the conditions of the assay, will convert 1 mg of sucrose to glucose and fructose in 5 minutes.

Amyloglucosidase (AMG) as a potential nutraceutic for maldigestion and malnutrition AMG is derived from non-pathogenic strains of *Aspergillus* species and *Saccharomycopsis* and, like MGAM, is inhibited by acarbose (Amirul et al., 1996; Sauer et al, 2000). AMG is expressed in vivo with a variety of other noxious organic compounds and recombinant, pure forms are not yet known to exist. AMG has a reported specific glycosidic activity that approximates 330 amyloglucosidase (glucoamylase) units (AGU) per milligram protein (Natarajan and Sierks, 1996), is robust with regard to temperature and pH activity and can be selectively precipitated from crude culture filtrate by alginate (affinity precipitation) (Teotia et al., 2001; Mahajan et al., 1983) [Foods Chemical Codex (FCC-USP) activity unit of glucoamylase activity has also been defined as the amount of glucoamylase that will liberate 0.1 μmol/min of p-nitrophenol from the PNPG Solution at pH 4.5 and 50° C. on a casein substrate] which represents hydrolysis of one maltose equivalent.

AMG hydrolyses dietary starch, oligosaccharides, dextrins, alpha-limit-dextrins, and alpha-cylodextrins. Numerous nutritional supplements have been marketed that contain trivial amounts of crude AMG, but clinical efficacy, specific to AMG, has not been previously claimed. AMG is a potent inverting exo-acting hydrolase-releasing glucose from the non-reducing ends of oligosaccharides which is used in minuscule amounts as a component of nutritional supplements and in the food industry to modify starches in vitro (Guzman-Maldonado and Paredes-Lopez, 1995). Relative rates of hydrolysis for AMG at 37° C. and pH 4.8 for some representative oligosaccharides are: (maltose: 300: maltotriose: 360; maltotetrose: 770; maltopentoses: 1000; iso-maltopentose: 23; and 6-$\alpha$-maltosylglucose: 260. AMG easily hydrolyses dietary starch, but the rates are highly variable depending upon the agricultural grain source. AMG has been shown to hydrolyse alpha-cyclodextrins, a type of dietary emulsifier may cause gastrointestinal distress and malabsorptive/fermentative diarrhea when excessively taken in (Lina et al., 2004), but the AMG-hydrolysis rates are highly variable depending upon ring size (Rather et al., 2015, Chen et al., 2017) and luminal conditions. AMG will not cleave Glu $\alpha$1-2-Fru bonds (as in sucrose) or glucan bonds in chemically-modified starch (e.g., with >1% of glucose product of polysaccharide hydrolysis is D-glucose). It is distinguished by releasing alpha-glucose from substrates having alpha-glycosidic linkages (Goncalvez et al., 1998) and is used in the final step of food analysis to determine soluble dietary fiber content from insoluble content (Nisha and Satyanarayana, 2016). The free enzyme is active in aqueous media and lipid vesicles (Li et al., 2007). Three-dimensional structures have been determined for free and inhibitor-complexed glucoamylases. The catalytic domain folds are a twisted (alpha/alpha) (6)-barrel with a central funnel-shaped active site, while the starch-binding domain folds as an antiparallel beta-barrel and has two binding sites for starch (Sauer et al., 2000).

Allergy to inhaled AMG and to $\beta$-xylosidase (often concomitantly expressed) has rarely been reported (Quirce et al., 2002; Sander et al., 1998) but is highly unlikely to be of any significant concern since ingested enzyme that will ultimately be digested itself as a protein food substrate.

The presence of mycotoxins sometimes are a consideration when considering the use of mold (fungal cultures) for production of biologics for use in humans or animals. Of concern herein is the co-expression of several low molecular weight aflatoxins and metabolites that rarely may be expressed with AMG by certain *Aspergillus* species (Wilson et al., 2002) The FDA places strict limits on the amount of several aflatoxins may be permitted to be present in foodstuffs (Mazumder and Sasmal, 2001). In contrast, the trichothecenes (e.g., cyclic sesquiterpenoids), deoxynivalenol (DON) is one of the most common nuisance contaminants of various foodstuffs and has been reported to be produced by *Fusarium* genus and some species of *Aspergillus* (Milicevic et al., 2010; Pieters et al., 2002). Specifically, it was discovered that DON was present in food grade AMG and is herein first reported with this present application and disclosure. AMG was originally intended for small, homeopathic dosages and it was determined to be problematic when dosages were efficaciously increased to increase dietary starch digestion in humans. As the dose of AMG was increased, so too was the concentration of DON concomitantly increased. DON is potent, low molecular weight mycotoxin that has been reported may lead to self-limiting vomiting, diarrhea, and other symptoms that affect the cholinergic receptors and is not known to cause serious or lasting illness (Pestka and Smolinski, 2005). Trichothecenes, of which DON is a constituent class member, are reactive species and removal from the final composition will extend the stability and shelf-life of the final composition (AMG). Some trichothecenes can be tested for and are removed by decanting lipid layer when crude AMG is put in aqueous solution (Koch, 2004; Fernandez et al., 1994; Papageorgiou et al., 2018) or by absolute alcohol precipitation of AMG and extraction followed by assay. The universal limit for DON ingested is 1 μg/kg body weight/day for DON and its related metabolites and this represents a significant limiting factor for expanded clinical use. It appears that DON may be a marker for other trichothecenes or DON-derivatives that may or may not be clinically toxic, but not readily detected and, in a similar way, most or all toxins should be removed prior to clinical use of AMG.

Ochratoxin A (MW 403.8D) is of modest concern since it presence is unlikely since it is not known to be associated with AMG-producing *Aspergillus niger* (only *A. carbonarius* which is not the subject of this present disclosure) (Abarca et al, 1994; Trenk and Chu, 1971). It is mentioned herein because it is potentially carcinogenic to human, is a neurotoxin, and is potentially nephrotoxic fat soluble ochratoxin A may be present in low concentrations in AMG if other species, including *Penicillium verrucosum, P. nordicum*, were aberrantly introduced to the bioreactors; pointing to the need to source only quality raw materials (Stoll et al, 2013) and purify the composition. FDA limits the appearance concentration of Ochratoxin A to less than 50 ppb, and AMG derived from pure cultures of *A. niger* universally meets this requirement (Malir et al, 2001). Ochratoxin A is also highly soluble in ethanol (10-50 mg/mL). Commercial, ISO/IEC 17025:2005 certified laboratories are available to routinely test for some mycotoxins in crude or finished products.

The present application and disclosure satisfies a long-felt need in the art of compositions for enhancing starch digestion, preventing maldigestion, relieving the symptoms of maldigestion, and increasing caloric yield and includes methods for preparing the compositions.

BRIEF SUMMARY

The present disclosure is directed to methods and compositions related to the toxin-free enhancement of starch digestion and caloric yield for mammals, including humans, dogs, cats, cows, horses, goats, sheep, pigs, and so forth. Methods of producing the compositions are also encompassed in the disclosure. In particular embodiments, the methods and compositions are related to the production and/or use of particular formulations of amyloglucosidase (AMG). In specific embodiments, the AMG is particularly concentrated and formulated to lack one or more toxins. The one or more toxins may be intentionally excluded from the AMG formulations. In many cases, the formulations are produced with the intent of making the AMG formulations to have fewer or no toxins compared to crude or unprocessed formulations of AMG. In specific embodiments, the formulations are toxin-free or have substantially reduced levels of one or more toxins compared to other formulations and, as such, the concentrated, toxin-free compositions confer clinical utility.

Production methods for the AMG formulations are able to refine, concentrate, and make toxin-free amyloglucosidase, in specific embodiments. In some cases, the AMG formulation is present in a particular form, such as a capsule, for example. In certain cases, the AMG formulation comprises an amount of AMG that is other than an amount of known formulations. In specific cases the AMG amount is able to be higher than known formulations because the AMG lacks one or more toxins that standard AMG formulations have.

In specific embodiments, methods of production allow for production of AMG formulations lacking deoxynivalenol "vomit toxin" that is present in known formulations, including formulations having the crude enzyme. The methods of production may include one or more particular ethanol washing steps that eliminate the deoxynivalenol and its related metabolites from a crude enzyme preparation, for example. Such washing steps may reduce the amount of deoxynivalenol at least 10-fold or more with each absolute ethanol wash/extraction step, in at least some cases.

In particular embodiments, AMG formulations are used for amyloglucosidase supplementation in congenital sucrase isomaltase, small bowel mucositis, functional bowel disorders (including irritable bowel syndrome and functional dyspepsia, for example), functional bowel syndrome, functional gastroduodenal disorders, and protein calorie (energy) malnutrition, for example. Use of the formulations allows improved complex carbohydrate digestion that prevents at least excessive colonic fermentation, decrease inflammation and osmotic diarrhea upon increasing caloric absorption. The methods and compositions of the disclosure assist the body in normal digestion and assimilation of food starch.

Embodiments of the disclosure include methods of optimizing starch digestion in an individual, comprising the step of providing to the individual an effective amount of a composition comprising amyloglucosidase. The composition may comprise amyloglucosidase in a dosage that is equal to or greater than 5,000 unit releases of one gram of glucose per hour (AGU), in at least some cases. The composition may be provided to the individual orally and it may occur daily, weekly, monthly, or yearly, or more than once daily. The individual may or may not be healthy or malnourished but may be in need of treatment or prevention of congenital sucrase isomaltase syndrome, functional bowel disorders, functional bowel syndrome, functional gastroduodenal disorders, small bowel bacterial overgrowth, radiochemotherapy-induced mucositis and/or short-gut syndrome. The individual may be an infant, child, adolescent, teenager, or adult.

The AMG composition may be formulated in any appropriate manner but in specific embodiments is formulated in a comestible or beverage. The AMG may be a food ingredient, medical food, dietary supplement, nutraceutical, and/or drug preparation. The AMG composition may be in the form of a solid, liquid, or gel. It may be a capsule, tablet, pill, film, lozenge, powder, or combination thereof.

In some embodiments there are methods for producing a purified amyloglucosidase composition comprising extracting a crude amyloglucosidase composition in the presence of an immiscible solvent, and separating a purified amyloglucosidase composition from the immiscible solvent. The immiscible solvent may be absolute ethanol, acetone, dimethyl sulfoxide, methanol, chloroform, diethyl ether, or a combination thereof. In particular cases the solvent from which the purified amyloglucosidase composition is separated comprises one or more detectable or non-detectable toxins. The crude amyloglucosidase composition may be in the form of a solid. In particular embodiments, the step of extracting comprises vortexing the crude amylglucosidase composition and the immiscible solvent. Isolating the retained, purified amyloglucosidase composition may comprise spinning down the amyloglucosidase composition, such as in a centrifuge. The method may include repeating the extracting and isolating steps one or more times, including two or more times. The method may further comprise dissolving the retained amyloglucosidase composition in water to form a solution, and filtering the solution.

The crude amyloglucosidase may be supplied in the form of a liquid or a solid. When the crude amyloglucosidase is in the form of a liquid, the crude liquid amyloglucosidase may be admixed with an inert excipient and followed by purification processing. When the crude amyloglucosidase is in the form of a solid, it may have been previously admixed with an organic excipient, such as starch or maltose or a relatively inert excipient(s) such as a calcium salt. In some embodiments, there is a method for optimizing starch digestion in an individual, comprising the step of providing to the individual an effective amount of an amyloglucosidase composition produced by a method encompassed by the disclosure.

In certain embodiments, there are methods of optimizing starch digestion in an individual, comprising the step of providing to the individual (such as orally) an effective amount of a composition comprising toxin-free amyloglucosidase (AMG), wherein the effective amount is at a dosage range 5,000-20,000 AGU, although in some cases the effective amount is at a dosage range lower than 10,000 AGU or higher than 20,000 AGU. The AMG may be released at 5,000-20,000; 5,000-15,000; 5,000-12,000; 5,000-10,000; 5,000-9,000; 5,000-8,000; 5,000-7,000; 5,000-6,000; 6,000-20,000; 6,000-15,000; 6,000-12,000; 6,000-10,000; 6,000-8,000; 7,000-20,000; 7,000-15,000; 7,000-12,000; 7,000-10,000; 8,000-20,000; 8,000-15,000; 8,000-12,000; 8,000-10,000; 6,000-10,000; 6,000-9,000; 6,000-8,000; 6,000-7,000; 7,000-10,000; 7,000-9,000; 7,000-8,000; 8,000-10,000; 8,000-9,000; 9,000-10,000; 10,000-20,000; 10,000-19,000; 10,000-18,000; 10,000-17,000; 10,000-16,000; 10,000-15,000; 10,000-14,000; 10,000-13,000; 10,000-12,000; 10,000-11,000; 11,000-20,000; 11,000-19,000; 11,000-18,000; 11,000-17,000; 11,000-16,000; 11,000-15,000; 11,000-14,000; 11,000-13,000; 11,000-12,000; 12,000-20,000; 12,000-19,000; 12,000-18,000; 12,000-17,000; 12,000-16,000; 12,000-15,000; 12,000-14,000; 12,000-13,000; 13,000-20,000; 13,000-19,000; 13,000-18,000; 13,000-17,000; 13,000-16,000; 13,000-15,000; 13,000-14,000; 14,000-20,000; 14,000-19,000; 14,000-18,000; 14,000-17,000; 14,000-16,000; 14,000-15,000; 15,000-20,000; 15,000-19,000; 15,000-18,000; 15,000-17,000; 15,000-16,000; 16,000-20,000; 16,000-19,000; 16,000-18,000; 16,000-17,000; 17,000-20,000; 17,000-19,000; 17,000-18,000; 18,000-20,000; 18,000-19,000; or 19,000-20,000 AGU. The individual may be in need of treatment or prevention of congenital sucrase isomaltase syndrome, functional bowel disorders, functional bowel syndrome, functional gastroduodenal disorders, small bowel bacterial overgrowth, radiochemotherapy-induced mucositis and/or short-gut syndrome. In some cases the providing step occurs daily, more than daily, weekly, monthly, or yearly. The individual may be healthy or malnourished, and the individual may be an infant, child, adolescent, teenager, or adult. In any case, the composition may be formulated in a comestible or beverage, including in a food supplement. The AMG composition may be in the form of a solid, liquid, gel, or mist, including as a capsule, tablet, pill, film, lozenge, powder, or combination thereof.

In some embodiments, there is a toxin-free AMG composition, or an AMG composition comprising substantially reduced levels of toxin with reference to an AMG composition that has not been subjected to at least one extraction/purification step. Toxin-free AMG compositions produced by methods described herein are encompassed by the disclosure. The composition may be present in a capsule, tablet, pill, film, lozenge, powder, or combination thereof. The amyloglucosidase may be in a dosage that is equal to or greater than 10,000 unit releases of one gram of glucose per minute.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

It is specifically contemplated that any limitation discussed with respect to one embodiment of the disclosure may apply to any other embodiment of the invention. Furthermore, any composition of the disclosure may be used in any method of the invention, and any method of the disclosure may be used to produce or to utilize any composition of the invention. Aspects of an embodiment set forth herein are also embodiments that may be implemented in the context of embodiments discussed elsewhere in the application, such as in the Summary of Invention, Detailed Description, Claims, and description of Figure Legends.

BRIEF DESCRIPTION OF THE DRAWINGS

For a more complete understanding of the present disclosure, reference is now made to the following descriptions taken in conjunction with the accompanying drawing, in which:

Reduced Gel: Lane 1—Molecular Weight Markers; Lane 2—Sample 700126425; Lane 3—Sample Filtered AMG (700126424A) before processing; Lane 4—Sample Filtered AMG (700126424B) before processing; Lane 5—Sample Filtered AMG (700126424A) after processing; Lane 6—Sample Filtered AMG (700126424B) after processing Non-Reduced Gel: Lane 7—Molecular Weight Marker; Lane 8—Sample 700126425 NR; Lane 9—Sample Filtered AMG (700126424A) before processing NR; Lane 10—Sample Filtered AMG (700126424B) before processing NR; Lane 11—Sample Filtered AMG (700126424A) after processing NR; Lane 12—Sample Filtered AMG (700126424B) after processing NR

FIG. 10: Production comparison of processed Ultrabiologic® material when hydrolyzing rice compared to AMG capsule when hydrolyzing rice.

FIG. 12: Production comparison of processed Ultrabiologic® material when hydrolyzing maize compared to AMG capsule when hydrolyzing maize.

DETAILED DESCRIPTION

Figure 1:
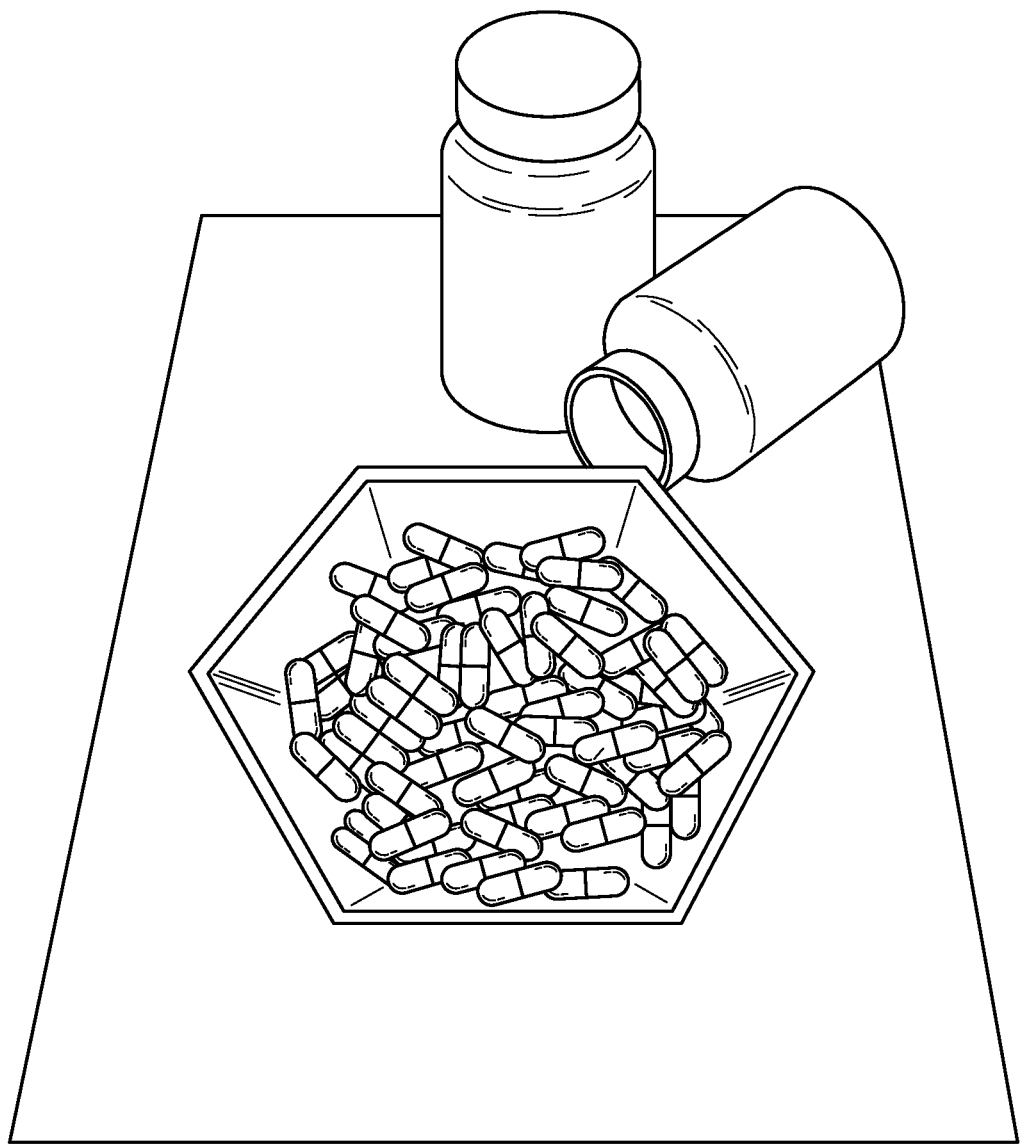
FIG. 1: The proto-type AMG nutritional food supplement prepared under clean conditions for further in-vitro testing. Each capsule as one example may be 8 mm×24 mm in dimension or larger (10 mm×28) mm or smaller (5 mm×15 mm) and contains approximately 500 mg. powder content or more (approximately 750 mg.) or less (approximately 250 mg.), most of which is neutral excipient used to deliver dry enzyme during preparation. Each capsule has approximately 4000 AGU enzymatic activity on maize and 8000 AGU enzymatic activity, or more, on sorghum starch or maltodextrin or dextrin from corn.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the composition or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

The term "toxin-free" as used herein refers to lacking one or more toxins in comparison to a standard formulation. In specific cases, toxin-free refers to lacking deoxynivalenol (vomit toxin), including lacking detectable levels of vomit toxin. In alternative cases, a formulation may have detectable level of vomit toxin but the level is substantially reduced following production methods of the disclosure. In certain embodiments, the level is decreased to a concentration below maximum acceptable levels deemed by regulatory authorities. In some embodiments, a particular way to reduce the level of deoxynivalenol (vomit toxin) is by serial absolute organic solvent washes (absolute ethanol extractions) until low or undetectable levels of deoxynivalenol are achieved, as measured by gas chromatographic mass spectrometry or by thin-layer chromatography or by use of commercial ELISA assay, such as DON-V® (VICAM, a Waters Business, Milford, Mass. 01757. The substantially reduced level of vomit toxin may be reduced in a formulation compared to the level in a starting or crude formulation, such as reduced by a level that is 10, 20, 30, 40, 50, 60, 70, 80, 90, 91, 92, 92, 94, 95, 96, 97, 98, or 99% lower than a starting or crude formulation or by direct testing using ELISA (less than 0.05 ppm-per-gram of purified AMG). In particular embodiments, there is less than 0.05 parts per million (ppm) per gram of refined (washed) AMG. In some embodiments, there is less than 0.5, 0.4, 0.3, 0.2, 0.1, 0.09, 0.08, 0.07, 0.06, 0.05, 0.04, 0.03, 0.02, or 0.01 ppm per gram of refined (washed) AMG.

I. General Embodiments

Survival in healthy or diseased states depends on an adequate and continuous supply of energy in the form of glucose delivered to all cells in the body. Approximately half of the body glucose needed for energy needs is derived from dietary starches, with the balance being derived from a variety of sources including dietary and stored fat, protein stuffs, and glycogen stores. Malnourished children, living in remote parts of sub-Saharan Africa, have limited energy stores and are unable to fully assimilate the relatively dilute nutritional content of some dietary staple grains, including millet, sorghum, maize and cassava and due to limited digestibility, especially during states of chronic illness.

For example, in Tanzania, poverty and food insecurity are the main drivers of chronic under-nutrition and is indirectly responsible for more than 130 child deaths every day. There are 8 million Tanzanian children aged less than five-years old, and 42% have stunted growth and 16% are considered underweight and recurrent diarrhea and failure to assimilate dietary calories is the primary putative factor. Most work has focused on the means to increase protein derived from grains, but the need to increase energy yield from dietary starch (polysaccharides) is also important. In addition to caloric intake, micronutrient deficiencies are widespread and parallels caloric intake, with more than half of malnourished children, aged less than five years, are also considered anemic. Childhood malnutrition is most prevalent (50 percent or higher) in the regions of Dodoma, Iringa, Mbeya, Njombe, Rukwa, and Lindi, so a method to increase caloric assimilation from nutritionally sparse grains is needed.

This disclosure addresses the embodiment that starch digestion and caloric yield can be enhanced by optimizing luminal carbohydrate digestion with an orally administered supplemental enzyme, amyloglucosidase (AMG). This is a feasible approach to increase daily energy gains and improve the health of malnourished children. Such an approach would also be useful for treatment of congenital sucrase isomaltase syndrome (Gericke et al., 2016), functional bowel disorders (Henstrom et al., 2018; El-Chammas et al., 2017), small bowel bacterial overgrowth, radiochemotherapy induced mucositis and short-gut syndrome. For these purposes, the associated technical considerations toward optimizing starch digestion using amyloglucosidase are addressed. Embodiments of the disclosure include daily AMG supplementation, for example, with the overarching goal of improving growth and general health of the afflicted.

In some embodiments, at least two ethanol washes are required to significantly decrease the crude AMG of toxin in which the process exploits the feature that the AMG is completely insoluble in ethanol and deoxynivalenol is completely soluble. The knowledge of this dichotomy is not obvious, since deoxynivalenol is seldom, if ever, tested for in products derived from *A. niger*; a totally unexpected finding and unique and useful to these purposes.

II. Amyloglucosidase (AMG) Compositions

The present disclosure includes AMG compositions that are specifically formulated (and may also be referred to as AMG formulations). The AMG compositions may be produced by methods described herein. In particular embodiments, the AMG formulations may or may not have a specific amount of AMG within. In certain embodiments, the AMG formulation is toxin-free or is substantially reduced in the level of one or more toxins compared to a standard or crude preparation. The toxin may be of any kind, but in specific embodiments the toxin is deoxynivalenol (vomit toxin). In particular embodiments, the AMG formulation has both of (1) a particular amount of AMG; and (2) is toxin-free or substantially reduced in its level of toxin(s).

In particular cases, the level of AMG in the AMG formulation is equal to or greater than 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; or greater unit releases of one gram of glucose per hour (AGU). In specific cases, AMG is released at 5 The AMG may be released at 5,000-20,000; 5,000-15,000; 5,000-12,000; 5,000-10,000; 5,000-9,000; 5,000-8,000; 5,000-7,000; 5,000-6,000; 6,000-20,000; 6,000-15,000; 6,000-12,000; 6,000-10,000; 6,000-8,000; 7,000-20,000; 7,000-15,000; 7,000-12,000; 7,000-10,000; 8,000-20,000; 8,000-15,000; 8,000-12,000; 8,000-10,000; 6,000-10,000; 6,000-9,000; 6,000-8,000; 6,000-7,000; 7,000-10,000; 7,000-9,000; 7,000-8,000; 8,000-10,000; 8,000-9,000; 9,000-10,000; 10,000-20,000; 10,000-19,000; 10,000-18,000; 10,000-17,000; 10,000-16,000; 10,000-15,000; 10,000-14,000; 10,000-13,000; 10,000-12,000; 10,000-11,000; 11,000-20,000; 11,000-19,000; 11,000-18,000; 11,000-17,000; 11,000-16,000; 11,000-15,000; 11,000-14,000; 11,000-13,000; 11,000-12,000; 12,000-20,000; 12,000-19,000; 12,000-18,000; 12,000-17,000; 12,000-16,000; 12,000-15,000; 12,000-14,000; 12,000-13,000; 13,000-20,000; 13,000-19,000; 13,000-18,000; 13,000-17,000; 13,000-16,000; 13,000-15,000; 13,000-14,000; 14,000-20,000; 14,000-19,000; 14,000-18,000; 14,000-17,000; 14,000-16,000; 14,000-15,000; 15,000-20,000; 15,000-19,000; 15,000-18,000; 15,000-17,000; 15,000-16,000; 16,000-20,000; 16,000-19,000; 16,000-18,000; 16,000-17,000; 17,000-20,000; 17,000-19,000; 17,000-18,000; 18,000-20,000; 18,000-19,000; or 19,000-20,000 AGU. In some cases, the AMG formulation comprises approximately 20000 AGU activity units per gram (2 capsules) or less dependent upon desired dilution.

In particular embodiments, the level of AMG in a formulation or combination of formulations is greater than 20,000 AGU. The skilled artisan recognizes that lower levels of AMG in an AMG formulation may be more suitable for use as a supplement, whereas higher levels of AMG in an AMG formulation may be more suitable for use in another purpose, such as a medical food.

In certain embodiments, the AMG composition is formulated in a specific form, such as a tablet, pill, film, lozenge, powder, capsule, or combination thereof. In particular cases the AMG formulation is a capsule. In cases wherein the AMG formulation is in a capsule, the capsule may comprise at least about 1000, 2000, 3000, 4000, 5000, 6000, 7000, 8000, 9000, or 10,000 or more AGU, particularly about 8000 AGU. In other cases, an AMG formulation in a capsule comprises no more than about 1000, 2000, 3000, 4000, 5000, 6000, 7000, 8000, 9000, or 10,000 or more AGU. The skilled artisan recognizes that with capsule preparation (as an example) the enzyme content may be determined by the number of times that one admixes (for example, by spray) a purified, toxin-free liquid containing the AMG to the excipient and allowing it to dry. In some cases, after the drying step, in subsequent steps one could again admix the toxin-free liquid containing the AMG with unpacked powder (the excipient) to increase the concentration.

Nutraceutical compositions of the present disclosure (that may also be referred to as medicinal food, medical food as defined in section 5(b) of the Orphan Drug Act (21 U.S.C. 360ee (b) (3)), food ingredient, dietary supplement, and/or drug preparation) comprise an effective amount of one or more AMG compositions dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a nutraceutical composition that contains at least one AMG composition or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The AMG composition may comprise different types of carriers depending on whether it is to be administered in solid, liquid or aerosol form, and whether it need to be sterile for such routes of administration as injection. The present invention can be administered enterically, intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The AMG composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the AMG composition of the present disclosure suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

One of ordinary skill in the art would be familiar with the range of techniques that can be employed for dispersing a composition in a lipid vehicle. For example, the AMG compositions may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In particular embodiments of the present disclosure, the AMG compositions are formulated to be administered via an alimentary route. Alimentary routes include all possible routes of administration in which the composition is in direct contact with the alimentary tract. Specifically, the pharmaceutical compositions disclosed herein may be administered orally, buccally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate, aluminum hydroxide, magnesium hydroxide, sodium bicarbonate, calcium carbonate, calcium phosphate, calcium silicate, calcium chloride, or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In particular embodiments of the AMG compositions, no stabilizers are present.

In particular embodiments, the AMG composition is combined with one or more other therapeutic agents. An individual may receive the AMG composition in the same composition as the one or more other therapeutic agents, or the individual may receive them separately. In some cases, the one or more other therapeutic agents comprise an agent that facilitates digestion of biological molecules other than starch, such as sugar, lactose, and so forth. In specific cases the one or more other therapeutic agents comprise invertase, sucrose, lactase, xylose isomerase (glucose isomerase), beta-galactosidase, or a combination thereof. In other specific cases the one or more therapeutic agents that constitute type-2-histamine receptor antagonists (e.g., ranitidine HCl) or benzimidizoles, also known as proton-pump inhibitors (e.g., omeprazole), or a combination thereof.

III. Methods of Producing Amyloglucosidase (AMG) Compositions

Methods of producing one or more AMG compositions are encompassed in the disclosure. In particular embodiments, the method is performed for the purpose of removing or reducing the level of one or more toxins. The method of producing toxin-free AMG compositions or substantially reduced levels of toxin in AMG compositions may be performed with the intent of removing toxin(s) from commercially sourced raw/crude product (as an example). Crude AMG may be produced from *A. niger* using wet submersion or solid state techniques, for example.

Embodiments of the disclosure include methods for producing purified AMG compositions, including toxin-free AMG compositions or compositions have reduced levels of AMG compared to starting AMG compositions. In some cases the method steps comprise extracting a crude AMG composition in the presence of an immiscible solvent and separating a purified AMG composition from the immiscible solvent. A crude AMG composition (which may be a solid) may be defined as one that has not been subjected to an extraction/purification step and/or it is a composition from which toxins and other impurities have not been removed intentionally. Although the immiscible solvent may be of a variety of suitable kinds, in specific embodiments the immiscible solvent is absolute ethanol. In particular embodiments, the solvent from which the purified AMG composition is separated comprises one or more toxins, including the deoxynivalenol "vomit toxin" from the crude enzyme, as an example. The extracting step may comprise vortexing (mixing) and/or blending the crude AMG composition and the immiscible solvent.

The method may include isolating steps of any kind, but in specific cases the isolating of the retained, purified AMG composition comprises spinning down the amyloglucosidase composition in a centrifuge or permitting gravity separation to occur over prolonged time.

In the production methods, one or more steps may be repeated, including at least repeating the extracting and/or isolating steps one or more times, for example.

Once the AMG composition has been isolated, it may be further modified or prepared, such as dissolving the retained AMG composition in a solvent (such as water) to form a solution or suspension. In at least some cases the solution or suspension may be filtered, centrifuged, and/or separated by gravity over time.

In some embodiments, the resultant AMG composition produced by methods of the disclosure is formulated into a particular composition that is a capsule, tablet, pill, film, lozenge, powder, or combination thereof, as examples. Aqueous AMG solution may be admixed with inert excipient, such as calcium carbonate, calcium phosphate and calcium silicate or a combination thereof and dried to powder for mechanical or hand gelatin encapsulation.

In specific embodiments, AMG compositions of the disclosure are utilized immediately or they may be stored, such as under dry conditions, low humidity and room temperatures while avoiding excessive heat or cold. It may be transported prior to use.

IV. Alternative Method of Producing Amyloglucosidase (AMG) Compositions

In specific embodiments, crude AMG is supplied by a producing vendor in the form of a particulate-free dark, semi-opaque liquid product of *Aspergillus niger* liquid-state fermentation that is intended for production of purified dry composition. The crude liquid AMG may contain DON toxin and/or other non-detectable organic impurities including sesquiterpenes and sesquiterpenoids. The sesquiterpenes and sesquiterpenoids are by nature, lipophillic and soluble in absolute ethanol. As supplied by the vendor, the crude liquid AMG may have an enzyme activity that approximates 1000 AGU per milliliter (1000 AGU per milliliter could be 100-500 AGU, 500-1000 AGU, 1000 to 1500 AGU, 1500-2000 AGU, 2000-2500 AGU or 2500-3000 AGU) and must be in a dry form to facilitate purification of the final composition.

In specific embodiments, the purification process uses Good Manufacturing Practices and will take place in a controlled, low humidity clean room supplied by high efficiency particulate air filtered air (limit 0.3 micrometers) and includes several concentration steps that includes admixing crude liquid AMG to inert solid excipient, such as a mixture calcium carbonate, calcium phosphate and calcium silicate ("excipient mixture") to create a batter using a standard low-speed bakers mixer and stainless steel bowl or similar instrument. The batter is spread thinly over food-grade plastic wrap used as liner for large cookie sheets (i.e., sized 24×36 inches) to maximize evaporative surface areas and the batter is permitted in evaporate in extremely low humidity, clean room conditions at approximately 10-15 degrees until visibly dry. Alternatively, the crude liquid AMG may be applied to the excipient mixture by aerosolizing the crude liquid AMG and spray-applied it evenly to the excipient mixture layers contained by the cookie sheets. The admixture is composed of a ratio of 4 parts crude liquid AMG to 1 part excipient mixture and permitted to dry by evaporation over a period of 24-hours to 36-hours depending upon conditions to yield a crude composition. Dryness is determined by brittle nature of the composition and the lightening of the color from dark brown to light tan with a dusty white. The dry crude composition is then recovered to a clean blender (such as Waring 023909) and pulverized to a fine powder, taking care not to heat the crude composition with prolonged high-speed pulverization and using short bursts of pulverizing activity is best practice. With the intention to concentrate the final composition to yield high enzymatic activity, additional crude liquid AMG may be admixed again with the primary dry crude composition a ratio of 4 parts crude liquid AMG to 1 part excipient mixture and permitted to dry by evaporation over a period of 24-hours to 36-hours depending upon conditions to yield a secondary concentrated crude composition. This admixing sub-process may be repeated to increase enzyme activity to the degree that it becomes impractical to advance with purification processes described below.

After repeat pulverization, the secondary concentrated crude composition is aliquoted is small batches to high density, food-grade polypropylene containers (for example 1 liter capacity (for example Nalgene 2178-2025 Tritan 32 oz W/M, Gray w/Blue Cap), for extraction (washing) to which absolute ethanol is added in a ratio of 1 part absolute ethanol (USP grade) to 1 part secondary composition such that the combined volume of the container approximates 66 percent of capacity. The capacity of the container should not exceed 75% total volume so as to permit excellent agitation during the extraction phase. In clean room conditions at approximately 10-15 degrees the extraction phase is performed whereby the secondary composition/ethanol mixture is gastight sealed and shaken vigorously at least 30 minutes using a commercial paint can shaker-mixer, such as Red Devil Paint Shaker: Multi-Size Case Shaker machine, 5 gal Container Size 5995PB, or similar device, that can accept multiple high density, food-grade polypropylene containers within an outer wrapping container used for consolidation and fire safety. After vigorous shaking (extraction/washing) the high density, food-grade polypropylene containers are removed from the shaker machine and the contents within the high density, food-grade polypropylene containers are permitted to separate by gravity (about 2 hours). The alcoholic supernatant is then carefully aspirated to waste taking care to retain the composition within the high density, food-grade polypropylene containers. To each high density, food-grade polypropylene containers containing the composition is added an equal volume of absolute ethanol (USP grade), whereupon the container are resealed and again, the high density, food-grade polypropylene containers are shaken vigorously at least 30 minutes using a commercial paint can shaker-mixer, such as Red Devil Paint Shaker: Multi-Size Case Shaker machine, 5 gal Container Size 5995PB, or similar device, that can accept multiple high density, food-grade polypropylene containers within an outer wrapping container used for consolidation and fire safety. After vigorous shaking (extraction/washing) the high density, food-grade polypropylene containers are removed from the shaker machine and outer container and the contents are permitted to separate by gravity (about 2 hours). Again, the alcoholic supernatant is then carefully aspirated to waste taking care to retain the composition within the high density, food-grade polypropylene containers. The remaining composition is removed from each high density, food-grade polypropylene container, the composition is thinly distributed on lined cookie sheets as aliquots and any residual ethanol is permitted to evaporate to dry in a safe, spark-free, clean low humidity room. When the composition aliquots are dry, the aliquots are pulverized, well mixed, and combined to bulk packaging that includes heavy duty, food grade plastic bags (such as Hefty Slider 2.5 Gallon Jumbo Storage Bags, Reynolds Consumer Product UPC 700064844090), labeled and made ready for release testing and distribution according to specifications. The composition may be diluted with excipients to yield a desired, lower enzymatic activity. AMG compositions of the disclosure are utilized immediately or they may be stored, such as under dry conditions, low humidity and room temperatures while avoiding excessive heat or cold. It may be transported prior to use.

V. Methods of Optimizing Starch or Fructans Digestion

In particular embodiments, an effective amount of an AMG composition encompassed by the disclosure is provided to an individual in need thereof, including an individual in need of optimizing or improving starch or fructans digestion. The individual may be in need of AMG supplementation for any reason. In other cases, the individual may not be in need of AMG supplementation but instead is taking AMG composition(s) of the disclosure as a routine practice, as maintenance, or as prevention of a need for AMG supplementation. In specific embodiments, an individual has a medical condition associated with insufficient disaccharidase levels or insufficient starch digestion or insufficient fructans digestion, for example. In specific embodiments, the individual has congenital sucrase isomaltase deficiency syndrome, celiac disease, parasitic infestation disease, viral gastroenteritis, mucosal injury from infectious gastroenteritis, small bowel mucositis, a functional bowel disorder, functional bowel syndrome, functional gastroduodenal disorders, and/or protein calorie (energy) malnutrition. Although the individual may be malnourished, in some cases the individual is not malnourished.

In cases wherein the AMG composition is utilized for functional bowel disorders, the individual may have difficulty with one or more of the following: (1) the movement of food and waste through the GI tract; (2) heightened experience of pain in the internal organs; (3) changes in the gut's immune defenses; (4) changes in the community of bacteria in the gut; and (5) changes in how the brain sends and receives signals from the gut.

In cases wherein the AMG composition is employed for functional gastroduodenal disorders, the individual may be experiencing one or more of the following: (1) functional dyspepsia (FD) including postprandial distress syndrome (PDS) and epigastric pain syndrome (EPS); (2) belching disorders including excessive gastric and supragastric belching; (3) chronic nausea and vomiting disorders including chronic nausea vomiting syndrome (CNVS), cyclic vomiting syndrome (CVS) and "cannabinoid hyperemesis syndrome" (CHS); and (4) rumination syndrome.

In specific cases, AMG is utilized for hydrolysis of fructans (polymers of fructose found in many fruits and vegetables). An individual in need of improved digestion of fructans may be provided an effective amount of AMG. In a specific case, an individual is sensitive to FODMAPs ("fermentable oligo-, di-, mono-saccharides and polyols") and is provided an effective amount of AMG. The individual may have fructan intolerance. The individual may be administered AMG at the same time as, before, and/or after the consumption of FODMAPs. In some cases, in addition to taking an effective amount of AMG they may be controlling the consumption of foods or beverages high in fructose. The individual may have fructan maldigestion, such as with consuming prunes and/or raisins.

An individual that consumes or otherwise intake or be administered may be of any gender, race, or age. The individual may be an infant, child, adolescent, or adult, including a gestating adult. The individual may be administered the AMG composition(s) once or more than once. Following administration, such as in a routine manner, improvement of at least one symptom of a medical condition may improve and the individual may or may not continue to receive the AMG composition(s) following this. The individual may be administered the AMG composition daily, 2-3-4-5-6 times daily, weekly, monthly, yearly, etc. The individual may or may not take the AMG composition(s) with food. In some cases, the individual may take the AMG composition before consumption of food and/or beverage, during consumption of food (including starch) and/or beverage, and/or following consumption of food and/or beverage. In cases wherein the AMG composition is taken before the consumption of food, the composition may be microencapsulated for delayed release (or the composition may be microencapsulated for any other reason). In particular cases, the food comprises one or more starches, such as cassava, millet, sorghum, rice, wheat, potato, tapioca, corn, rye, oats, a combination thereof, and so forth. In particular embodiments, the AMG composition is contained within a food or beverage.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Amyloglucosidase as a Nutraceutic for Maldigestion and Malnutrition

Nutritional substances were considered that would be useful in several symptomatic populations, including functional bowel disorder, functional bowel syndrome, functional gastroduodenal disorders, congenital sucrase-isomaltase insufficiency, iatrogenic mucositis, undernourished lactating women, and undernourished children, for example. In particular embodiments, a dietary product is produced that alleviates one or more symptoms of disaccharidase insufficiency from any cause, for example.

Considering that SGLT-1 transporters are relatively conserved, even in the face of severe malnutrition, supplementing or replacing endogenous isomaltase with amyloglucosidase is feasible, as in the case of functional bowel disorder, functional bowel syndrome, functional gastroduodenal disorders, Congenital Sucrase-Isomaltase Deficiency (CSID), mucositis, and small-bowel bacterial overgrowth that is expected to diminish typical malabsorption symptoms caused by excessive colonic fermentation.

Infectious diarrhea that causes significant intestinal mucosal injury and loss of naturally inherent mucosa-bound disaccharidases (sucrase-isomaltase and maltase glucoamylase) often leads to various degrees of malnutrition. Feeding malnourished pediatric patients offers a great challenge. Such a treatment is useful for malnourished children (for example, in sub-Saharan nations) to allow them to efficiently digest their carbohydrate sparse foodstuffs (e.g., sorghum and millet), including while recovering from various illnesses that have compromised their normal digestive capacity. Marasmoid patients have difficulty digesting carbohydrates, which is typically the most abundant (common) food stuff. If digestion of ingested grains could be accelerated, the nutritional benefits could be realized.

In one embodiments, amyloglucosidase is selected for subsequent testing in humans, with or without invertase and/or xylose isomerase, as a medicinal food product (a nutraceutical or food supplement). To meet this objective, several commercial grade samples of amyloglucosidase and invertase and/or xylose isomerase were selected for purity and activity using the following procedures: enzyme concentration by Lowry method, enzyme characterization by SDS-PAGE methodology, enzyme purity by thin layer chromatography screen for low molecular weight contaminants, and enzyme activity by rate of glucose production. The results of these studies facilitated selection of a primary and secondary amyloglucosidase candidate from which a refined material could be encapsulated and repackaged to be used as a nutraceutical or medicinal food.

In another embodiment there is identification of an established manufacturer to prepare and encapsulate amyloglucosidase for human consumption. In a specific embodiment, one tests amyloglucosidase supplement for activity in people with congenital Sucrase-Isomaltase deficiency syndrome and demonstrate symptomatic relief. In another embodiment, amyloglucosidase supplement is tested for activity in people with functional bowel disorder and demonstrates symptomatic relief. One can also test amyloglucosidase supplementation activity in children with protein-calorie malnutrition and demonstrate increased caloric yield by demonstrating weight gain and improved health and well-being or resolution of diarrhea, for example.

Methods Summary

The following is a description of an embodiment of methods of the disclosure.

Sample Preparations: Following receipt of the test article, the several candidate enzyme samples were annotated and given a tracing number. Subsequently, a 50 mL solution was prepared from powder candidate enzyme using standard sodium citrate buffer [10 mM, pH 4.5, Fisher S279; Sigma C0759, de-ionized water (Barnstead NanoPure II)] at a candidate enzyme concentration of 5 mg/mL (Robyt and White, 1987; Standard Solutions). Subsequently, half (25 mL) was dialyzed using 50 kD MWCO cellulose ester membrane tubing (part #131384. Lot #3272198; Spectrum Labs, Rancho Dominquez, C A) in citrate buffer (dialysate) to remove all free glucose and low molecular weight substance that might interfere with subsequent assays. The test article samples underwent a Lowry assay to determine protein concentration and diluted proportionately with standard sodium citrate buffer to yield a concentration of 1 mg/mL for further testing, unless otherwise indicated. In a similar fashion, a candidate crude enzyme provided in liquid form by the manufacturer, was directly dialyzed before determination of protein concentration and, depending upon the determined protein concentration, diluted proportionately with standard sodium citrate buffer to yield a concentration of 1 mg/mL.

Protein Concentration: The Lowry assay is the method of choice for accurate protein determination for cell fractions, chromatography fractions, and enzyme preparations (Robyt and White, 1987; Quantitative determination of proteins). Under alkaline conditions, the divalent copper ions forms a complex with peptide bonds in which it is reduced to a monovalent ion. Monovalent copper ion and the radical groups of tyrosine, tryptophan, and cysteine reactwith Folin reagent to produce an unstable product that becomes reduced to molybdenum/tungsten blue. Sample intensity is measured using an IR-spectrophotometer and results are compared against a standard reference curve to determine sample protein concentration.

SDS-PAGE: Samples underwent sodium-dodecyl-sulfate polyacrylamide gel electrophoresis (SDS-PAGE) analysis to affirm that the product received was as stated and relatively void of extraneous proteins (Robyt and White, 1987; Gel electrophoresis).

Thin Layer Chromatography (TLC): Mycotoxins may be surveyed using gas chromatography (GC), high performance liquid chromatography (HPLC) and thin-layer chromatographic (TLC) methodologies. TLC is a technique used for the identification or separation of compounds in mixtures (Robyt and White, 1987; Thin-layer chromatography). It is routinely used to monitor the consumption of starting material in bioreactors and to observe for the appearance of desired products and problematic contaminants, such as pesticides and toxins (Ambrus et al, 2005). Unwanted organic products produced by *Aspergillus* species may rarely include toxic contaminants such as mycotoxins (ochratoxins) and aflatoxins. Mycotoxins are low molecular weight secondary fugal metabolites that may result in acute or chronic disease. Of particular concern is deoxynivalenol ("DON-V" or "vomit toxin"; C15H20O6/296.32 g·mol-1), a sesquiterpenoid trichothecene and it is among the most often encountered mycotoxins (Lin et al, 1998). It is typically found in grains contaminated by *Fusarium* species. Hundreds of structurally related, LMW mycotoxins are known to exist and epidemiological studies have shown an association of gastrointestinal distress. DON is not known to be carcinogenic, but acute toxicity is potent and the FDA has placed a limit of 1 ppm restriction on it. The most convenient method to test for deoxynivalenol is by use of fluorescent immunochemistry, for which commercial test kits are readily available.

Estimation of Enzyme Activity by Rate of Glucose Production: Samples underwent activity testing to assess which candidate sample enzyme was the most potent for hydrolyzing starch and dextrins and to determine if any of the AMG samples had any a-D-glucopyranosyl-(1 2)-β-D-fructofuranoside hydrolytic activity (Robyt and White, 1987; Determination of enzyme activity). A panel of standard substrates was tested, and results were reported in terms of the rate of glucose production as measured by a glucometer (e.g., Analox GM9, (Robyt and White, 1987; Quantitative determination of carbohydrates). Analox analyzers are based on the principle of enzymatic oxygen uptake of the analyte (sample to be measured) using specific oxidoreductase and dehydrogenase enzymes (reagent consumable) and are used in biotechnology applications (Cass et al, 1984). The instrument uses a highly accurate electrochemical probe to measure oxygen uptake. Example equation (sample+reagent consumable): [β-D-GLUCOSE+O2-glucose oxidase→D-GLUCONIC ACID-$H_2O_2$] The change in oxygen ion concentration is measured by the instrument and change in electrical potential correlates with glucose concentration. Traditional, alternative colorimetric methods are also contemplated.

Examples Of Results

Protein Identification by SDS-PAGE Methodology

Figure 2A:
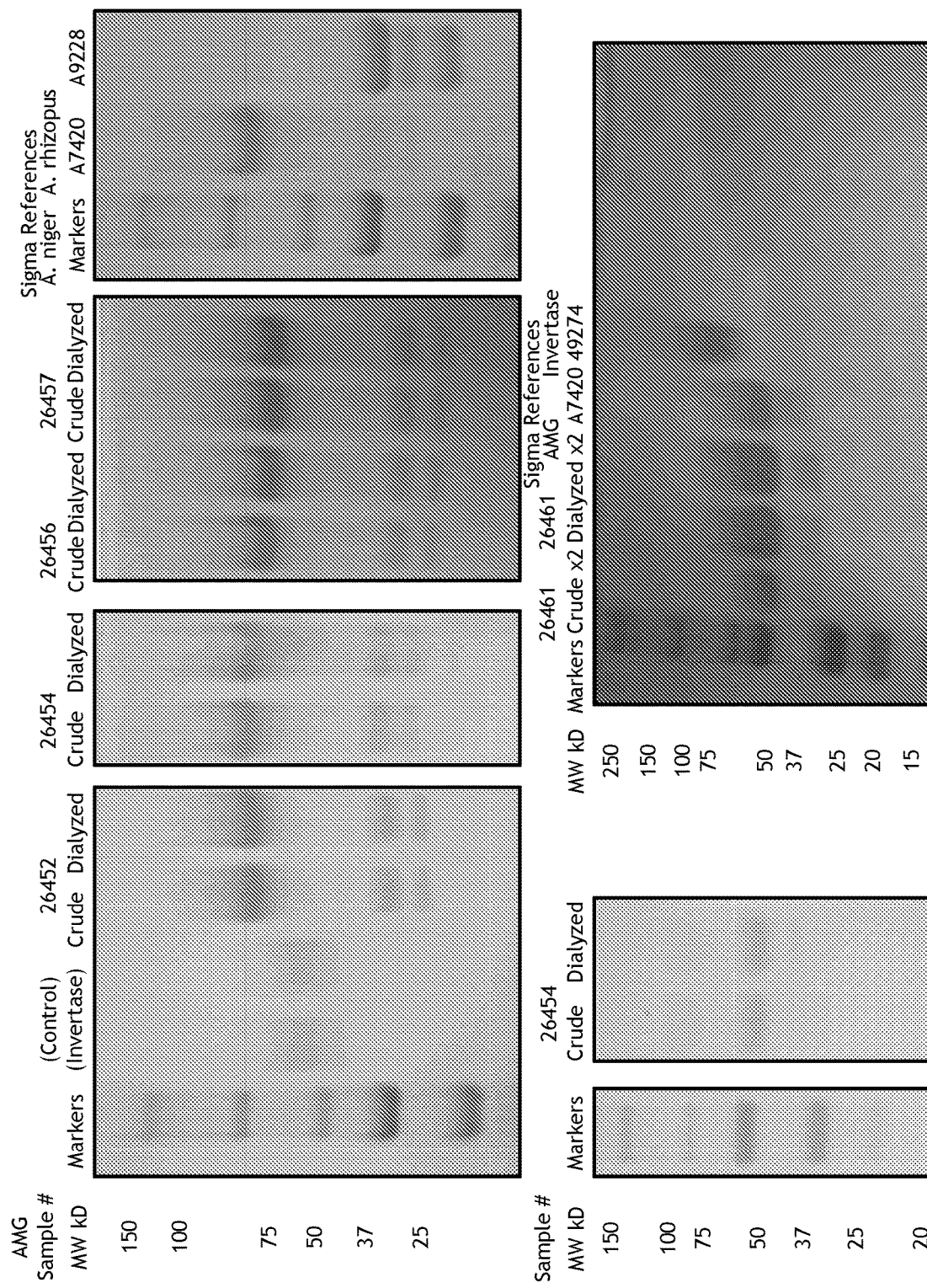
FIG. 2A: SDS-PAGE Results for Amyloglucosidase. The SDS PAGE results for AMG samples 26452, 26454, 26456, 26457, 26459 and 26461, along with Sigma references for *A. niger* A7420 and *A. rhizopus* A9228. The expected results include glycoprotein bands at ~90 kD and a band at ~70 kd. All samples are consistent for AMG, except most dry samples contain additional protein bands as ~60 kD that that probably represent enzyme fragment. This is faintly seen in the Sigma A4720 reference as well. Invertase control is distinguished as a distinct entity.
Figure 2B:
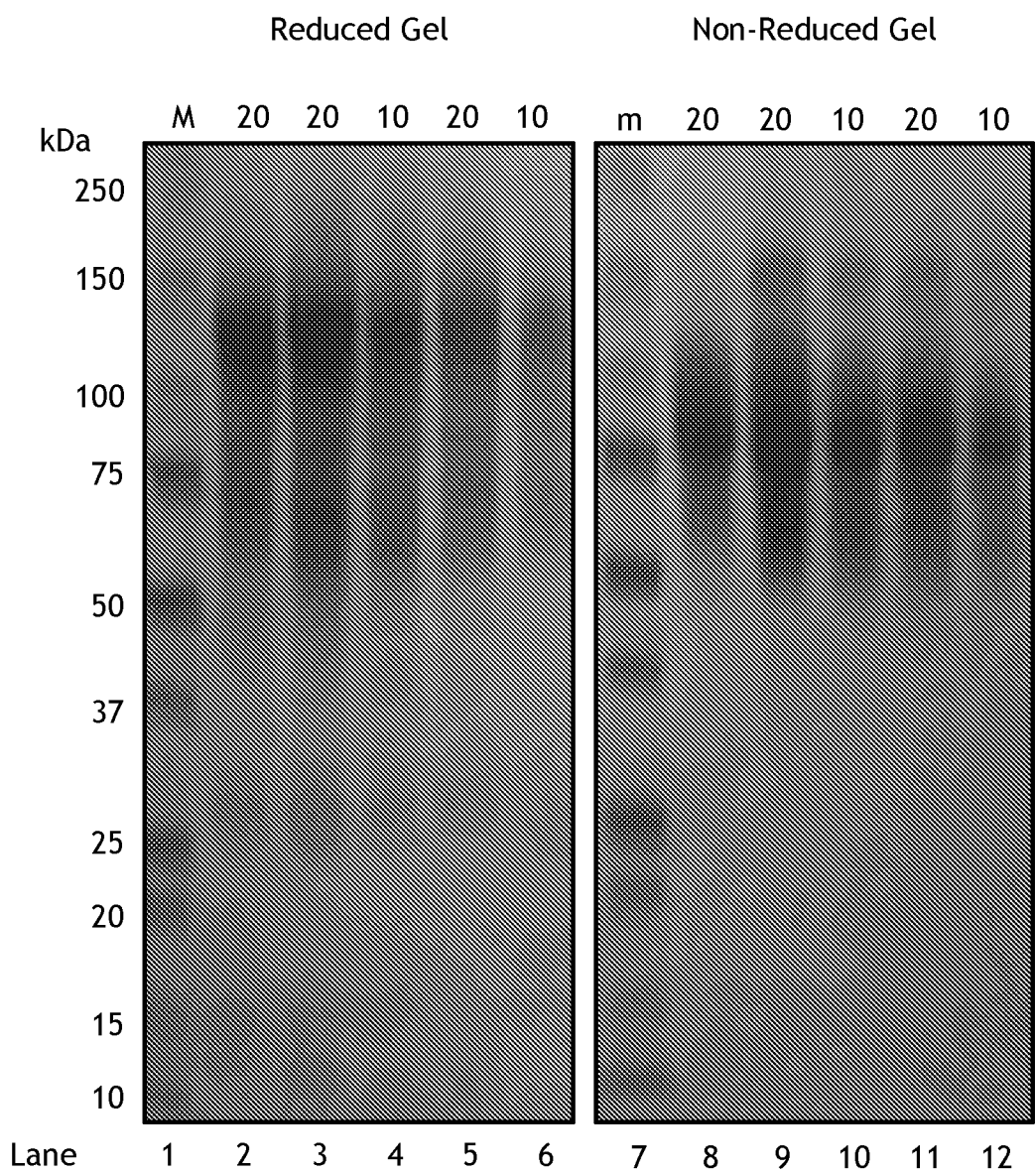
FIG. 2B: SDS-PAGE Results for Amyloglucosidase. The SDS PAGE results for AMG samples Ultrabiologic's Nutritek AMG samples (26424B), along with Sigma references for *A. niger* A7420 (26425). The intensity for the bands is remarkable and consistent with the 53% crude protein content for sample 26424B.

The molecular weight and purity of candidate amyloglucosidase can be estimated with sodium dodecyl sulfate-polyacrylamide gel electrophoresis (SDS-PAGE) techniques. The mobility of an enzyme in a gel is influenced by the size and charge of the molecule; therefore samples are usually treated to have a uniform charge, so electrophoretic mobility in SDS-PAGE depends mainly on molecular weight size. PAGE is carried out in the presence of an anionic detergent, SDS, and a reducing agent mercaptoethanol (BME). SDS disrupts the secondary, tertiary and quaternary structure of the protein to produce a linear polypeptide chain coated with negatively charged SDS molecules and BME contributes with protein denaturation by reducing all disulfide bonds. Conversely, native PAGE-enzymes may be prepared in a non-reducing/non-denaturing sample buffer (SDS-free or BME-free) and in the gel, which should maintain both the enzymes' secondary structure and native charge density to determine the aggregation state. This permits visualization of multiple bands if the target enzyme sample has polymerized forms. SDS-PAGE will not demonstrate the presences of LMW non-protein toxins. The SDS-PAGE results for AMG samples 26252, 26454, 26456, 26457, 26459 26461 26424A, and 26424B, along with Sigma references for *A. niger* and *A. rhizopus*, are shown (FIG. 2A).

Estimation of Purity by Thin-Layer Chromatography

Figure 3:
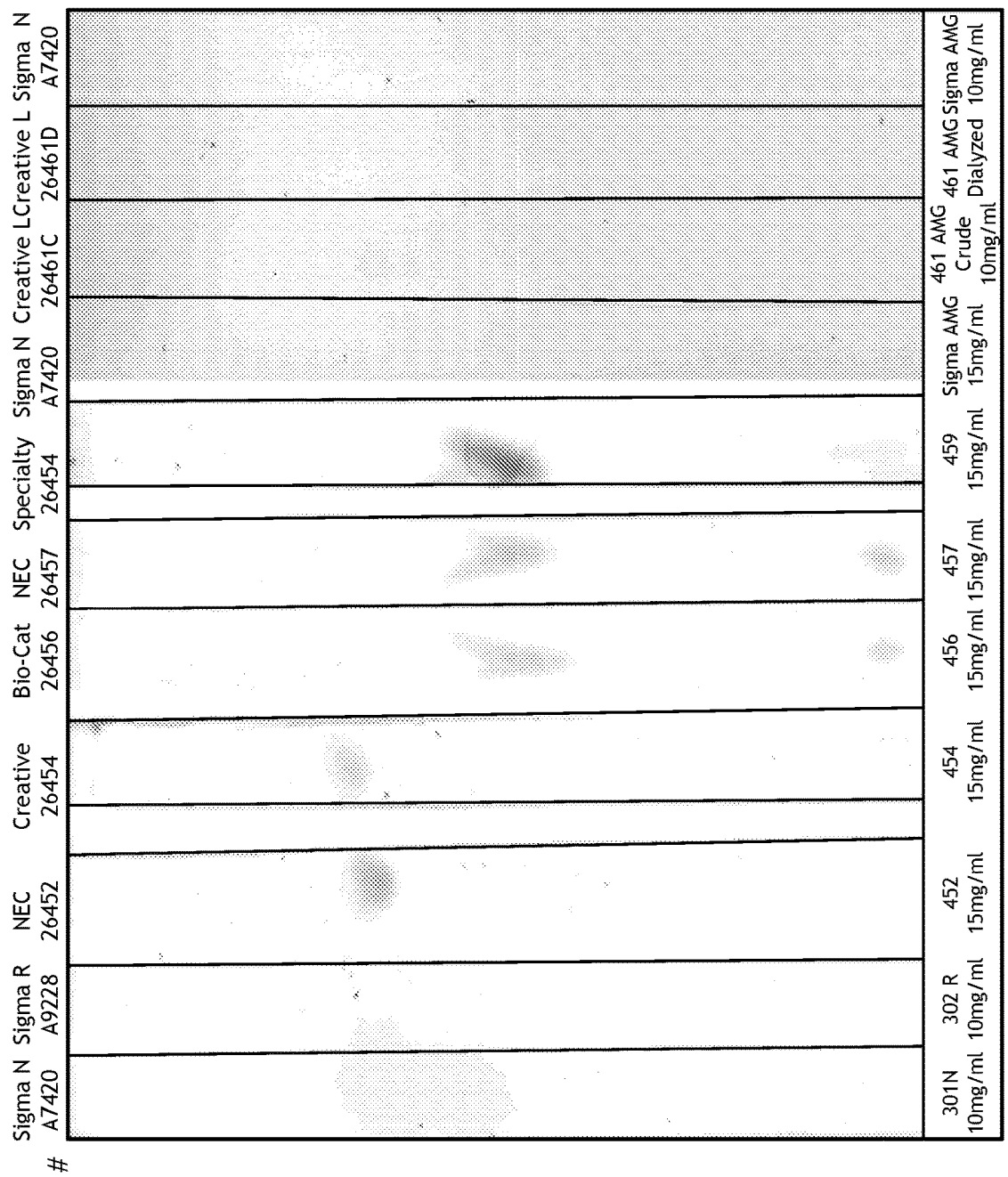
FIG. 3: Thin-layer chromatography results for amyloglucosidase samples. The TLC results for AMG samples 26452, 26454, 26456, 26457, 26459, 26461, 26461-dialyzed along with Sigma references for *A. niger* A7420 (internal #301N). All commercial AMG samples demonstrate LMW bands consistent with typical impurities and flavonoids (i.e., isoflavone aglycones) and/or excipients, except for AMG 26461 and Sigma control samples. Sigma sample 26461 was provided as a crude liquid (syrup) and probably was not adulterated. Samples BIOCAT 26556 and NEC 26457 show aberrant low bands suggestive of mycotoxin (deoxynivalenol, aka: VOMIT TOXIN) or other contaminants that might signal the presence of deoxynivalenol. The importance of dialysis, filtration or some other technique (gel filtration) to remove residual biological substances is considered. (n.b., the presence of isoflavone aglycones, such as daidzein, genistein and glycitein are suspected because of typical fementation aroma.)
Figure 4:
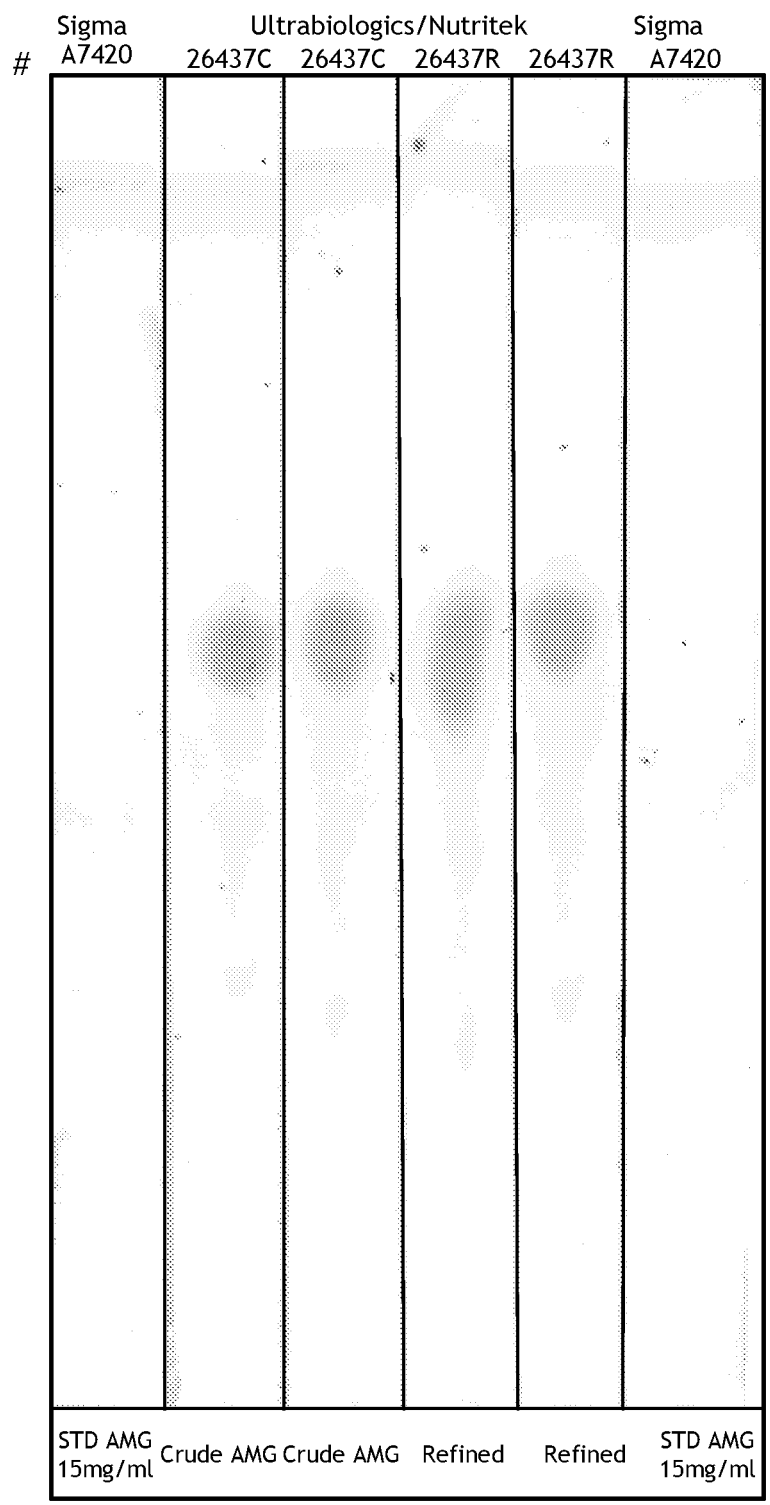
FIG. 4: Repeat thin-layer chromatography results for Ultrabiologic [Nutritek®] amyloglucosidase samples 26437C (crude) in solution and 26437R (refined) in citrate buffer (pH 4.5). Refined samples (15 mg/mL) were filtered and concentrated as per SOP. HPLC grade AMG (Sigma A7420 TLC is shown for comparison and is void of extraneous components. The importance of dialysis or come other purification technique (gel filtration) to remove residual biological substances is considered.
Figure 5:
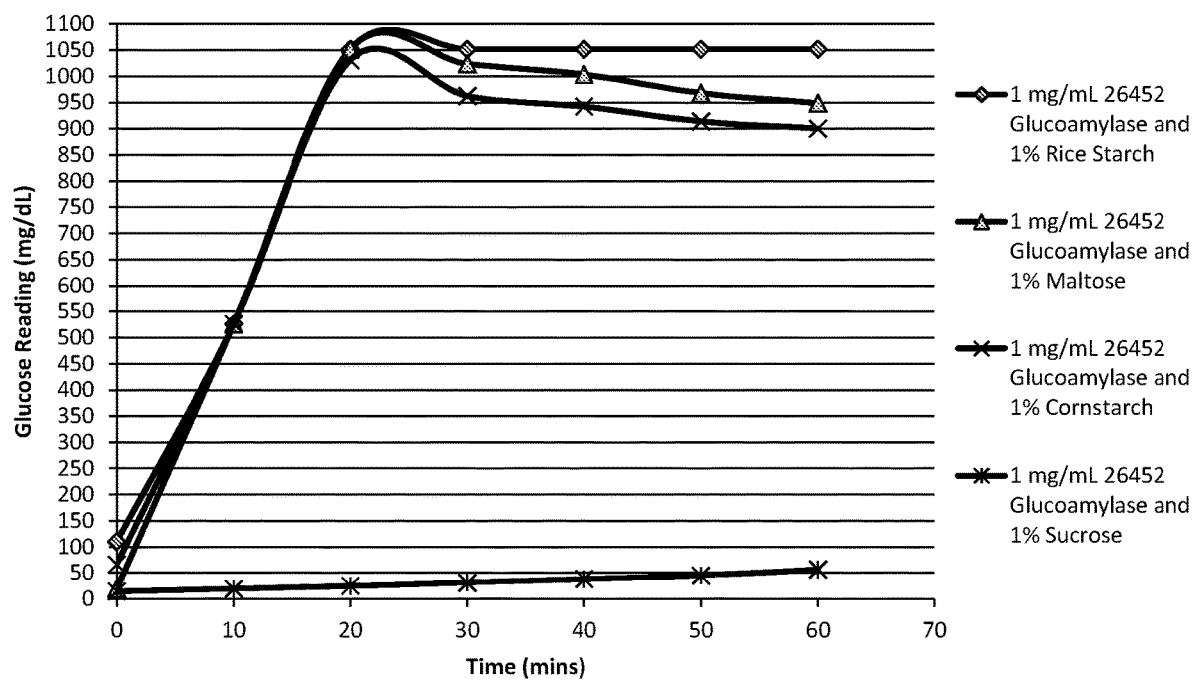
FIG. 5: A glucoamylase enzyme activity assay using a variety of substrates.
Figure 6:
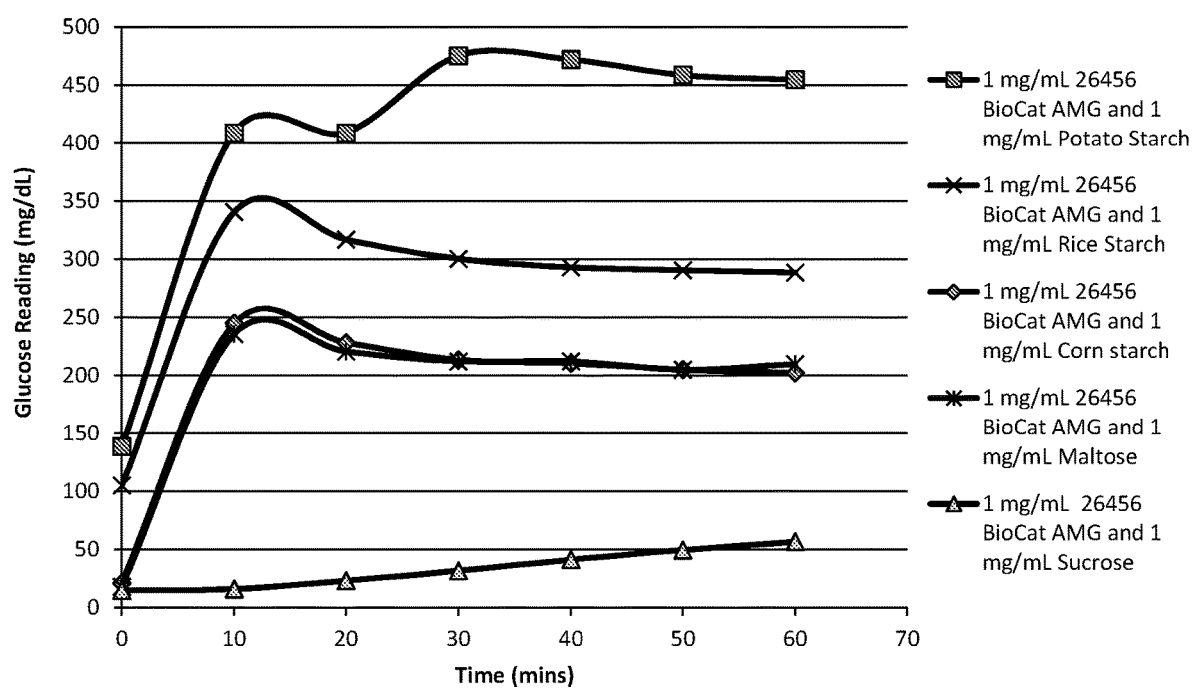
FIG. 6: A BioCat AMG dialyzed enzyme activity assay with a variety of substrates.
Figure 7:
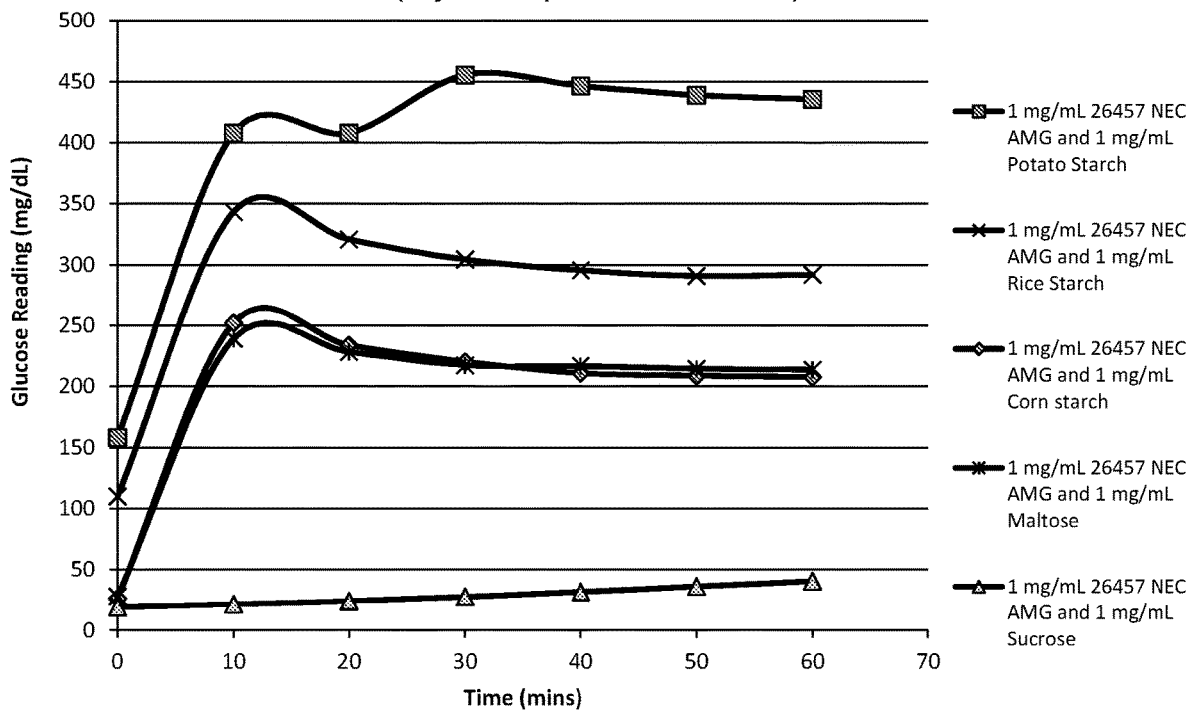
FIG. 7: A NEC AMG dialyzed enzyme activity assay using a variety of substrates.
Figure 8:
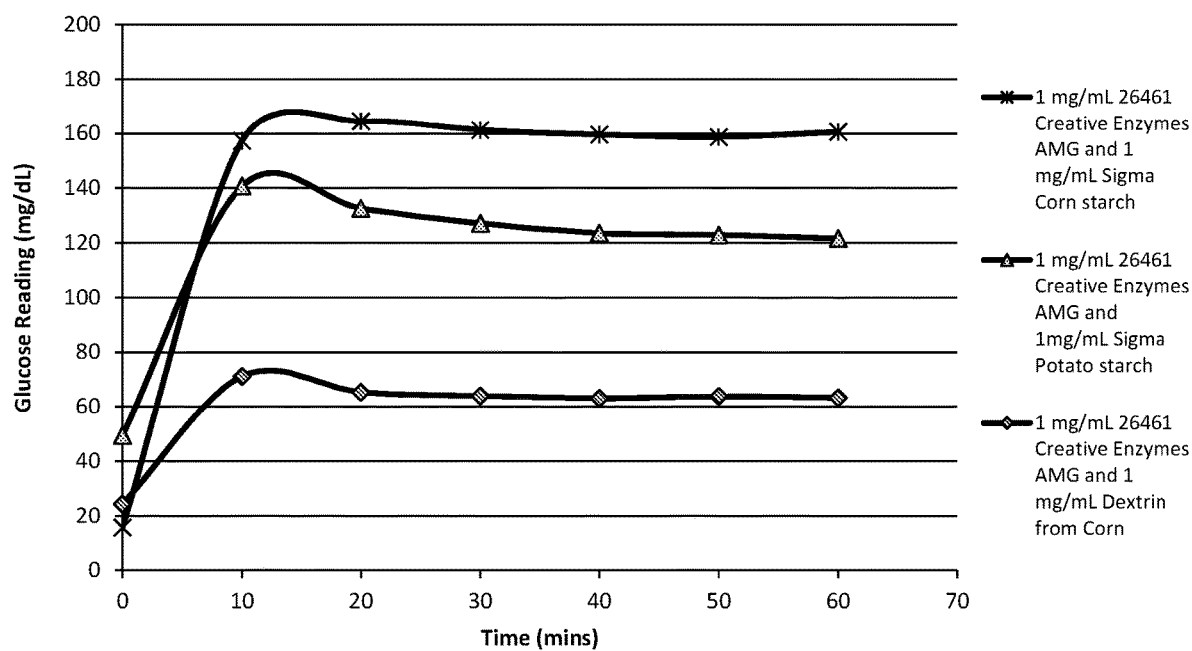
FIG. 8: A Creative Enzymes AMG dialyzed enzyme activity assay using a variety of substrates.

Thin layer chromatography (TLC) is a useful technique for the separation and identification of compounds in mixtures. TLC is used routinely to follow the progress of reactions by monitoring the consumption of starting materials and observing for the appearance of products. Commercial applications of TLC include the analysis of aberrant substances to establish purity or identity of the components, and analysis of foods to determine the presence of other compounds such as flavonoids, pesticides and possibly contaminants including sesquiterpenoid trichothecenes (Eppley at al., 1984). See FIGS. 3-4.

Estimation of Enzyme Activity by Rate of Glucose Production

One approach to the determination of enzyme activity is to estimate the rate of glucose production from observations made on a controlled substrate reaction between enzymes and oligosaccharides (dextrins) or starches. The assessment of glucose production involves the use of test or HPLC-grade reference enzymes to hydrolyze oligosaccharides or starches, and indirect measurements of resultant free glucose can be done. The traditional technical approach relies upon a glucose oxidation reaction that ultimately yields a reactive species that effects a colorimetric change that, in turn, correlates with glucose concentration when compared with standards and control reagents. A contemporary approach relies upon a change in oxygen ion concentration that correlates with glucose concentration. In the later scenario, oxygen consumption during glucose oxidation is detected by use of a Clark-type amperometric, platinum oxygen electrode. This is the same highly accurate method upon which blood gas analyzers are based. Other glucose assays rely upon sample hydrolysis of p-nitrophenyl-α-glucopyraniside (PNGP; C12H15NO8; Molecular Weight 301.25) to p-nitrophenol (PNGP) and glucose and colorimetric measurement of PNGP at pH 4.3 and 50° C. The electrochemical (oxygen consumption) measurement of glucose production closely equates to p-nitrophenyl since the molecule is hydrolyzed in a 1:1 ratio. The electrochemical technology used in these experiments is exceptionally fast, with results available in less than 20 seconds after sample injection. This timely approach prevents overestimation of enzyme activity and is remarkably free from the interference problems associated with antiquated PNGP optical techniques. As such, test enzymes, for which activity is undetermined, can be assayed using these semi-micro quantitative analyses. The work described herein relates to the quality (activity) of the particular food-grade, fungal-derived enzymes, such as amyloglucosidase produced by molecular biology or microbial culture, to release glucose from target starch or oligosaccharide substrates in the human alimentary tract.

Amyloglucosidase has broader activity than mammalian physiological enzymes, and alpha amylase is not needed to liberate glucose from starch. Amyloglucosidase is a robust candidate therapeutic agent and is probably active in the stomach, especially when food ingestion, taken concomitantly, raises pH. Invertase, an enzyme used to hydrolyzed sucrose, may be assayed in a similar way. Several candidate digestive enzyme samples (amyloglucosidase or invertase) were tested. The amount of enzyme was adjusted based upon determined protein concentrations unless otherwise specified. Test conditions included use of 10 mM citrate buffer at pH 4.5 and 37 C. Results are reported regarding milligrams glucose produced periodically (over 60 minutes) and converted to USP activity units consistent with USP Dietary Supplements Compendium, (the United States Pharmacopoeia Convention, Inc., Rockville, Md., USP/DSC 2nd ed., 2012) Appendix V, Enzyme Assays pg. 1727-1759. One unit of glucoamylase activity is defined as the amount of glucoamylase that will hydrolyze 0.1 μmol/min of maltose under the conditions of the assay (same as produce 0.2 μmol/min of glucose). Note: in summary, the calculations rely on the peak delta milligrams glucose produced per minute, which is usually the first 20 minutes of the assay. The minute-mean is determined and milligrams are converted to micromoles. The AMG activity is expressed as International Units (IU) per milligram enzyme. HPLC-grade analytical enzymes were used for comparative purposes.

TABLE 1

Enzyme Activity: Data Summary

| Accession # | Enzyme Name | Supplier | Activity (Qual) | Comments |
|---|---|---|---|---|
| 26424B & 26437 | Amyloglucosidase | Ultrabiologics | Excellent~0.5 AGU/15 mg protein | Powder |
| 26452 | Glucoamylase | NEC | Excellent~0.5 AGU/15 mg protein | Powder |
| 26454 | Amyloglucosidase | Creative Biomart | Not Performed | Protein Minimal |
| 26456 | Amyloglucosidase | Bio-Cat | Poor | Powder |
| 26457 | Glucoamylase | NEC | Fair | Powder Excellent |
| 26461 | Amyloglucosidase | Creative Enzymes | Fair | Black liquid |

TABLE 2

Enzyme Activity (see FIGS. 5-8 for the following tables)

| Reaction Vial # | | 0 | 10 | 20 | 30 | 40 | 50 | 60 | end |
|---|---|---|---|---|---|---|---|---|---|
| | Sample: NEC GLUCOAMYLASE 26452 | | | | | | | | |
| 1 | 1 mg/mL 26452 Glucoamylase control, no substrate | 7.6 | ND | ND | ND | ND | ND | ND | 11.6 |
| 2 | 1 mg/mL 26452 Glucoamylase and 1% Maltose | 19.5 | 526.0 | 1052.0 | 1023.6 | 1003.6 | 967.8 | 948.8 | ND |
| 3 | 1 mg/mL 26452 Glucoamylase and 1% Sucrose | 14.8 | 19.7 | 25.2 | 31.2 | 38.5 | 45.0 | 56.6 | ND |
| 4 | 1 mg/mL 26452 Glucoamylase and 1% Rice Starch | 110.3 | 526.0 | 1052.0 | 1052.0 | 1052.0 | 1052.0 | 1052.0 | ND |
| 5 | 1 mg/mL 26452 Glucoamylase and 1% Cornstarch | 66.4 | 526.0 | 1031.0 | 962.4 | 942.4 | 913.8 | 900.2 | ND |
| 6 | 1% Maltose control, no enzyme | 4.0 | ND | ND | ND | ND | ND | ND | 10.3 |
| 7 | 1% Sucrose control, no enzyme | 5.0 | ND | ND | ND | ND | ND | ND | 7.8 |
| 8 | 1% Rice Starch control, no enzyme | 8.1 | ND | ND | ND | ND | ND | ND | 13.2 |
| 9 | 1% Cornstarch control; no enzyme | 0.9 | ND | ND | ND | ND | ND | ND | 1.9 |
| 10 | 25 mg/dL Glucose standard | 23.1 | ND | ND | ND | ND | ND | ND | 22.7 |
| 11 | 100 mg/dL Glucose Standard | 97.0 | ND | ND | ND | ND | ND | ND | 94.3 |

TABLE 2-continued

Enzyme Activity (see FIGS. 5-8 for the following tables)

| Reaction Vial # | | 0 | 10 | 20 | 30 | 40 | 50 | 60 | end |
|---|---|---|---|---|---|---|---|---|---|
| 12 | 250 mg/dL Glucose Standard | 249.2 | ND | ND | ND | ND | ND | ND | 247.9 |
| 13 | 400 mg/dL Glucose Standard | 397.7 | ND | ND | ND | ND | ND | ND | 394.0 |
| | Sample: Bio-Cat Amyloglucosidase 26456 | | | | | | | | |
| 1 | 1 mg/mL AMG, no substrate | 10.2 | ND | ND | ND | ND | ND | ND | 13.3 |
| 2 | 1 mg/mL AMG, 1 mg/mL sucrose | 14.6 | 15.9 | 23.1 | 31.5 | 41.3 | 49.4 | 56.6 | ND |
| 3 | 1 mg/mL AMG, 1 mg/mL maltose | 17.8 | 235.7 | 220.6 | 212.1 | 212.2 | 204.9 | 209.8 | ND |
| 4 | 1 mg/mL AMG and 1 mg/mL corn starch | 21.1 | 244.9 | 228.2 | 213.4 | 210.5 | 205.0 | 202.2 | ND |
| 5 | 1 mg/mL AMG and 1 mg/mL rice Starch | 104.9 | 340.5 | 316.9 | 300.2 | 293.1 | 290.4 | 288.6 | ND |
| 6 | 1 mg/mL AMG and 1 mg/mL potato starch | 138.5 | 409.0 | 409.0 | 475.6 | 472.2 | 458.8 | 454.8 | ND |
| 7 | 1 mg/mL Sucrose control, no enzyme | 10.3 | ND | ND | ND | ND | ND | ND | 1.1 |
| 8 | 1 mg/mL Maltose, no enzyme | 2.1 | ND | ND | ND | ND | ND | ND | 2.5 |
| 9 | 1 mg/mL corn Starch, no enzyme | 1.1 | ND | ND | ND | ND | ND | ND | 2.1 |
| 10 | 1 mg/mL rice starch, no enzyme | 4.4 | ND | ND | ND | ND | ND | ND | 5.8 |
| 11 | 1 mg/mL potato starch control, no enzyme | 1.6 | ND | ND | ND | ND | ND | ND | 2.1 |
| 12 | 25 mg/dL glucose standard | 21.9 | ND | ND | ND | ND | ND | ND | 22.4 |
| 13 | 100 mg/dL glucose standard | 96.2 | ND | ND | ND | ND | ND | ND | 96.3 |
| 14 | 400 mg/dL Glucose Standard | 379.9 | ND | ND | ND | ND | ND | ND | 387.5 |
| | Sample: NEC Amyloglucosidase 26457 | | | | | | | | |
| 1 | 1 mg/mL 26457 AMG control, no substrate | 24.3 | ND | ND | ND | ND | ND | ND | 20.7 |
| 2 | 1 mg/mL 26457 AMG and 1 mg/mL Sucrose | 19.0 | 21.3 | 24.0 | 27.5 | 31.6 | 36.0 | 40.4 | ND |
| 3 | 1 mg/mL 26457 AMG and 1 mg/mL Maltose | 27.9 | 239.1 | 228.3 | 217.3 | 216.8 | 214.5 | 213.5 | ND |
| 4 | 1 mg/mL 26457 AMG and 1 mg/mL Corn starch | 26.3 | 252.0 | 233.8 | 220.1 | 210.9 | 208.7 | 207.6 | ND |
| 5 | 1 mg/mL 26457 AMG and 1 mg/mL Rice Starch | 110.0 | 343.0 | 320.8 | 304.3 | 295.5 | 290.8 | 292.0 | ND |
| 6 | 1 mg/mL 26457 AMG and 1 mg/mL Potato Starch | 158.3 | 407.6 | 407.6 | 455.4 | 446.4 | 438.8 | 435.4 | ND |
| 7 | 1 mg/mL Sucrose control, no enzyme | 0.3 | ND | ND | ND | ND | ND | ND | 2.2 |
| 8 | 1 mg/mL Maltose control, no enzyme | 1.0 | ND | ND | ND | ND | ND | ND | 4.1 |
| 9 | 1 mg/mL Corn Starch control, no enzyme | 1.3 | ND | ND | ND | ND | ND | ND | 3.7 |
| 10 | 1 mg/mL Rice starch control, no enzyme | 4.6 | ND | ND | ND | ND | ND | ND | 6.4 |
| 11 | 1 mg/mL Potato starch control, no enzyme | 2.7 | ND | ND | ND | ND | ND | ND | 3.2 |
| 12 | 25 mg/dL Glucose standard | 24.2 | ND | ND | ND | ND | ND | ND | 22.6 |

TABLE 2-continued

Enzyme Activity (see FIGS. 5-8 for the following tables)

| Reaction Vial # | | 0 | 10 | 20 | 30 | 40 | 50 | 60 | end |
|---|---|---|---|---|---|---|---|---|---|
| 13 | 100 mg/dL Glucose Standard | 95.2 | ND | ND. | ND | ND | ND | ND | 95.6 |
| 14 | 250 mg/dL Glucose Standard | 243.1 | ND | ND | ND | ND | ND | ND | 249.3 |
| 15 | 400 mg/dL Glucose Standard | 395.5 | ND | ND | ND | ND | ND | ND | 397.5 |
| | Sample: Creative Enzymes Amyloglucosidase 26461 | | | | | | | | |
| 1 | 1 mg/mL 26461 AMG control, no substrate | 0.1 | ND | ND | ND | ND | ND | ND | 0.1 |
| 2 | 1 mg/mL 26461 AMG and 1 mg/mL Sidma Potato starch | 49.4 | 140.7 | 132.6 | 127.1 | 123.5 | 122.9 | 121.5 | ND |
| 3 | 1 mg/mL 26461 AMG and 1 mg/mL Sigma Corn starch | 15.7 | 157.3 | 164.5 | 161.3 | 159.6 | 158.7 | 160.6 | ND |
| 4 | 1 mg/mL 26461 AMG and 1 mg/mL Dextrin from Corn | 24.3 | 71.2 | 65.4 | 64.0 | 63.1 | 63.8 | 63.3 | ND |
| 5 | 1 mg/mL Sigma Potato Starch control, no enzyme | 6.5 | ND | ND | ND | ND | ND | ND | ND |
| 6 | 1 mg/mL Sigma Corn Starch control, no enzyme | 1.9 | ND | ND | ND | ND | ND | ND | 4.6 |
| 7 | 1 mg/mL Dextrin from corn control; no enzyme | 1.6 | ND | ND | ND | ND | ND | ND | 3.5 |
| 8 | 25 mg/dL Glucose standard | 22.0 | ND | ND | ND | ND | ND | ND | 22.8 |
| 9 | 100 mg/dL Glucose Standard | 94.4 | ND | ND | ND | ND | ND | ND | 94.6 |
| 10 | 250 mg/dL Glucose Standard | 242.5 | ND | ND | ND | ND | ND | ND | 241.9 |
| 11 | 400 mg/dL Glucose Standard | 390.2 | ND | ND | ND | ND | ND | ND | 392.1 |

Example 2

Processed Ultrabiologic Amyloglucosidase (AMG)/Sorghum Starch Activity Experiment. 31 Jul. 2017 Aro/Ma Goal: To compare between AMG activity after purifying and concentrating (decrease volume 50%) suspension prepared under new ethanol extraction protocol, described elsewhere herein, and 500 mg AMG capsules activity, 1 ml of the AMG suspension mentioned above to 500 mg of excipient B, (Calcium phosphate 10 g, Calcium silicate 10 g, Calcium Carbonate 80 g).

Given: AMW of glucose is 180.156 Daltons and 1 mg=0.0055 mmol

1 AGU (of AMG) unit activity=0.2 mol glucose released/minute (0.1 µmol maltose equivalent (starch) hydrolyzed)

Methods Summary: Mix 75 grams crude Ultrabiologic amyloglucosidase powder (Lot #5220511016, Exp 2.2016, BCM #700126437b) in milliQ water (qs to 250 mL). Mix well using blender (45'), then spin out crude matter, coarse and fine vacuum filter (Whatman #1, and Millipore 0.45 µM with Whatman 42 pre-filter), and spin concentrate to 50% volume using Millipore Centriprep 30K MWCO. Aliquot for assay of resultant light brown suspension. Test for absence of deoxynivalenol (Don-V) toxin.

Figure 9:
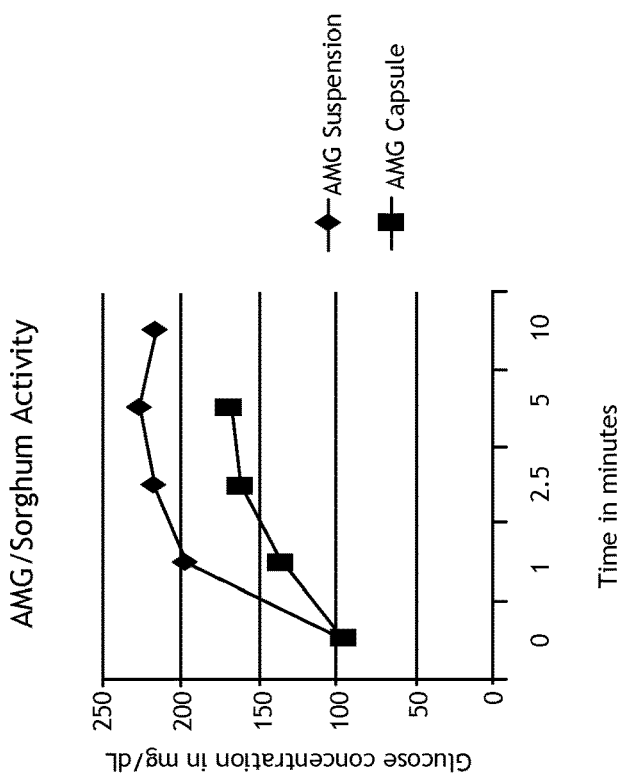
FIG. 9: Production comparison of processed Ultrabiologic® material when hydrolyzing sorghum compared to AMG capsule when hydrolyzing sorghum.

Timed Assay (FIG. 9):

A) 1.00 mL AMG: 99.00 mL Sorghum (20 mg/mL) to deliver 5.0 µL to Analox GM9 glucometer. Measure and record starting glucose concentration (mg/dL) and during 1, 2.5, 5 and 10 minute elapsed reaction time.

B) 1 AMG capsule: 99.00 mL Sorghum (20 mg/mL) to deliver 5.0 µL to Analox GM9 glucometer. Measure and record starting glucose concentration (mg/dL) and during 1, 2.5, 5 and 10 minute elapsed reaction time.

Data: Don-V toxin NEGATIVE

A) For 1 ml AMG suspension:
Δ Glucose increase at 1 minute=+102.9 mg/dL
Δ Glucose increase at 2.5 minutes=+122.0 mg/dL
Δ Glucose increase at 5 minutes=+131.7 mg/dL
Δ Glucose increase at 10 minutes=+121.7 mg/dL B) For 1 AMG Capsule:
Δ Glucose increase at 1 minute=+40.9 mg/dL
Δ Glucose increase at 2.5 minutes=+66.4 mg/dL
Δ Glucose increase at 5 minutes=+73.6 mg/dL
Δ Glucose increase at 10 minutes=error reported Calculations: A) For AMG suspension:

Mean 1 minute Δ Glucose increase at 5 minutes+26.34 mg/dL equivalent for +263.4 mg/L 1 mL AMG liberated+263.4 mg/min for 1.463 mmol/min 1.463 mmol×1000=1463 μmol Conversion of μmol to AGU: 1463 μmol glucose/0.2 (for maltose equivalents)/0.1=7315 AGU B) For AMG Capsule:

MEAN 1 minute Δ glucose increase at 5 minutes+14.72 mg/dL equivalent for +147.2 mg/L 1 mL AMG liberated+147.2 mg/min for 0.8096 mmol/min 0.8096 mmol×1000=809.6 μmol Conversion of μmol to AGU: 809.6 μmol glucose/0.2 (for maltose equivalents)/0.1=4048 AGU Discussion: 1 mL processed AMG suspension has enzyme activity of 7315 AGU when hydrolyzing Sorghum starch. While AMG capsule (PRODUCT) has enzyme activity of 4048 AGU when hydrolyzing Sorghum starch.

Conclusion: 1 round of concentration in specific embodiments is sufficient since 1 mL of PRODUCT will be absorbed to 500 mg excipient and dried providing 4048 AGU per capsule. There was a 45% loss in AMG activity on Sorghum starch upon encapsulating with type B calcium excipient.

Example 3

Processed Ultrabiologic Amyloglucosidase (AMG)/Rice Starch Activity Experiment. 31 Jul. 2017 ARO/MA Goal: To compare between AMG activity after purifying and concentrating (decrease volume 50%) suspension prepared under new protocol, described elsewhere, and 500 mg AMG capsules activity, 1 ml of the AMG suspension mentioned above to 500 mg of excipient B, (Calcium phosphate 10 g, Calcium silicate 10 g, Calcium Carbonate 80 g).

Given: AMW of glucose is 180.156 Daltons and 1 mg=0.0055 mmol

1 AGU (of AMG) unit activity=0.2 μmol glucose released/minute (0.1 μmol maltose equivalent (starch) hydrolyzed)

Methods Summary: Mix 75 grams crude Ultrabiologic amyloglucosidase powder (Lot #5220511016, Exp 2.2016, BCM #700126437b) in milliQ water (qs to 250 mL). Mix well using blender (45'), then spin out crude matter, coarse and fine vacuum filter (Whatman #1, and Millipore 0.45 μM with Whatman 42 pre-filter), and spin concentrate to 50% volume using Millipore Centriprep 30K MWCO. Aliquot for assay of resultant light brown suspension. Test for absence of deoxynivalenol (Don-V) toxin.

Timed Assay (FIG. 10):

A) 1.00 mL AMG: 99.00 mL Rice starch (20 mg/mL) to deliver 5.0 μL to Analox GM9 glucometer. Measure and record starting glucose concentration (mg/dL) and during 1, 2.5, 5 and 10 minute elapsed reaction time.

B) 1 AMG capsule: 99.00 mL Rice starch (20 mg/mL) to deliver 5.0 μL to Analox GM9 glucometer. Measure and record starting glucose concentration (mg/dL) and during 1, 2.5, 5 and 10 minute elapsed reaction time.

Data: Don-V toxin NEGATIVE

A) For 1 ml AMG suspension:

Δ Glucose increase at 1 minute=+84.9 mg/dL

Δ Glucose increase at 2.5 minutes=+89.7 mg/dL

Δ Glucose increase at 5 minutes=+123 mg/dL

Δ Glucose increase at 10 minutes=+143 mg/dL

B) For 1 AMG Capsule:

Δ Glucose increase at 1 minute=+48.5 mg/dL

Δ Glucose increase at 2.5 minutes=+69.9 mg/dL

Δ Glucose increase at 5 minutes=+78.7 mg/dL

Δ Glucose increase at 10 minutes=+81.6 mg/dL

Calculations: A) For AMG suspension:

Mean 1 minute Δ Glucose increase at 5 minutes+24.58 mg/dL equivalent for +245.8 mg/L 1 mL AMG liberated+245.8 mg/min for 1.3519 mmol/min 1.3519 mmol×1000=1351.9 μmol Conversion of μmol to AGU: 1351.9 μmol glucose/0.2 (for maltose equivalents)/0.1=6759 AGU B) For AMG Capsule:

MEAN 1 minute Δ glucose increase at 5 minutes+15.75 mg/dL equivalent for +157.5 mg/L 1 mL AMG liberated+157.5 mg/min for 0.8741 mmol/min 0.8741 mmol×1000=874.1 μmol Conversion of μmol to AGU: 874.1 μmol glucose/0.2 (for maltose equivalents)/0.1=4370 AGU Discussion: 1 mL processed AMG suspension has enzyme activity of 6759 AGU when hydrolyzing Sorghum starch. While AMG capsule (PRODUCT) has enzyme activity of 4370 AGU when hydrolyzing Sorghum starch.

Conclusion: 1 round of concentration in specific embodiments is sufficient since 1 mL of PRODUCT will be absorbed to 500 mg excipient and dried providing 4370 AGU per capsule. There was a 35% loss in AMG activity on rice starch upon encapsulating with type B calcium excipient.

Example 4

Processed Ultrabiologic Amyloglucosidase (AMG)/Wheat Starch Activity Experiment. 31 Jul. 2017 ARO/MA Goal: To compare between AMG activity after purifying and concentrating (decrease volume 50%) suspension prepared under new protocol, described elsewhere, and 500 mg AMG capsules activity, 1 ml of the AMG suspension mentioned above to 500 mg of excipient B, (Calcium phosphate 10 g, Calcium silicate 10 g, Calcium Carbonate 80 g).

Given: AMW of glucose is 180.156 Daltons and 1 mg=0.0055 mmol

1 AGU (of AMG) unit activity=0.2 μmol glucose released/minute (0.1 μmol maltose equivalent (starch) hydrolyzed)

Methods Summary: Mix 75 grams crude Ultrabiologic amyloglucosidase powder (Lot #5220511016, Exp 2.2016, BCM #700126437b) in milliQ water (qs to 250 mL). Mix well using blender (45'), then spin out crude matter, coarse and fine vacuum filter (Whatman #1, and Millipore 0.45 μM with Whatman 42 pre-filter), and spin concentrate to 50% volume using Millipore Centriprep 30K MWCO. Aliquot for assay of resultant light brown suspension. Test for absence of deoxynivalenol (Don-V) toxin.

Figure 11:
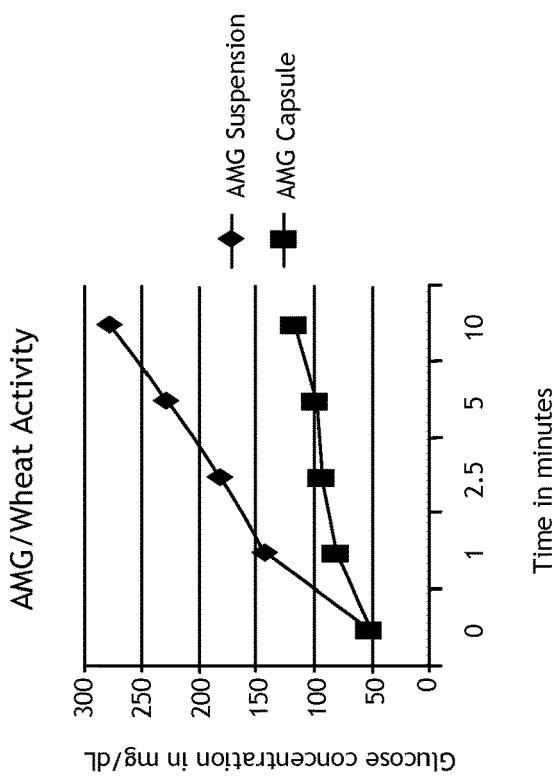
FIG. 11: Production comparison of processed Ultrabiologic® material when hydrolyzing wheat compared to AMG capsule when hydrolyzing wheat.

Timed Assay (FIG. 11):

A) 1.00 mL AMG: 99.00 mL Wheat starch (20 mg/mL) to deliver 5.0 μL to Analox GM9 glucometer. Measure and record starting glucose concentration (mg/dL) and during 1, 2.5, 5 and 10 minute elapsed reaction time.

B) 1 AMG capsule: 99.00 mL Wheat starch (20 mg/mL) to deliver 5.0 μL to Analox GM9 glucometer. Measure and record starting glucose concentration (mg/dL) and during 1, 2.5, 5 and 10 minute elapsed reaction time.

Data: Don-V toxin NEGATIVE
A) For 1 ml AMG suspension:
Δ Glucose increase at 1 minute=+91.50 mg/dL
Δ Glucose increase at 2.5 minutes=+130.6 mg/dL
Δ Glucose increase at 5 minutes=+177.2 mg/dL
Δ Glucose increase at 10 minutes=+226.0 mg/dL
B) For 1 AMG Capsule:
Δ Glucose increase at 1 minute=+28.2 mg/dL
Δ Glucose increase at 2.5 minutes=+41.1 mg/dL
Δ Glucose increase at 5 minutes=+48.1 mg/dL
Δ Glucose increase at 10 minutes=+65.3 mg/dL
Calculations: A) For AMG suspension:
Mean 1 minute Δ Glucose increase at 5 minutes+35.44 mg/dL equivalent for +354.4 mg/L
1 mL AMG liberated+354.4 mg/min for 1.9492 mmol/min
1.9492 mmol×1000=1949.2 μmol
Conversion of μmol to AGU: 1949.2 μmol glucose/0.2 (for maltose equivalents)/0.1=9746 AGU B) For AMG Capsule:
MEAN 1 minute Δ glucose increase at 5 minutes+9.62 mg/dL equivalent for +96.2 mg/L
1 mL AMG liberated+96.2 mg/min for 0.5291 mmol/min
0.5291 mmol×1000=529.1 μmol
Conversion of μmol to AGU: 529.1 μmol glucose/0.2 (for maltose equivalents)/0.1=2645 AGU Discussion: 1 mL processed AMG suspension has enzyme activity of 9746 AGU when hydrolyzing Sorghum starch. While AMG capsule (PRODUCT) has enzyme activity of 2645 AGU when hydrolyzing Sorghum starch.

Conclusion: 1 round of concentration in specific embodiments is sufficient since 1 mL of PRODUCT will be absorbed to 500 mg excipient and dried providing 2645 AGU per capsule. There was a 73% loss in AMG activity upon encapsulating with type B calcium excipient.

Example 5

Processed Ultrabiologic Amyloglucosidase (AMG)/Maize Starch Activity Experiment

Goal: To compare between AMG activity after purifying and concentrating (decrease volume 50%) suspension prepared under new protocol, described elsewhere, and 500 mg AMG capsules activity, 1 ml of the AMG suspension mentioned above to 500 mg of excipient B, (Calcium phosphate 10 g, Calcium silicate 10 g, Calcium Carbonate 80 g).

Given: AMW of glucose is 180.156 Daltons and 1 mg=0.0055 mmol

1 AGU (of AMG) unit activity=0.2 μmol glucose released/minute (0.1 μmol maltose equivalent (starch) hydrolyzed)

Methods Summary: Mix 75 grams crude Ultrabiologic amyloglucosidase powder (Lot #5220511016, Exp 2.2016, BCM #700126437b) in milliQ water (qs to 250 mL). Mix well using blender (45'), then spin out crude matter, coarse and fine vacuum filter (Whatman #1, and Millipore 0.45 μM with Whatman 42 pre-filter), and spin concentrate to 50% volume using Millipore Centriprep 30K MWCO. Aliquot for assay of resultant light brown suspension. Test for absence of deoxynivalenol (Don-V) toxin.

Timed Assay (FIG. 12):

A) 1.00 mL AMG: 99.00 mL Maize (20 mg/mL) to deliver 5.0 μL to Analox GM9 glucometer. Measure and record starting glucose concentration (mg/dL) and during 1, 5 and 10 minute elapsed reaction time.

B) 1 AMG capsule: 99.00 mL Maize (20 mg/mL) to deliver 5.0 μL to Analox GM9 glucometer. Measure and record starting glucose concentration (mg/dL) and during 1, 2.5, 5 and 10 minute elapsed reaction time.

Data: Don-V toxin NEGATIVE
A) For 1 ml AMG suspension:
Δ Glucose increase at 1 minute=+227.4 mg/dL
Δ Glucose increase at 5 minutes=+510.3 mg/dL
Δ Glucose increase at 10 minutes=+530.9 mg/dL
B) For 1 AMG Capsule:
Δ Glucose increase at 1 minute=+136.9 mg/dL
Δ Glucose increase at 5 minutes=+307.7 mg/dL
Δ Glucose increase at 10 minutes=+383.3 mg/dL
Calculations: A) For AMG suspension:
Mean 1 minute Δ Glucose increase at 5 minutes+102.06 mg/dL equivalent for +1020.6 mg/L
1 mL AMG liberated+1020.6 mg/min for 5.664 mmol/min
5.664 mmol×1000=5664 μmol
Conversion of μmol to AGU: 5664 μmol glucose/0.2 (for maltose equivalents)/0.1=28321 AGU B) For AMG Capsule:
MEAN 1 minute Δ glucose increase at 5 minutes+61.54 mg/dL-equivalent for +615.4 mg/L
1 mL AMG liberated+615.4 mg/min for 3.4154 mmol/min
3.4154 mmol×1000=3415.4 μmol
Conversion of μmol to AGU: 3415.4 μmol glucose/0.2 (for maltose equivalents)/0.1=17077 AGU Discussion: 1 mL processed AMG suspension has enzyme activity of 28321 AGU when hydrolyzing Sorghum starch. While AMG capsule (PRODUCT) has enzyme activity of 17077 AGU when hydrolyzing Sorghum starch.

Conclusion: 1 round of concentration in specific embodiments is sufficient since 1 mL of PRODUCT will be absorbed to 500 mg excipient and dried providing 17077 AGU per capsule. There was a 40% loss in AMG activity on maize starch upon encapsulating with type B calcium excipient.

Example 6

Processed Ultrabiologic Amyloglucosidase (AMG)/Millet Starch Activity Experiment. 31 Jul. 2017 ARO/MA Goal: To compare between AMG activity after purifying and concentrating (decrease volume 50%) suspension prepared under new protocol, described elsewhere, and 500 mg AMG capsules activity, 1 ml of the AMG suspension mentioned above to 500 mg of excipient B, (Calcium phosphate 10 g, Calcium silicate 10 g, Calcium Carbonate 80 g).

Given: AMW of glucose is 180.156 Daltons and 1 mg=0.0055 mmol

1 AGU (of AMG) unit activity=0.2 mol glucose released/minute (0.1 μmol maltose equivalent (starch) hydrolyzed)

Methods Summary: Mix 75 grams crude Ultrabiologic amyloglucosidase powder (Lot #5220511016, Exp 2.2016, BCM #700126437b) in milliQ water (qs to 250 mL). Mix well using blender (45'), then spin out crude matter, coarse and fine vacuum filter (Whatman #1, and Millipore 0.45 μM with Whatman 42 pre-filter), and spin concentrate to 50% volume using Millipore Centriprep 30K MWCO. Aliquot for assay of resultant light brown suspension. Test for absence of deoxynivalenol (Don-V) toxin.

Figure 13:
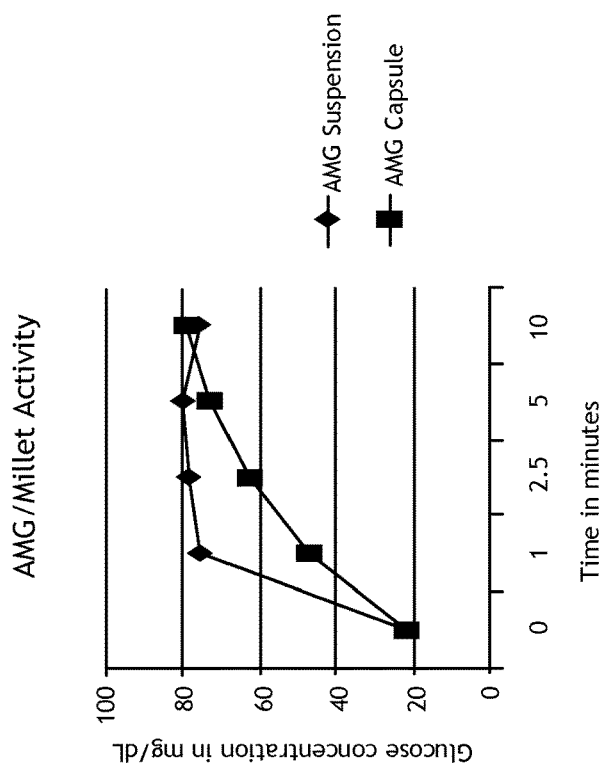
FIG. 13: Production comparison of processed Ultrabiologic® material when hydrolyzing millet compared to AMG capsule when hydrolyzing millet.
Figure 14:
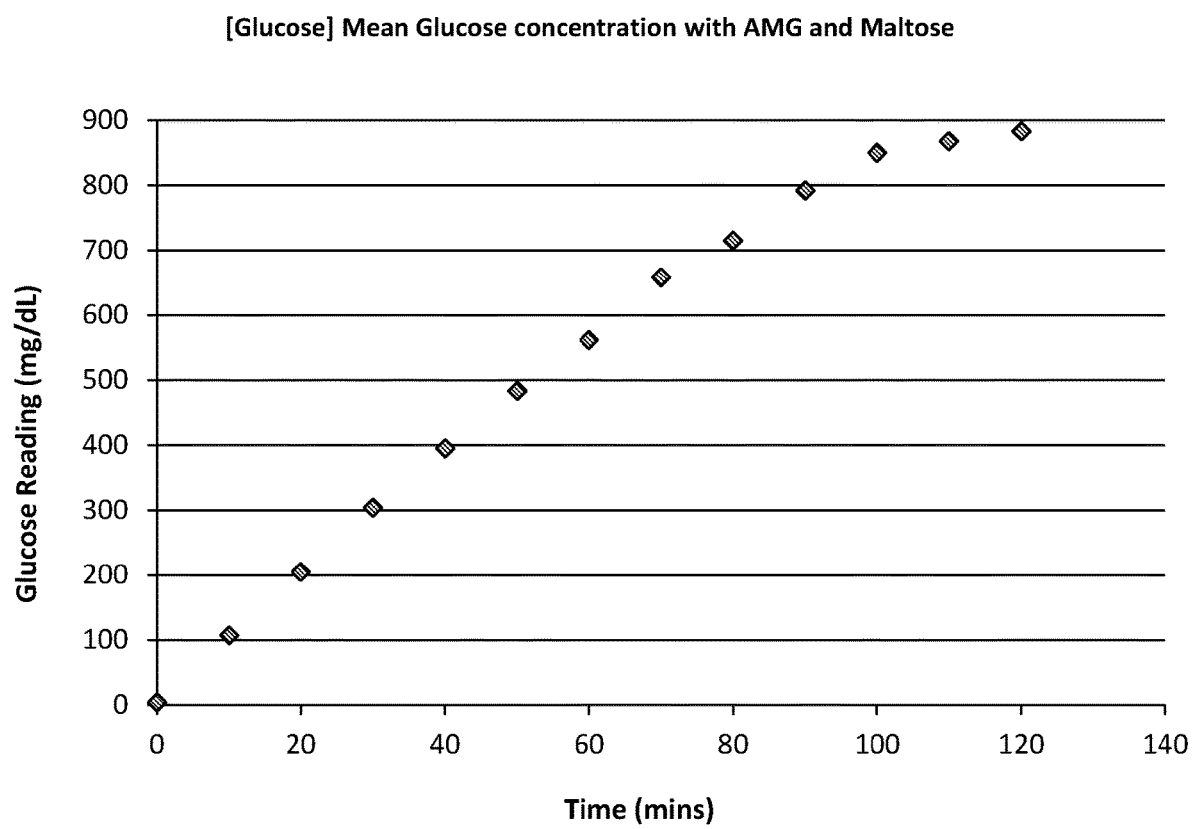
FIG. 14: Mean Glucose Concentration with AMG and Maltose.

Timed Assay (FIG. 13):

A) 1.00 mL AMG: 99.00 mL Millet starch (20 mg/mL) to deliver 5.0 µL to Analox GM9 glucometer. Measure and record starting glucose concentration (mg/dL) and during 1, 2.5, 5 and 10 minute elapsed reaction time.

B) 1 AMG capsule: 99.00 mL Millet starch (20 mg/mL) to deliver 5.0 µL to Analox GM9 glucometer. Measure and record starting glucose concentration (mg/dL) and during 1, 2.5, 5 and 10 minute elapsed reaction time.

Data: Don-V toxin NEGATIVE

A) For 1 ml AMG suspension:

Δ Glucose increase at 1 minute=+55.1 mg/dL
Δ Glucose increase at 2.5 minutes=+58.0 mg/dL
Δ Glucose increase at 5 minutes=+59.0 mg/dL
Δ Glucose increase at 10 minutes=+56.5 mg/dL B) For 1 AMG Capsule:

Δ Glucose increase at 1 minute=+25.2 mg/dL
Δ Glucose increase at 2.5 minutes=+41.3 mg/dL
Δ Glucose increase at 5 minutes=+51.8 mg/dL
Δ Glucose increase at 10 minutes=+57.5 mg/dL Calculations: A) For AMG suspension:

Mean 1 minute Δ Glucose increase at 5 minutes+11.8 mg/dL equivalent for +118 mg/L 1 mL AMG liberated+118 mg/min for 0.6549 mmol/min 0.6549 mmol×1000=654.9 µmol Conversion of µmol to AGU: 654.9 µmol glucose/0.2 (for maltose equivalents)/0.1=3274 AGU B) For AMG Capsule:

MEAN 1 minute Δ glucose increase at 5 minutes+11.44 mg/dL equivalent for +114.4 mg/L 1 mL AMG liberated+114.4 mg/min for 0.6349 mmol/min 0.6349 mmol×1000=634.9 µmol Conversion of mol to AGU: 634.9 µmol glucose/0.2 (for maltose equivalents)/0.1=3174 AGU Discussion: 1 mL processed AMG suspension has enzyme activity of 3274 AGU when hydrolyzing Sorghum starch. While AMG capsule (PRODUCT) has enzyme activity of 3174 AGU when hydrolyzing Sorghum starch.

Conclusion: 1 round of concentration in specific embodiments is sufficient since 1 mL of PRODUCT will be absorbed to 500 mg excipient and dried providing 3174 AGU per capsule. There was a 4% loss in AMG activity on millet starch upon encapsulating with type B calcium excipient.

Example 7

Considerations

Several commercial and crude amyloglucosidase supplement products were tested and were found to significantly vary in quality. Most were insufficient in activity to be clinically useful and candidate for development would require enrichment by concentration with a goal of 1000 AGU or more per capsule, and it is conceivable that 10 k AGU might be required to observe a favorable clinical response.

The data presented herein are informative and two candidate amyloglucosidase preparations were identified for potential development into a medicinal food product or nutriceutical. The enzyme is heat stable and suitable for use in arid climates. AMG has a broad range of activity from pH 4-8 and is robust in trypsin and chymotrypsin; it would be useful as a nutriceutical or supplement to relieve symptoms of starch maldigestion. Furthermore, these products can be further processed as capsules to be used in the field to improve the nutritional availability of grains that are not calorically dense or difficult to digest due to recent marasmus-like illness.

Sample 26424B was useful because of high purity, high protein concentration and high enzymatic activity across all tested substrates. It was known from initial work performed under standard USP assay conditions on 1% maltose (KMH31OCT14: 46-49, that AMG sample 26424B has excellent activity compared to Sigma-Aldrich reference standard AMG (~41AGU per 15 mg. protein (~3 AGU/mg AMG). The inventor originally found an amyloglucosidase product that has an activity that approximates the predicted activity of 300 IU for pure HPLC-grade enzyme. Sample 26452 demonstrated activities of 286 IU for maltose, 262 IU for rice starch and 268 IU for corn starch. Crude product approximated 50 percent protein content, and SDS-PAGE demonstrated relatively pure protein bands (3) before and after dialysis at 50 KD MWCO and was consistent with expected product. Bands were identical to the Sigma HPLC reference grade amyloglucosidase (FIG. 1). Thin-layer chromatographic screening (FIG. 3) revealed typical residual LMW contaminants that should be easily removed by gradient gel filtration or dialysis during final processing.

In one embodiment, one can utilize amyloglucosidase, distributed by NEC, as a good choice for further development because it is readily available and met minimal specifications for activity and purity. The quality is rated as very good, overall, and in some embodiments is a good second choice for development if there was not a concern about the presence of deoxynivalenol (see FIG. 3, columns 5 & 6) and if the product could be reliably delivered in active form. In other cases the Canadian supplier (Ultrabiologics, LTD) claims to manufacture a crude amyloglucosidase product that exceeds 1000 AGU/gram of raw powder, but we found it to approximate ~3000-4000 AGU/gram raw powder with excipient.

In summary, in some cases one can utilize the methods of the disclosure on subjects with congenital sucrase isomaltase deficiency syndrome to determine if symptoms and 13C-strach breath test improved with treatment. This can be done under the existing BCM IRB Human Studies protocol, H-19253. If this is true, a field trial should be undertaken to determine if amyloglucosidase, a GRAS-listed food supplement, could improve the nutritional status of undernourished young children.

Example 8

Sampling Labeling and Determination of Protein Concentration by Lawry Method

Protein content of a sample may be determined by a colorimetric assay commonly known as the Lowry Procedure for Protein Assay [Lowry, O. H., N. J. Rosebrough, A. L. Farr and R. J. Randall, 1951. Protein measurement with the Folin-Phenol reagents. J. Biol. Chem. 193: 265-275]. The basic principle of the test relies on complete digestion and hydrolysis of protein, peptides and amino acids to produce urea. The intermediate, urea, is subsequently reduced with heat to form biuret (2-Imidodicarbonic diamide; $H_2NC(O)NHC(O)NH_2$) and alkaline ammonium ion that is free to react with cupric ion (Cu [II]) to produce a violet color, which is then measured colorimetrically and compared with standards to determine protein content. Under alkaline conditions (~pH 10) and the subsequent reduction of the Folin-Ciocalteay phosphomolybdicphosphotungstic acid to heteropolymolybdenum blue by the copper-catalyzed oxidation of aromatic acids [Dunn, M. J., 1992. Protein determination of total protein concentration. Harris, E. L. V., Angal, S., [Eds], Protein Purification Methods, Oxford: IRL Press]. The Lowry method is sensitive up to 2 mg of protein per mL. Price [1996. Proteins, Labfax, Oxford: Academic Press] notes that ammonium ions, zwitterionic buffers, nonionic buffers and thiol compounds may interfere with the reaction, and these compounds may need to be removed or diluted before performing the assays. Similar to Lowry reaction protein assay, kit is produced by BioRad as detergent compatible protein assay kits and is available that uses a colorimetric method to determine protein concentration following detergent solubilization. DC Protein assay kit catalog #500-0112 (Detergent-compatible colorimetric assay kit).

BioRad also produces a simple one step protein assay kit for measuring total protein concentration using a dye-binding method based on the Bradford assay which is based upon amino acid composition. Quick Start Bradford Protein assay Kit catalog #500-0202 can be adopted to use a microplate reader. However, many detergent and basic protein buffers interfere with the Bradford assay. Interference may be caused by chemical-protein or chemical dye interactions. The Bradford assay is based on an absorbance shift of the dye Coomassie Brilliant Blue G-250 in which, under acidic conditions, the red form of the dye is converted into its bluer form to bind to the protein being assayed. The bound form of the dye has an absorption spectrum maximum historically held to be at 595 nm. The cationic (unbound) forms are green or red. The binding of the dye to the protein stabilizes the blue anionic form. The increase of absorbance at 595 nm is proportional to the amount of bound dye, and thus to the amount (concentration) of protein present in the sample. (Bradford M. M. Anal. Biochem. 72: 248-254, 1976.) A major problem with this method is non-linearity over varying concentration ranges.)

Purpose

The purpose of this Standard Operating Procedure is to determine the total protein content in a provided candidate digestive enzyme sample.

Test Article Description and Risk Category

Description: a proteinaceous substance obtained from a GRAS-listed food product or supplement or non-pathogenic organism. NONHAZARDOUS and may be suitable for human consumption.

Frequency

Samples are prepared and analyzed on an As Needed basis when requested.

Materials and Reagents

Bio-Rad DC Protein Assay Kit (#500-0112); Detergent-compatible colorimetric assay kit contains: Reagent package (catalog number 500-0116) includes: 250 ml REAGENT A, an alkaline copper tartrate solution 2000 ml REAGENT B, a dilute Folin Reagent 5 ml REAGENT S (Sufficient for 500 standard assays or 10,000 microplate assays) The reagent package may be purchased as a kit with a bovine gamma globulin standard (kit catalog number 500-0111) or bovine serum albumin standard Roche Applied Bioscience Protease Inhibitor Cocktail Tablets 20 tablets individually packed in foil blister packs, each tablet is sufficient for a volume of 50 ml extraction solution (04693116001)

Procedure

Summary from Bio-Rad DC Protein Assay Kit

BioRad Quick Start BSA Standard Set (set of 7 BSA standards 0.125 mg/ml to 2 mg/ml).

Run triplicate determination for all samples. Preparation of working reagent; Add 20 µl of reagent S to each ml of reagent A that will be needed for the run; (This working reagent A' is stable for one week even though a precipitate will form after one day. If precipitate forms, warm the solution and vortex. Do not pipet the undissolved precipitate, as this will likely plug the tip of the pipet, thereby altering the volume of reagent that is added to the sample.). If samples do not contain detergent, step #1 may be omitted and simply use reagent A as supplied. Use 5 dilutions of a protein standards containing from 0.25 mg/mi to about 1.5 mg/ml protein. A standard curve should be prepared each time the assay is performed. For best results, the standards should always be prepared in the same buffer as the sample. Pipet 20 µl of standards and samples into clean, dry test tubes. Add 100 µl of reagent A' or A (see note from step 1) into each test tube. Vortex. Add 800 µl reagent B into each test tube and vortex immediately. After 15 minutes, absorbance can be read at 750 nm. The absorbance will be stable at least 1 hour. (See Troubleshooting Guide for recommendation on using a wavelength other than 750 nm.) One can use Excel software to plot standard curve to derive extrapolated protein concentration SAMPLING LABELING Upon arrival, samples are annotated with a unique numeric barcode beginning with 700126401 and may be truncated for subsequent derivative samples or products using the last five digits of the bar code (e.g., 26101) and further qualified using secondary alpha annotations (e.g., 26101A, 26101B, 026101C, etc.) or alternate annotation (e.g., 26101-supernatant, or 26101-precipitate, or the like).

Sample Integrity & Assessment

If not done previously, upon arrival, samples are visually inspected and the findings recorded. This may be followed by basic gravimetric measures and testing for solubility in 10 mL PBS buffer solution, up to a concentration of 50% at room temperature, and vortexed. Turbid samples are expected to yield a precipitate after centrifugation (5000 RPM×10 min). Supernatant aliquots (1.00 mL×2) are oven dried (60*C) in a watch-glass and gravimetrically compared to equal volumes of PBS buffer solution. An attempt to precipitate non-turbid samples and supernatant samples may be performed by the addition of ammonium sulfate or PEG6000 or both. The suitability of the sample may be determined by protein concentration and purity SDS-PAGE.

Example 9

Protein Identification by SDS-Page Methodology

Non-reduced separation of enzymes by SDS-PAGE is a common method in the course of substrate characterization (assessment of purity and protein sizes). Native protein mixtures must be partially denatured by a lauryl sulfate detergent, SDS, until they take on a non-hydrophobic, relatively linear conformation to permit rapid migration within a polyacrylamide gel matrix toward an applied, opposite electrical charge. Additionally, BME can be used to reduce all disulfide bonds of cysteine residues to free sulfhydryl groups, and heating in SDS will disrupt all intra- and intermolecular interactions within the substrate. After treatment with SDS, irrespective of native substrate charges, all enzymes/proteins acquire a high negative charge. The way of reduced and non-reduced separation of enzymes by SDS-PAGE electrophoresis differs only by the presence of the beta-mercaptoethanol. Within a wide pH range, the negatively-charged protein molecules will migrate toward the electrically charged chamber anode at a rate inversely proportional to their relative molecular mass. Mobile substrates are usually separated concomitant with standard protein markers of known mass such that the reference relationship between rate of migration (Rf) and mass can be plotted and the comparative masses of unknown enzymes/proteins may be estimated. A gel cassette, containing (4-15% or 7.5% acrylamide, should be expected to permit separation of polypeptides with molecular mass between 45 and 200 kDa.

Bromophenol blue indicator, introduced into the sample, electrophoretically travels ahead of the separating protein substrates toward the anode to cue completion; after this current is turned off to avoid sample loss due to complete electrophoretic migration. Once separation of the proteins has occurred (between the electrode poles), the resultant bands may be visually detected using various staining techniques.

After optimal migration occurs, the sample gels are removed from the plastic plates and stained with a protein-binding dye [e.g., Coomassie Brilliant Blue or Gel-Code Blue® (Pierce)]. Unbound dye is removed by repetitive washing and the amount of residual, bound dye is proportional to distributed protein content that appears as bands. Stained gels are photographed or scanned and the intensity of the color in each protein band may be measured with a recording densitometer. Bands are detected using a Western blotting-technique that incorporates specific antibody to the protein and chemo-luminescent detection of specific proteins on membrane. Alternatively, if the separated constituents are radioactive (not planned), the protein bands can be detected by radiography. When a piece of photographic film is applied over the dried slab in a light-proof cassette, X-ray film will be exposed to the light in the protein bands. After processing, dark bands appear on the developed film and may be quantified according to band intensity.

Purpose

The purpose of this Standard Operating Procedure is determine the spectrum of proteins and enzymes contained in a candidate digestive enzyme sample provided by the sponsor, QOL Medical, LLC.

Test Article Description and Risk Category

Description: a proteinaceous substance obtained from a GRAS-listed food product or supplement or non-pathogenic organism. NONHAZARDOUS and may be suitable for human consumption.

Frequency

Samples will be prepared and analyzed on an As Needed basis when requested.

MATERIALS AND REAGENTS Micropipettes and tips (Denvile Scientific, P1096-HPS) Mini-PROTEAN Tetra cell apparatus (BIO-RAD 552BR, 30 W) Trans-blot cell apparatus (BIO-RAD 49BT, 200 W) Mini-PROTEAN TGX Precast ready gels (BIO-RAD 456-1085) Precision Plus Protean All Blue Standards (BIO_RAD 161-0373) 4× Laemmli Sample Buffer (161-0747) 2-Mercaptoethanol (2-ME), SIGMA (cat #M3148) 4-15% Mini-PROTEAN® TGX™ Gel, 10 well, 30 µl #456-1083 Autoradiophy film (Dennville, E3018) TRIS buffer (Invitrogen, 15504-020) Glycine (Fisher BP381-5) Gel-Code Blue® (Pierce) Sodium dodecyl sulfate (SDS) (Sigma-Aldrich L3771) CAPS (3-(cyclohexamino)-1-propanesulfonic acid) (Sigma C2632) Immobilin-P membrane, PVDF, 0.45 um, (EMD Millipore IPVH00010) Various primary enzyme (target) antibodies (Cell Signalling Technologies, Beverly, Mass., https://www.cellsignal.com/) Secondary antibody-HRP (HRP anti-rabbit or antigoat or antirabbit (Santa Cruz Biotechnology) Chemoluminescent reagents (ECL Western Blotting kit, Pierce 32106) Kodak Automat (Baylor College of Medicine DDC/MVM) Milli-Q water Staining tray (Gelcode destaines with water) Milk, powder for blotting (Sigma M7409) Albumin-bovine (Sigma A9647) Ethanol, absolute>99.5% (AAPER or Sigma 459844) Tween 20 Working stock solution of test sample (annotated #-WS) Precision Plus Protein™ All Blue Standards BioRad (161-0373)

PROCEDURE If sample is not pure protein, several separate techniques will be required, including ammonium sulfate precipitation (~30-40%), FPLC gel filtration, affinity chromatography, and/or ion-exchange chromatography (each is a separate process and requires separate SOPs) and is dependent upon initial sample assessment, described below.

After determination of protein concentration (SOP 14-001), sample will be diluted with PBS buffer solution to a concentration 1-5 mg/mL and labeled as working stock (e.g., 26401-WS or #-WS).

To a 1 mL aliquot of #-WS, Laemli sample buffer with dye (1:1) to final concentration approximate 1-2 mg/mL (#WS/L) with for reduced and without 2-ME for nonreduced SDS-PAGE Assemble PAGE apparatus and load Mini-PROTEAN TGX Precast ready gel with 15-20 uL of (#WS/L sample and with reference markers (10 uL). Note: Protein concentration should not exceed 20 micrograms.

Apply current and run gel at ~120V for approximately 45 min.

Disconnect power and remove gel cassette from apparatus.

Remove gel from plastic retainer sheets and place gel on staining tray

Rinse gel (gently) with Milli-Q water to remove residual SDS solvent.

Stain gel with Gel-Code Blue® for approximately 1-2 hours

Destain and rinse 3× with Milli-Q water until bands appear

Photograph gel using Mobile HD Snap Camera (Sony MHS-PM5) and store images for transfer to E-laboratory notebook.

Analyze results with densitometer and plot molecular weight vs migration.

Alternative to staining (for inconclusive results) is to transfer proteins to membrane for Western Blotting.

Obtain PVDF membrane and immerse in absolute ethanol for 15 sec and rinse with Milli-Q water for 2 minute.

Affix gel to membrane (face-to-face).

Insert membrane cassette into Trans-blot cell apparatus and apply 400 mA current for 2.5 hours in CAPS buffer Remove cassette and discard gel Rinse membrane with PBS/Tween20 (0.005%) X2 to remove CAPS Dry membrane on paper towels for ~45 min.

Re-wet PVDF membrane with absolute ethanol C2 min. while gently shaking

Rinse PVDF membrane with Milli-Q water X1 Rinse PVDF membrane water with PBS/Tween20 solution X1

Block PVDF membrane with milk (5%)×1 hour at RT or overnight in refrigerator

Discard milk and rinse with PBS/Tween20 solution x1

Apply primary antibody (dilute 1:1000 to 1:10000 dependent upon stock specifications)×2 hours Rinse with PBS/Tween20 solution X3; 5 min each Apply secondary antibody (1:10000-1:30000 dependent upon stock specifications) X1 hour Rinse with PBS/Tween20 solution x1; 5 min each Add chemo-luminescent reagents [1:1 (~5 mL/membrane)] and incubate 2 minutes Remove excess ECL with filter paper, hold damp for not more than 25 minutes in x-ray cassette Insert x-ray film in darkroom from 1 sec to 1 minute, dependent upon anticipated concentration (ad lib)

Develop x-ray film in Kodak Automat developer machine

Optical computer scan film output.

Score results and record findings for analysis

Sample Integrity & Assessment

If not done previously, upon arrival, samples will be visually inspected and the findings recorded. This will be followed by basic gravimetric measures and tested for solubility in 10 mL PBS buffer solution, up to a concentration of 50%, at room temperature, and vortexed. Turbid samples are expected to yield a precipitate after centrifugation (5000 RPM×10 mins). Supernatant aliquots (1.000 mL×2) will be oven dried (60*C) in a watch-glass and gravimetrically compared to equal volumes of PBS buffer solution. An attempt to precipitate non-turbid samples and supernatant samples will be performed by the addition of ammonium sulfate or PEG6000 or both. The suitability of the sample will be determined by protein concentration and purity by SDS-PAGE as described herein, and will be following by assessment of enzyme activity, as per protocol.

Materials Safety and Data Source (MSDS)

Unless otherwise specified, physical data of the crude sample is believed to be a glucohydrolase substrate that is a creamy white hygroscopic powder, bland or slightly bitter in taste. It is produced by extraction from a GRAS listed, food grade microorganism such as *Aspergillus niger*. Substrate may be used to hydrolyze α-D-glucosides or in the brewing of beer and in the production of bread and juices. Similar enzyme substrates have been used to hydrolyze glycogen into glucose monomers in order to study lipid accumulation in skeletal muscle. The test compound should be capable of hydrolyzing the α-D-(1-4), the α-D-(1-6), and the α-D-(1-3) glycosidic bonds of oligosaccharides and serve as an extracellular enzyme to convert starch to dextrins and glucose. General Molecular Formula: [H2NCHR—(S)—COOH]n with sulphur being a variable constituent of individual, proteinogenic/composite amino acids with a total protein content that should approximate 30-60 units/Mg protein (biuret).

Example 10

Screening for Impurities Using Thin Layer Chromatography

Thin Later Chromatography (TLC) is a technique used for the identification or separation of compounds in mixtures. TLC is routinely used for monitoring the consumption of starting material in bioreactors and to observe for the appearance of desired products and problematic contaminants, such as pesticides and toxins. Unwanted organic products produced by *Aspergillus* or other species may include toxic contaminants including mycotoxins [(e.g., deoxynivalenol) and ochratoxins)] and rarely aflatoxins. TLC uses classic, two phase principles of extraction to accomplish the separation of compounds based upon inherent compound solubility in a mixture: a high surface area stationary phase and a mobile phase. The stationary phase consists of a thin layer (0.25 mm thickness) of absorbent silica on glass (Whatman K6 silica gel 60 Å; Cat. #4860-720; 10×20 cm). The mobile phase consists of a mixture of volatile organic solvents that evaporate after separation. In summary, a solution containing a particular solute substrate (e.g., invertase or amyloglucosidase) is applied near to the bottom edge of the glass TLC plate (the origin) and propped upright in a capped jar with the bottom margin of the plate submerged in the solvent. The ratio of absorbent to substrate must be high. With time, the solutes migrate upwards by capillary action with the leading edge of the rising solvents passing over the substrate origin (aka: elution). Various compounds become stationary at various levels according to inherent respective solubility. As the solvent rises approach the top of the plate, the plate is removed and slowly dried. One of the most important considerations is the selection of a solvent mixture with an affinity to be absorbed by the gel with full displacement of the solutes. Typical absorbents are highly polarized and have superb potential to elute compounds of interest. Heat causes discolorations to appear where various separated solutes became stationed. If necessary, portions of the silica gel can be selectively scraped, recovered, and analyzed to further determine identity. An ideal qualitative assessment would be absence of extraneous solutes.

PURPOSE: The purpose of this Standard Operating Procedure is to qualitatively screen enzyme samples obtained from suppliers on behalf of the sponsor and determine if impurities, such as mycotoxins are present. The approach uses thin layer chromatography, which is frequently used for the identification or separation of compounds in mixtures.

Materials

Pre-Run solvent: 50 mL ethanol 10 mL butanol 30 mL water

A-Run solvent: 30 mL ethanol, 60 mL butanol, 10 mL acetic acid, 10 mL water.

B-Run solvent: 65 mL ethyl acetate, 10 mL butanol, 15 mL pyridine, 10 mL acetic acid, 10 mL water.

Staining reagent:

7.0 g 4-aminobenzoic acid dissolved in methanol, 17.5 mL Orthophosporic acid Q.S. to 500 mL with methanol, Hardware: Thin layer chromatography plates 20×10 cm (Whatman Cat. #4860-720), glass migration chamber (jar); convection oven, 10 µL syringe PROCEDURES: The thin layer chromatography was performed using chromatograph glass plates coated with a 200 µm layer silica gel. The silica gel is an adsorbent that functions as the stationary phase. The plates are prepared by removing 1 cm from the vertical edges and top edge of the plate. The remainder of the stationary phase is divided into even columns. Using a 10 µL syringe, 5 µL of a 15 mg/mL sample is placed about 0.5 cm from bottom edge of a column. Once the sample is added, it has the appearance of a small spot. The plate is left to dry before proceeding.

Polar solvents, cited above, are used as the mobile phase of the chromatography. A glass chamber jar with a removable lid is used for the TLC runs. When the plate is placed inside the chamber it must be with the samples on the bottom of the plate. The samples must not be completely immersed in the solvent when the plate is initially placed in the chamber. When a TLC plate is ready to be run, the solvent is poured in the chamber, the plate placed inside as vertical as possible, and the chamber covered.

Once the plate is loaded with samples and dried, it is placed inside the glass chamber with the Pre-Run solvent and covered. The solvent rises up the stationary phase by capillary action. Once the solvent rises about 1 cm up just above sample, the plate is removed and left to completely dry, about 1 hour. The pre-run is repeated a second time. Once dry, the plate is placed inside the chamber containing the A-Run solvent. The plate is left until the solvent reaches as far as about 1 cm from top (this point is marked on the edge of the plate). The plate is removed from chamber, and left to dry, approximately 24 hours. Once it is dry the plate is placed in the chamber once more with the B-Run solution. The solvent is allowed to rise to the level that A-Run solvent reached (marked line). The plate is left to completely dry once more, again approximately 24 hours. The samples are most often colorless; hence, when the runs are complete the separation cannot be seen. The plate is developed by dipping it in the staining reagent and removing it immediately. It is then placed in an oven at 120° C. for 20 minutes. Once it is removed from the oven, the TLC plate will show any separated compounds derived from the heterogeneous substrate mixture.

Test Article Description and Risk Category

Description: a proteinaceous substance obtained from a GRAS-listed food product or supplement or non-pathogenic organism. NONHAZARDOUS and may be suitable for human consumption. The volatile solvents are considered HAZARDOUS (toxic, carcinogenic, and flammable) and require special care to avoid spills, inhalation and physical contact.

Frequency

Samples will be prepared and analyzed on an As Needed basis when requested.

Materials and Reagents

Pre-Run solvent: 50 mL ethanol 10 mL butanol 30 mL water

A-Run solvent: 30 mL ethanol, 60 mL butanol, 10 mL acetic acid, 10 mL water.

B-Run solvent: 65 mL ethyl acetate, 10 mL butanol, 15 mL pyridine, 10 mL acetic acid, 10 mL water.

Staining reagent:

7.0 g 4-aminobenzoic acid dissolved in methanol, 17.5 mL Orthophosporic acid; Q.S. to 500 mL with methanol, Hardware: Thin layer chromatography plates 20×10 cm (Whatman Cat. #4860-720), glass migration chamber (jar); convection oven, 10 μL syringe Procedure The thin layer chromatography was performed using chromatograph glass plates coated with a 200 μm layer silica gel. The silica gel is an adsorbent that functions as the stationary phase. The plates are prepared by removing 1 cm from the vertical edges and top edge of the plate. The remainder of the stationary phase is divided into even columns. Using a 10 μL syringe, 5 μL of a 15 mg/mL sample was placed about 0.5 cm from bottom edge of a column. Once the sample is added it has an appearance of a small spot. The plate was left to dry before proceeding.

Polar solvents, cited above, are used as the mobile phase of the chromatography. A glass chamber jar with a removable lid is used for the TLC runs. When the plate is placed inside the chamber it must be with the samples on the bottom of the plate. The samples must not be completely immersed in the solvent when the plate is initially placed in the chamber. When a TLC plate is ready to be run, the solvent is poured in the chamber, the plate placed inside as vertical as possible and the chamber is covered. Once the plate is loaded with samples and dried, it is placed inside the glass chamber with the Pre-Run solvent and covered. The solvent rises up the stationary phase by capillary action. Once the solvent rises about 1 cm up just above sample the plate is removed and left to completely dry, about 1 hour. The pre-run is repeated a second time. Once dry, the plate is placed inside the chamber containing the A-Run solvent. The plate is left until the solvent reaches as far as about 1 cm from top (this point is marked on the edge of the plate). The plate is removed from chamber and left to dry, approximately 24 hours. Once it is dry, the plate is placed in the chamber once more with the B-Run solution. The solvent is allowed to rise to the level that A-Run solvent reached (marked line). The plate is left to completely dry once more, again for approximately 24 hours. The samples are most often colorless, hence, when the runs are complete the separation cannot be seen. The plate is developed by dipping it in the staining reagent and removing it immediately. It is then placed in an oven at 120° C. for 20 minutes. Once it is removed from the oven the TLC plate will show any separated compounds derived from the heterogeneous substrate mixture.

Example 11

Estimation of Enzyme Activity by Rate of Glucose Production

There is a recognized need to supplement the diet of certain individuals with enterically-active starch digestive enzymes when inherent digestive capacity is limited or absent. Beginning in the proximal small intestine of a normal individual, free glucose is actively absorbed into the body by means of the luminal SGLT-1 protein receptor-transporter. Most free glucose is released by enzymatic digestion of larger carbohydrate molecules beginning in the duodenum. The glucose uptake receptor is sodium-gradient driven by extrusion of sodium at the basolateral surface of the enterocyte, such that apical glucose uptake is coupled to replacement sodium uptake. As such, the affinity of SGLT1 for glucose is markedly reduced in the absence of Na+ and the varied affinity of SGLT1 for different monosaccharides reflects its preference for specific monosaccharide molecular configurations, all of which have various downstream physiological consequences that far transcend simple hydrolysis. In summary, the ingestion, digestion, and absorption of carbohydrates is intricately dynamic.

In health, the system is optimized, but SGLT1 is limited by two structural requirements for monosaccharide uptake: (1) a hexose in a D-configuration, and (2) a hexose that can form a six-membered pyranose ring. As such, oligosaccharides, dextrins, and starches must be completely hydrolyzed by luminal and mucosal derived enzymes (hydrolases) to permit efficient hexose absorption. The bulk of absorption occurs distal to the ampula of vater from which excreted pancreatic amylase initiates starch digestion in the lumen. The mammalian physiology has evolved to be a tiered system to hydrolyze crude starch to dextrins and oligosaccharides over the proximal length of the small intestine, which is then followed by relatively specific hydrolytic activity of dextrins and oligosaccharides at the jujunal mucosal level to produce free glucose, galactose, or fructose. Illeal function acts, in part, to scavenge residual nutrients. The teleological theory holds that complete digestion and absorption ensures that nutritional needs are met; and limits dumping of fermentable substrates into the colon that would cause adverse symptoms.

In clinical cases, where sufficient mucosal enzymes are lacking, oral replacement therapy is needed. This treatment approach has been successfully used to hydrolyze lactose to glucose and galactose and to hydrolyze sucrose to glucose and fructose, but therapy to exogenously assist starchy oligosaccharide and dextrin digestion is lacking. The work described herein relates to the quality (activity) of the particular food-grade, fungal-derived enzymes, such as amyloglucosidase, produced by molecular biology or microbial culture techniques to release glucose from large target substrates in the human stomach and duodenum.

The approach to the determination of enzyme activity is to estimate the rate of glucose production from observations made on a controlled substrate reaction between enzyme and oligosaccharides (dextrins) or starches. The assessment of glucose production involves the use of test enzymes to hydrolyze oligosaccharides or starches, from which indirect measurements of resultant free glucose are made. The traditional technical approach relies upon a glucose oxidation reaction that yields a reactive species that effects a colorimetric change that correlates with glucose concentration, and a more modern approach relies upon a change in oxygen ion concentration that correlates with glucose concentration. In the later scenario, oxygen consumption from glucose oxidation is detected by use of a Clark-type amperometric, platinum oxygen electrode. This is the same, highly accurate method upon which blood gas analyzers are based. Test enzymes, for which activity is undetermined, can be assayed using semi-micro quantitative analysis. Exploiting the later principle, the work described herein relates to the quality (activity) of the particular food-grade, fungal-derived enzymes, such as amyloglucosidase produced by molecular biology or microbial culture, to release glucose from target substrates in the human stomach. Amyloglucosidase has broader activity than mammalian physiological enzymes, appears to be a robust candidate therapeutic agent, and is probably active in the stomach. Invertase, an enzyme used to hydrolyzed sucrose, may be assayed in a similar way. The candidate digestive enzyme samples (amyloglucosidase or invertase) as provided by the sponsor were tested. HPLC-grade analytical enzymes are used for comparative purposes. Results are reported regarding milligrams glucose produced periodically (over 60 minutes) and converted to USP activity units consistent with USP Dietary Supplements Compendium, (the United States Pharmacopoeial Convention, Inc., Rockville, Md., USP/DSC 2nd ed., 2012) Appendix V, Enzyme Assays pg. 1727-1759. One unit of glucoamylase activity is defined as the amount of glucoamylase that will produce 0.1 μmol/min of glucose under the conditions of the assay. Other assays rely upon sample hydrolyzes of p-nitrophenyl-α-glucopyraniside (PNGP; C12H15NO8; Molecular Weight 301.25) to p-nitrophenol (PNGP) and glucose and measurement of PNGP at pH 4.3 and 50° C. The electrochemical (oxygen consumption) measurement of glucose production closely equates to p-nitrophenyl since the molecule is hydrolyzed in a 1:1 ratio. The electrochemical technology used in these experiments is exceptionally fast with results becoming available in less than 20 seconds after sample injection. This timely approach prevents overestimation of enzyme activity and is remarkably free from the interference problems associated with antiquated PNGP optical techniques.

In a similar way, sucrose hydrolysis is defined regarding Sumner Units (SU). This is the activity of the enzyme which, under the conditions of the assay, will convert 1 mg of sucrose to glucose and fructose in 5 minutes. One method spectrophotometrically measures the amount of monosaccharides produced as a 3,5-Dinitrosalycylic Acid (DNS) acid-phenol reagent byproduct correlated to a glucose standard. The methods used herein again measures the rate of glucose production electrochemically. Since result fructose is unaffected by glucose oxidase and only the glucose moiety is detected and the results must be doubled to reflect SU or IU.

Herein, the research question asks whether a submitted candidate test enzyme could be sufficiently active in vitro to propose for further in-vivo use as a therapeutic replacement for luminal deficiency conditions. The general testing approach described herein is antecedent to potential large-scale enzyme extraction, purification and pharmaceutical applications. If preliminary results appear promising, this SOP will serve as the basis for other related testing protocols (sub-SOPs) to assess potential factors that could inhibit or potentiate enzyme activity or affect enzyme stability. Purpose The purpose of this Standard Operating Procedure is to determine enzyme activity associated with the total glucose produced from standardized substrates, including maltose, palatinose, corn LDx, potato starch, and corn starch. The candidate digestive enzyme sample (amyloglucosidase or sacrosidase) will be provided by the sponsor or provided locally.

Test Article Description and Risk Category

Description: a proteinaceous substance obtained from a GRAS-listed food product or supplement or non-pathogenic organism. NONHAZARDOUS and may be suitable for human consumption.

Frequency

See work flow rubric, shown below. Samples will be prepared and analyzed on an as needed basis when requested by collaborating scientists at QOL Medical and supplied in suitable form. Materials and Reagents 10 mM NaCitrate buffer, pH 4.5 (10 mM Citric acid, pH 4.5 with NaOH)

Thimersol, 5% aqueous, 200 μL added to each liter of NaCitrate buffer to prevent premature glucose bacterial consumption (noted not to interfere with reactions)

Reaction vials, borosilicate with caps, 8 mL

Analox glucose analyzer and commercial reagents (glucose oxidase)

Glucose control solutions (100 and 400 mg/dL)

Pipettes

Vial warmer set within Lindberg/Blue M shaking water bath, model SWB1122A-1 set to 37° C. (Serial number R02L-524123-RL).

Substrate A: 1% maltose in 10 mM sodium citrate buffer, pH 4.5

Substrate B: 1% palatinose in 10 mM sodium citrate buffer, pH 4.5

Substrate C: 1% corn LDx in 10 mM sodium citrate buffer, pH 4.5

Substrate D: 1% potato starch in 10 mM sodium citrate buffer, pH 4.5*

Substrate E: 1% corn starch in 10 mM sodium citrate buffer, pH 4.5*

*Solubilized by cooking 2% slurry for 10 minutes, bring to boil, then simmer, then cool. Dilute 1:1 prior to use using 10 mM sodium citrate buffer, pH 4.5 Test article: as supplied.

Procedure

Prepare samples and set up test and control vials in duplicate in cold (wet ice or cold block). Note: stagger sample preps, starting each test vial at 30 sec or 1 minute intervals between measurements. e.g., 20 samples+2 glucose standards in 10 minutes in the initial cycles.

In duplicate, add 2 mL stock substrate-solution (either A, B, C, D, E) into paired borosilicate vials with caps for 10 time points: 0, 10, 20, 30, 40, 50, 60, 70, 80, 90 minute samples, a blank with citrate buffer only and glucose control samples (100 μL: 100 mg/dL; 10 μL: 400 mg/dL) (#26 total). Additional glucose control samples at lower concentrations may be used as necessary.

Prepare 10 mL stock solution of test enzyme or reference enzyme (e.g., 1.0 mg/mL for reference A. niger sp. AMG, Sigma A7420). Use 50 mL conical tubes. The target enzyme concentration to use in this protocol is 1.0 mg per mL, as determined from previous protein concentration determinations. As such, enzyme volumes will need to be adjusted accordingly after final protein concentration is determined.

For example, samples, aliquot 0.10 mL (~0.07) mL from stock and q.s to 10 mL with sodium citrate buffer (protein concentration 143.7 mg/mL; x-factor 0.007×10).

For example, aliquot 50 mg (~49.0 mg) from stock (core protein concentration: 20.4% dry).

For example, aliquot 13.00 mg (~12.35) mg from stock and q.s to 10 mL with sodium citrate buffer (core protein concentration: 81% dry).

Vortex for 1 minute each and centrifuge using table top IEC instrument (position #7 for 10 minutes (~2500 RPM)), and transfer each supernate to a new 50 mL conical tube.

Qualitatively filter each supernatant using fine filter paper (Whatman #42), then repeat using very fine filter paper (Whatman #GF/C).

Optional: repeat filtration to remove residual microorganisms using closed-system suction-driven apparatus (Steriflip-GP, EMD Millipore #SCGP00525) and collect in sterile 50 mL conical tube.

Repeat protein concentration assays according to SOP #2 to permit accurate enzyme dilutions and intragroup comparisons. Adjust proportionally with sodium citrate buffer to final concentration of 1.0 mg/mL. o Measure glucose concentration of the glucose controls (25, 100 and 400 mg/dL) using the Analox instrument Measure glucose concentration of the test substrate (either: A, B, C, D, E) prior to adding enzyme test article. Repeat for duplicate vial.

Measure glucose concentration of the enzyme test article prior to mixing with substrate (either: A, B, C, D, E).

Add 200 μL normalized enzyme test article to 2.000 mL substrate (either: A, B, C, D, or E). Repeat for duplicate vial.

Incubate duplicate vials at 37° C. in gently shaking water bath.

Remove 10 μL at 10 minute intervals and determine glucose levels. Repeat for duplicate vial. Consider staggering timing for vials to account for time taken to assay samples.

Measure glucose controls (25, 100 and 500 mg/dL) after each sample set.

Tabulate and plot all results. For each enzyme dilution, plot glucose (mg/dl) generated vs time.

Calculate glucose production rate in mg/dL/min. Select peak glucose concentration (e.g., 70 minute sample) and determine rise in glucose concentration during previous 60 minutes (e.g., [70 min mg/dL glucose-70 min mg/dL glucose] and divide by 60 and record glucose production rate in mg/dL/min.

Repeat entire procedure, but increase test article 2× by adding 400 μL normalized enzyme test article to 2.000 mL substrate (either: A, B, C, D, E). Repeat for duplicate vial.

Repeat entire procedure, but increase test article 4× by adding 800 μL normalized enzyme test article to 2.000 mL substrate (either: A, B, C, D, E). Repeat for duplicate vial.

Glucose Standards may be 100 mg/dL Glucose Standard. Substrate may be 400 mg/dL. The time duration may be 0, 10, 20, 30, 40, 50, 60, 70, 80, or 90 minutes mg/dL, for example, where measured glucose concentration using Analox GM9]

Substrate A: 1% maltose in 10 mM sodium citrate buffer, pH 4.5

Substrate B: 1% corn starch in 10 mM sodium citrate buffer, pH 4.5

Substrate C: 1% corn LDx in 10 mM sodium citrate buffer, pH 4.5

Substrate D: 1% potato starch in 10 mM sodium citrate buffer, pH 4.5

Substrate E: 1% corn starch in 10 mM sodium citrate buffer, pH 4.5 10.

Other Background Information

In agriculture, starch is the primary energy reserve and is found in cereal seed, tubers, legumes, fruits, and vegetative tissue and provides ~70% of the calories consumed by humans. In nature, starch occurs as granules, and the rate of enzymatic hydrolysis of these granules before and after physical, thermal, or chemical damage has a major impact on the nutritive properties of the grains. From an analytical viewpoint, properties such as total concentration of starch, degree of fracturization upon milling, and the extent of extent of gelatinization dictate methodology. From a nutritional point of view, resistance to digestion in the small intestine is an important factor in determining suitability as foodstuffs.

In the intestine, dietary starches must be reduced to soluble dextrins and oligosaccharides by pancreatic amylases and, in turn, the dextrins and oligosaccharides must be reduced to monosaccharides by isomaltase and maltase before receptor-mediated glucose uptake occurs. (Note: the primary purpose of pancreatic alpha amylase activity is to reduce and solubilize megamolecules to highly soluble substrates that can be easily acted upon by hydrolytic enzymes originating at the mucosal level). Enzyme deficiency or insufficiency at either the pancreatic or mucosal level results in failure to completely hydrolyze glycosidic linkages that results in maldigestion, secondary malabsorption and distal colonic fermentation. Malabsorbed oligosaccharides have been associated with the gastrointestinal distress symptoms that include pain, bloating, and diarrhea. As such, insufficient endogenous enzyme production could benefit from exogenous replacement therapy, but the qualities of candidate replacement therapies must be known in order to determine proper substrate targeting and dosing. While pancreatic replacement therapy has been available for decades, mucosal enzyme supplementation has been limited to targeting lactose (with lactase) and sucrose (with sacrosidase). Conventional medicine has largely ignored maldigestive issues related to the bulk of the dietary carbohydrate load ("starches"), and OTC remedies are not known to be truly efficacious.

The most important feature of mucosal enzyme activity (efficiency) is production of free glucose from its immediate and primary oligosaccharide substrate and activity is reported as a rate of glucose production in terms of milligrams glucose per gram of substrate per unit of time (minutes). Other features, such as physical characteristics and stability, are addressed elsewhere. The technical measurement of polysaccharides or oligosaccharides in food substrates involves degradation to the reducing sugar components (glucose), which then can be measured either enzymatically and coupled with colorimetry, or by employing various instrumental procedures such as high-performance liquid chromatography (HPLC). A useful method is faster and uses the principle of electrode detection of enzymatic oxygen uptake by the oxidoreductase and dehydrogenase enzyme-mediated glucose reaction. Starch or soluble oligosaccharides [limit-dextrins (LDx)] concentrations can be expressed in terms of dextrose-equivalents or glucose-equivalents. The later electrochemical glucose detection method relies up measurement of oxygen consumption from the production of hydrogen peroxide by glucose oxidase and, under the conditions of the assay the rate of oxygen consumption is directly proportional to glucose concentration. This assay approach is accurately detected by an oxygen-sensing electrode (ANALOX, London, England, PMID: 7762948) and is believed to lessen the chance of technical errors. Final results are determined by regression analyses against standards.

Limit dextrins (LDx) are oligosaccharides that are incompletely hydrolyzed only to the limit that pancreatic alpha amylase will facilitate the reaction to progress. LDx is the transitional nutritional substrate that is produced in the intestinal lumen. Complete digestion requires further hydrolysis at the mucosal level before absorption can occur. As such, insufficient endogenous enzyme production requires exogenous replacement therapy, and the qualities of candidate replacement therapies must be known to determine proper dosing. As such, maltose, LDx, palatinose (as a surrogate for isomaltose) and cooked starch are the target substrates that this work is most concerned because they represents the natural (luminal) post-pancreatic dietary substrates that are produced for luminal-mucosal-bound hydrolases to act upon (the brush border enzymes or endo-amylases) and this is a critical step in the hydrolytic process when, theoretically, maldigestion can be prevented. Since LDx is highly soluble, stable, and extremely accessible to amyloglucosidase hydrolysis, it is among the most desirable substrates for in vitro work. Furthermore, since corn starch is one of the primary dietary starches and is free of gluten, it is also a preferred species upon which to test various amyloglucosidase (AMG) activities. Potato, tapioca, and edible algal starch are also considered good crude sources for LDx production. The rate of LDx hydrolysis also depends on the type of linkage and on the chain length of the substrate, $\alpha$-1-4 linkages are more easily hydrolyzed than $\alpha$1-6 or $\alpha$1-3 linkages. However, maltotriose and in particular, maltose and palatinose are hydrolyzed at slower rates than higher oligosaccharides, presumptively due to the rapid glucose production that inhibits AMG activity. As such, it is unlikely that reactions could go to absolute completion. To develop test parameters, several typical reaction analyses are shown below.

A prototype assay was developed using commercial, reference reagent-grade AMG (Sigma-Aldrich A9229) diluted to a concentration of 2 mg/mL (100 uL AMG) and provided a model for a standard reaction and which produced free glucose at a rate of 0.2 mg/dL/hour (1.4 uM/min).

It was concluded that an enzyme concentration of 1 mg/mL would be sufficient for future work. A second pilot test using maltose as a substrate was performed on 24 Jun. 2014 using 100 uL of 1 mg/mL amyloglucosidase (Sigma-Aldrich A9229) stock solution in 1 mL of 10 mg/mL maltose (Sigma-Aldrich M2250) substrate stock solution.

The expectation was that robust hydrolysis would occur, since amyloglucosidase is selective of alpha 1-4 linkages. The beginning glucose content of 1 mg/mL (100 mg/dL) amyloglucosidase stock solution was 8.1 mg/dL and the beginning glucose content of 10 mg/mL (1000 mg/dL) maltose stock solution: 9.5 mg/dL. The resultant data curve demonstrated an excellent free glucose production rate of 9.2 mg/dL/min.

Example 12

Use of Amyloglucosidase Supplementation in Functional Bowel Disorders, Congenital Sucrase Isomaltase, Small Bowel Mucositis, and Protein Calorie (Energy) Malnutrition In health, the intestinal mucosal cells function to absorb monosaccharides from hydrolyzed complex dietary carbohydrates and, when cells are damaged (illness), they are significantly impaired from completely hydrolyzing oligosaccharides and this leads to gastrointestinal symptoms. The mucosal cells are dynamic and assimilate the luminal digestive products and transfer nutrients to various endogenous metabolic processes (Ravich and Bayless, 1983). At the earliest level, food digestion critically depends upon secretion of salivary and pancreatic $\alpha$-amylase; then is completed by cellular expression of several other apical digestive enzymes. First, dietary starch is 'coarsely' hydrolyzed in the duodenum and jejunum, by intraluminal alpha-amylase to release soluble maltose, maltotriose, oligosaccharides and alpha-limit dextrins. These intermediate by-products of partial digestion are not directly absorbable and must undergo further enzymatic hydrolysis (cleavage) at the apical enterocyte surface to monosaccharides (glucose, fructose, and galactose) by expressed sucrase-isomaltase (SI), maltase-glucoamylase (MGAM), and lactase. These enzymes, along with trehalase (a minor player), are continuously produced by healthy luminal enterocytes that constitute the apical mucosal surface, also referred to as the brush border because of the exposed velveteen-appearing microvilli. Released monosaccharides, mostly free glucose, enter the absorbing enterocyte at the apical surface by specific transport mechanisms ("carriers") and are distributed to the body using and inhibit hepatic gluconeogenesis. It is well known that mucosal enzyme activity is frequently reduced in states of inflammation, functional bowel disorders (Sinagra et al., 2016), malnutrition (Mehra et al., 1994), and mucosal injury (Stringer et al., 2007), and this is a largely unaddressed therapeutic concern.

The complete digestion of starch is thought to be predominantly reliant on the proper expression and function of the sucrase-isomaltase (SI) enzyme complex [chromosome 3q26.1](Auricchio et al., 1963) and deficiency conditions exist. The SI is a complex composed of two $\alpha$-glucosidase units, sucrase, and isomaltase (Conklin et al., 1975). The isomaltase component demonstrates considerable $\alpha$-glycosidic activity on starch-derived glucose oligomers, and the SI complex together contributes to 60 to 80 percent of total intestinal maltase activity (Gericke et al., 2016). The isomaltase component of the SI complex hydrolyzes 1,6 linkages of the $\alpha$-limit dextrins after primary luminal pancreatic amylase has reduced the ingested starch (Galand, 1989). Surprisingly, its role in causing symptoms of maldigestion has been largely ignored until recently when our group made advances in the field. Secondarily, mucosal maltase-glucoamylase (MGAM), a chromosome 7q34 gene product, is relatively restricted to hydrolyze alpha 1-4 bonds of soluble oligosaccharides, and the SI component works in dominant concert to hydrolyze $\alpha$-1-6 bonds and complete digestion to glucose (Diaz-Sotomayor et al., 2013). MGAM is noted to have a significant amount of compositional amino acid sequence homology, but is insufficient to make up for the loss of SI. Acquired and congenital enzyme deficiency syndromes can be due to specific gene mutations (Geng et al., 2014) and secondary transport errors or combinations thereof (Jacob et al., 2000; Puntis, 2015). There are needs for an AMG supplement or medicinal food to assist those with irritable bowel syndrome and malnutrition associated with several etiologies.

Using crude AMG purchased from UltraBiologics (GRAS), in Montreal Canada, the feasibility of using AMG taken by mouth to aid human digestion of starches was successful. The aim was to provide 16-thousand activity units (AGU) per capsule; which is in line with current dosage strengths for $\alpha$-amylase contained in Pancrease HL®

USP. AMG is sourced from the fermentation of carbohydrates by *Aspergillus niger*, is crude (possibly derived from the elution of the mash). Crude AMG thought to contain various aberrant substances, not limited to aliphatics, aromatics and possibly trace amounts of organic mycotoxins, such as deoxynivalenol (aka: vomit toxin) (Bennett, 2003). A critical feature that was exploited for purification purposes is that AMG is completely insoluble in absolute ethanol. As such, a technique to prepare high strength AMG capsules without aberrant substances has been outlined using semi-micro quantitative analyses (e.g., enzyme activity) and thin layer chromatography (TLC). Newly produced capsules were taken by mouth and were well tolerated with adverse events. Efficacy studies are underway (IRB Approved Protocol H-19253) using a modified stable isotope-labeled tracer technique (Opekun et al., 2016).

Several experiments were performed to compare the activity of purified AMG compounded with a powder excipient (B) containing 80% calcium carbonate+10% Calcium phosphate+10% Calcium silicate. The Excipient B results showed minor 45%, 35%, 73%, 45% and 4% decreases in the enzyme activity on sorghum, rice, wheat, maize, and millet respectively. These experiments need to be confirmed. Then another set of experiment was done to define whether concentrating the AMG enzyme using a centrifugation technique (Centriprep®) or overnight evaporation technique resulted in obtaining a higher enzyme activity compared to non-concentrated AMG. The results showed the 2×AMG, from overnight evaporation concentration technique, carries the highest enzyme activity, even higher than the 4×AMG from Centriprep® concentration technique. The aforementioned experiments demonstrated excellent rates of glucose production approaches a steady state level after 5 minutes. An additional experiment was done by diluting the AMG enzyme and increasing the volume of the sorghum substrate to mitigate inhibition of activity. The anticipated results of that experiment indicate that high glucose levels inhibit activity, which is a desirable outcome of clinical utility. Comparing different technique of AMG capsules preparation; using excipient A (80% calcium phosphate, 10% Calcium carbonate and 10% Calcium silicate) along with the 2×AMG from overnight evaporation concentration, excipient A has the highest enzyme activity (19K AGU) and the shortest preparation (drying) time.

The present disclosure provides a significant advance in the development of AMG and desire to partner with GMP industry to produce and market a high potency AMG nutritional supplement or medicinal food. The essential steps to produce potent AMG capsules have been worked out and include sourcing of good quality crude AMG, purifying it (washing) it from a toxins and irritants with absolute alcohol, removing insoluble particulate matter (mash) derived from the fermentation process, mixing the aqueous product with excipient, air drying, encapsulation (#00), packaging, labelling and distribution for sale. Such a product is in high demand, especially from among those who suffer from irritable bowel syndrome (~30% of the U.S. population) and garner great interest from parties that are addressing the issue of world hunger.

Example 13

Example of AMG Purification Method

One specific example of an AMG purification method is as follows:
1) Verify crude stocks of amyloglucosidase and QA, Chain of Custody from UltraBiologics [UB Lot #1109171347, BCM #700126464]
2) 1 part CRUDE AMG (UltraBiologics): 1 parts Absolute ETOH
60 grams AMG=20 mL dry volume dispersed as 20 mL per 50 mL conical tube (#4) and to each was added 20 mL 100% ETOH and 10 μlass beads. Each was vortexed 5 minutes. Glass beads were removed.
3) Swing arms centrifuge (mushroom) at 2500 RPM for 30 minutes, aspirate all ETOH and extracted toxic lipid top layer to waste [note that toxic lipids were obvious (5+)]
4) Repeat steps 2 and 3, once. [note that supernatant showed minimal presence (1+) of lipids for QA].
5) Retain solids, q.s. 50 mL conical each with Milli-Q water, combine to a beaker (200 mL) and hand blend for 5 minutes (Kitchen Aid KHB1231).
7) Centrifuge at 2500 RPM for 45 minutes, recover (decant) supernatant with AMG, discard sediment ppt.
9) Buchner suction filter using Whatman #2 retains>8 uM under low suction.
10) Fixed arm centrifuge 6000 RPM for 59 minutes to recover clear tan supernatant (~40 mL). N.b., this essentially concentrates the final product by altering the final ratio of product to excipient and prevents subsequent clogging of the adsorptive sprayer. (Yield approximates, 60 mL, qualitative tests POSITIVE for protein ~50 mg/dL).
11) Adsorb to excipient (calcium carbonate, calcium phosphate, sodium silicate 8:1:1) in 2:1 ratio AMG:excipient.
12) Dry overnight on stretch plastic wrap tray under Class 100 blowing hood and UV light.
13) Collect product as flakes and chunks to clean high-speed coffee grinder.
14) Sift to clean tray, repeat pulverization on any retained particles and transfer to 50 mL conical.
15) Suspend in absolute ETOH 1:1 and vortex 5 minutes.
16) Centrifuge at 2500 RPM for 15 minutes, recover sediment ppt, discard alcohol (should be crystal clear, no lipid layer).
17) Disperse solid to stretch plastic wrap tray under Class 100 blowing hood and UV light for 2 hours (spread thin to dry quickly).
18) Encapsulate to #00 capsules (750 mg each). [fine light tan powder, homogeneous]
19) Label as Lot #AMG ddmmmyy
19) Test for deoxynalevenol (DON-V, Vicam Millipore). The specification should test negative to less than 0.05 ppm.
20) Test for AMG starch hydrolysis activity as per SOP. The specification should exceed 7500 AGU per capsule.

Example 14

Development of AMG Capsules for Human Consumption

Disaccharidase deficiency syndrome results in the inability to absorb ingested saccharides in the gastrointestinal tract because of the failure to completely hydrolyze saccharides within the lumen of the small intestines. Complex sugars (oligosaccharides) and starches are normally metabolized to monosaccharides by the intestinal enzymes maltase-glucoamylase and sucrase-isomaltase and absorbed in the small intestine. Failure to hydrolyze oligosaccharides and starch (maldigestion) to monomers results in symptoms of gastrointestinal malabsorption. As a prototypical condition, congenital sucrase-isomaltase insufficiency disease (CSID) is a rare, genetic disorder that results in reduced sucrase-isomaltase (SI) enzymatic activity necessary for cleaving the disaccharide sucrose and starch in the small intestine. Acquired deficiency conditions also exist. Nevertheless, loss of SI results in adverse gastrointestinal signs and symptoms, which may be incapacitating.

SI deficiency often leads to symptoms such as bloating, abdominal pain, and chronic diarrhea as maldigested carbohydrates pass into the large intestine causing an osmotic load, bacterial fermentation, and accelerated transit in a manner similar to lactose intolerance. As a result, patients deficient in SI have reduced nutrient absorption, chronic malnutrition, or failure to thrive. Small intestinal endoscopy with mucosal biopsies is the historical "gold standard" for diagnosing SI deficiency using a disaccharidase activity assay. The enzymatic activity level of SI are measured as a ration to protein levels found in the biopsies and compared with normal values.

This disclosure puts forth the concept that ingestion of non-toxic fungal-derived enzymes [e.g., amyloglucosidase, (AMG)] could significantly aid in the hydrolysis of dietary starches (CAS Number: 9032-08-0) in the absence of effective isomaltase activity. Administration of AMG should be helpful as a nutriceutical or medical food to release glucose in the stomach, with or without the addition of invertase, which hydrolyzes sucrose (table sugar) to glucose and fructose.

Description of Test AMG Article: Purified amyloglucosidase in Milli-Q water adsorbed to inert excipients (Calcium phosphate 10 g, Calcium Silicate 10 g, Calcium Carbonate 80 g or various proportions thereof) and dried. The materials are GRAS, considered NONHAZARDOUS and are suitable for human consumption without regulation. Minimal risk.

Examples of Procedures

The counter, analytical balance, instruments, and vent hood must be cleared, clean with warm/soapy water followed by ethanol wipe down. Working area and Class 100 clean bench hood must be lined with new plastic lined absorbent pads. Personnel should don disposable nitrile gloves, protective garments, eye protection and disposable face mask when preparing product for human consumption. All disposables should be food-grade safe clean or sterile and non-disposables should be deionized-filtered water rinsed, acetic acid rinsed (1%) and air dried in safe space covered with protective shield until ready for use. Working area is a spark-free zone.

Amyloglucosidase Preparation: Measure 75 g crude AMG (Lot: 5220211016), place in a clean 1.2 L chilled blender jar (with cap), admix 150 mL cold absolute ethanol, USP and emulsify using a high speed commercial blender (Waring 700, Model 31BL46, New Hartford Conn.) for 15 minutes, taking care to avoid excessive heat. (Total volume should approximate 240 mL.) Equally aliquot the resultant AMG/ethanol suspension by aliquoting ~40 mL of suspension to six 50 mL conical tubes (Corning). Centrifuge the conical tubes with AMG solution at 6,000 rpm for 60 minutes using fixed-arm centrifuge at 10 degrees Celsius; after centrifugation, three layers will be observed. Using disposable Pasteur pipettes or vacuum aspiration apparatus, aspirate the floating top lipid/debris layer to waste, decant the ethanol solute from each conical tube and hold supernatant for assay of deoxynivalenol. Retain the precipitate containing AMG in each conical tube. Label as indicated.

Using each precipitate, from above, repeat the ethanol wash process with minor variations by adding 10 grams of clean glass or stainless steel mixing balls to each conical tube, admix cold absolute ethanol, USP (q.s. 50 mL each conical tube) and vigorously vortex for 5 minutes. Centrifuge each AMG solution again at 6,000 rpm for 60 minutes, decant the ethanol solute and retain both the precipitate and supernatant for testing. This ethanol wash step maybe repeated if it is determined that excessive amounts of deoxynivalenol persists according to specifications.

Extract the AMG from the sediment by admixing cold purified water (e.g., 3M Water Dual Port Water Filtration System—. DP290, 0.2 Micron Rating and 10 GPM) (q.s. 50 mL each conical tube or a ~2:1 ratio water to AMG) and vigorously vortex for 5 minutes. Centrifuge each AMG solution at 6,000 rpm for 60 minutes. Pour off the AMG solution/sediment suspension to vacuum filtration apparatus. Using a modified filter flask, vacuum line, and Whatman-GE GF8 glass filter (Cat. #10370105), transfer the contents of each conical tube to filter receptacle and collect AMG solution and discard sediment. Repeat filtration process in separate apparatus using Whatman-GE #2 qualitative filter, aliquot 5 mL for quality control and assay and retain volume balance for admixing to excipient and drying.

Resultant AMG solution should be light brown and test positive for protein in excessive of 50 mg/dL by dipstick reagent (Bayer Healthcare Model: 2184). Product glucose concentration is expected to be negligible. Total expected yield of purified product is 200 mL.

Quality Control Assays

Deoxynivalenol: determination of deoxynivalenol concentration: air dry at room temperature 10 mL aliquot of each ethanol wash solution and reconstitute using 400 uL commercially-supplied VICAM DON-V diluents buffer (#100000248) solution and apply 100 uL to VICAM DON-V test strip according to manufacturer's instruction using VICAM Vertu, Lateral Flow Reader equipped with VICAM Don-V quantitative test strips and recorded with a GeBE-FLASH, easy-load desktop-thermal printer and record result as parts-per-million corrected for 10 mL concentrated aliquot. Note: direct assay for deoxynivalenol of crude AMG (aqueous) is expected to result in false negative outcomes due to contaminate interferences known to exist.

Activity: under separate SOP, measure the enzyme activity 1 ml of refined AMG solution, or strict portion thereof, then calculate enzymatic activity for desired starch substrate using Analox Glucose Analyzer (GM-9) (or suitable alternative). Typically sorghum and rice flour are used since those substrate are low in protein content.

Protein Content: Under separate SOP, determine protein concentration of AMG (Lowry Method) if required. Resultant value needed for SDS-PAGE.

Identification: Under separate SOP, confirm presence of AMG using SDS-PAGE compared with commercial reference standard (Amyloglucosidase from *Aspergillus niger*, Sigma-Aldrich A7420, MW 97 KD).

Amyloglucosidase Capsule Preparation: Admix 200 mL refined AMG solution to 100 grams of mixed calcium salt excipient (USP), such carbonate (8 parts), silicate (1 part) and phosphate (1 part) mixture to a clean beaker and mix well; note that to excipient proportions should be optimized for mechanical capsule filling. Pour mixture to drying trays lined with food-grade plastic wrap and permit to air dry overnight in low humidity clean room or under Class 100 hood. Collect dried mixture and pulverize using clean blender or coffee grinder until particle size meets specifications suitable for standard pharmaceutical-grade gelatin capsule filling. Alternative procedures for admixing, including spray application of enzyme to excipient, have been described elsewhere and may be suitable depending upon up-scaling needs. Using resultant value for final product AMG activity (see above), the product should be proportionally adjusted for desired activity using neutral calcium salt excipients to obtain desired dosage to fill ratio for either #00 or #0 sized gelatin capsules. AMG activity specification may approximate 4000 AG activity units or more (up to 20,000 AGU). This procedure is subject to alterations depending upon equipment availability and current state-of-the-art for substrate encapsulations.

In specific embodiments, one can ingest 2 capsules by mouth per meal and the capsules may be stored in a cool and dry place Example 15

Amyloglucosidase Supplementation Corrects Small Intestinal Isomaltase Insufficiency in Symptomatic Patients Carbohydrate (CHO) maldigestion due to mucosal disaccharidase deficiency occurs with hypolactasia and primary or secondary sucrase-isomaltase (SI) deficiency. When CHO load exceeds digestive capacity patients develop symptoms of abdominal discomfort, bloating and change in stool character. Enzyme supplements are available for lactose and sucrose digestion. However, starch and dextrins constitute more than 50% of a typical diet and supplemental digestive enzymes are not available for post-pancreatic starch digestion (mucosal level dextrins and soluble oligosaccharides). While FODMAP restriction diets appear to be helpful, supplemental amyloglucosidase (AMG) directly addresses the cause of symptoms. The present example tests whether AMG supplementation accelerates starch digestion.

METHODS: Stable isotope $^{13}$C-labeled starch load meals and $^{13}CO_2$ breath enrichment analyses were used to assess digestion and assimilation. After obtaining IRB approved and informed consent, eight subjects underwent paired $^{13}$C-starch breath testing (U.S. patent Pend. Ser. No. 15/083,048; PMID 27579322) using a standardized 45 gm 150 mg 13C-starch/240 mL tracer-labeled rice pudding meal with and without refined AMG supplementation (20K AGU per 2 capsules), respectively on separate days. Changes in isotopic enrichments were measured and compared to the non-supplemented tests. Subjects included three young women with compound heterozygosity for congenital sucrase-isomaltase deficiency (CSID: 3p25.2-26) with near zero mucosal SI disaccharidase activity, one heterozygous man with CSID and diminished SI activity, one symptomatic man with IBD, one symptomatic woman with mixed IBS, and two healthy women (asymptomatic controls) that tolerated all high-starch content meals without symptoms.

Figure 15:
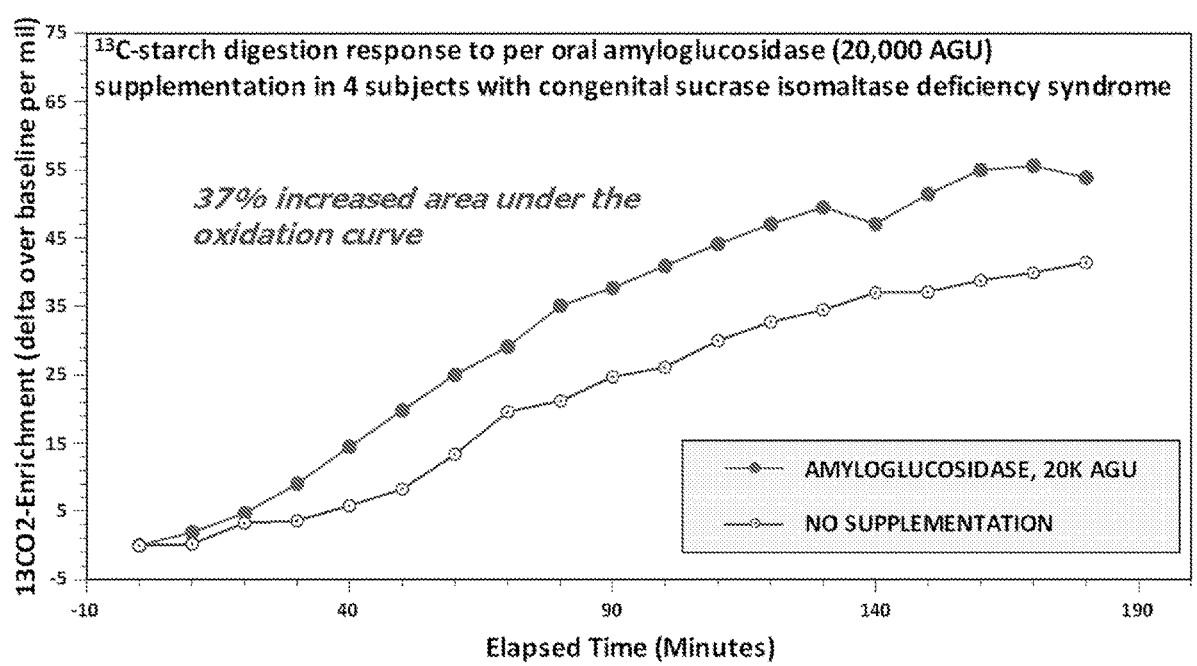
FIG. 15: 3-hour $^{13}$C-starch tracer labeled rice pudding breath test response to amyloglucosidase meal supplementation (20K AGU) in 4 symptomatic subjects with congenital sucrase-isomaltase deficiency syndrome (3p25.2-26). Each data point was adjusted for inherent CO2 production rate using Scofield equations.

RESULTS: supplemental AMG resulted in increased starch digestion in those with CSID, IBS, and IBD. Comparing area of enrichment under the 180 min timed curve, there was a 57% increase in digestive oxidation in the CSID patients ($^{13}CO_2$ Δ over the baseline enrichment ‰; FIG. 15), a 28% enrichment increase in the heterozygous CSID subject, and ~32% & ~6% enrichment increase in the two patients with IBD and IBS-M, respectively. The two healthy controls showed no improvement with AMG treatment over inherent digestive capacity (Table 3). There were no adverse events.

TABLE 3

All subject data for 3-hour $^{13}$C-starch tracer labeled (150 mg) rice pudding (45 gm load) breath test response to amyloglucosidase meal supplementation (20K AGU) in 8 subjects.

| Status | Compound Heterozyg. CSID 255 | Compound Heterozyg. CSID 156 | Compound Heterozyg. CSID 155 | Heterozyg. CSID 296 | IBS-Mix C3 | IBD-UC D4 | Healthy Control A1 | Healthy Control B2 |
|---|---|---|---|---|---|---|---|---|
| Gender-Aged (Years) | F (15) | F (17) | F (17) | M (18) | F (32) | M (28) | F (22) | F (25) |
| HEIGHT | 1.6 | 1.4 | 1.5 | 1.7 | 1.6 | 1.8 | 1.5 | 1.6 |
| Body Mass (KG) | 59.9 | 50.3 | 51.7 | 79.4 | 77.0 | 86.1 | 63.5 | 60.0 |
| CO2 Production Rate mM/min | 1.86 | 1.05 | 1.07 | 1.49 | 1.45 | 1.53 | 1.22 | 1.18 |
| Pre-treatment 3° AUC Enrichment | 427 | 379 | 344 | 520 | 647 | 499 | 853 | 826 |
| AMG On-treatment 3° AUC Enrichment | 731 | 650 | 439 | 666 | 685 | 659 | 782 | 776 |
| 3° delta enrichment with AMG treatment | +71.2% | +71.5% | +27.5% | +28.1% | +5.8% | +32.1% | (−9.1%) | (−13.7%) |

AMG supplementation (20K AGU) improved starch digestion as measured by $^{13}$C-tracer-labeled breath testing. AMG treatment approach may offer an effective therapy for CHO malabsorption in CSID, IBS, IBD, and iatrogenic mucositis. If true, AMG would be the first therapy proposed to address starch maldigestion in patients with CSID. Further testing is warranted to determine appropriate dosing to achieve maximum clinical benefit for the conditions cited above, to realize other applications and fully characterize the physiological effects.

Example 16

Amyloglucosidase Supplementation Corrects Small Intestinal Isomaltase Insufficiency in Symptomatic Patients with IBS and Congenital Sucrase-Isomaltase Deficiency (CSID)

Carbohydrate (CHO) maldigestion because of disaccharidase deficiency occurs with hypolactasia and primary or secondary sucrase-isomaltase (SI) deficiency. Cases of SI deficiency have been shown using stable isotope breath testing (BT), by genotyping and by Dahlqvist activity assays on performed on duodenal mucosal samples. When CHO load exceeds proximal digestive capacity, typical symptoms of abdominal discomfort, bloating and change in stool character ensue. Enzyme supplements are available for lactose and sucrose digestion, but not yet to complete starch digestion (~70% of the habitual diet). α-amylase is available for partial starch digestion to dextrins, but hydrolysis must be completed at the mucosal interface to permit glucose absorption. Oligosaccharides that pass to the colon are noxiously fermented. While dietary restriction appears to be helpful in relieving symptoms, it is difficult; and supplemental AMG improves proximal oligosaccharide digestion, in specific embodiments of the disclosure.

The present example characterizes whether oral AMG supplementation accelerates starch digestion. The inventor used stable isotope $^{13}$C-labeled starch load meals, $^{13}CO_2$ BT enrichment analyses and blood glucose (BG) monitoring to assess starch digestion and assimilation. After obtaining IRB approved consent, two subjects underwent paired $^{13}$C-starch BT (PMID 27579322) using a standardized $^{13}$C-labeled corn starch porridge with and without refined AMG supplementation (20K AGU per 2 large capsules or 4000 AGU per 4 small capsules) on separate test days. Changes in $^{13}CO_2$ BT enrichments and BG were measured and compared to the non-supplemented tests. Subjects included 2 women: one with compound heterozygosity for CSID (3p25.2-26) with near zero mucosal SI activity and one with marked mixed-IBS symptoms.

Figure 16:
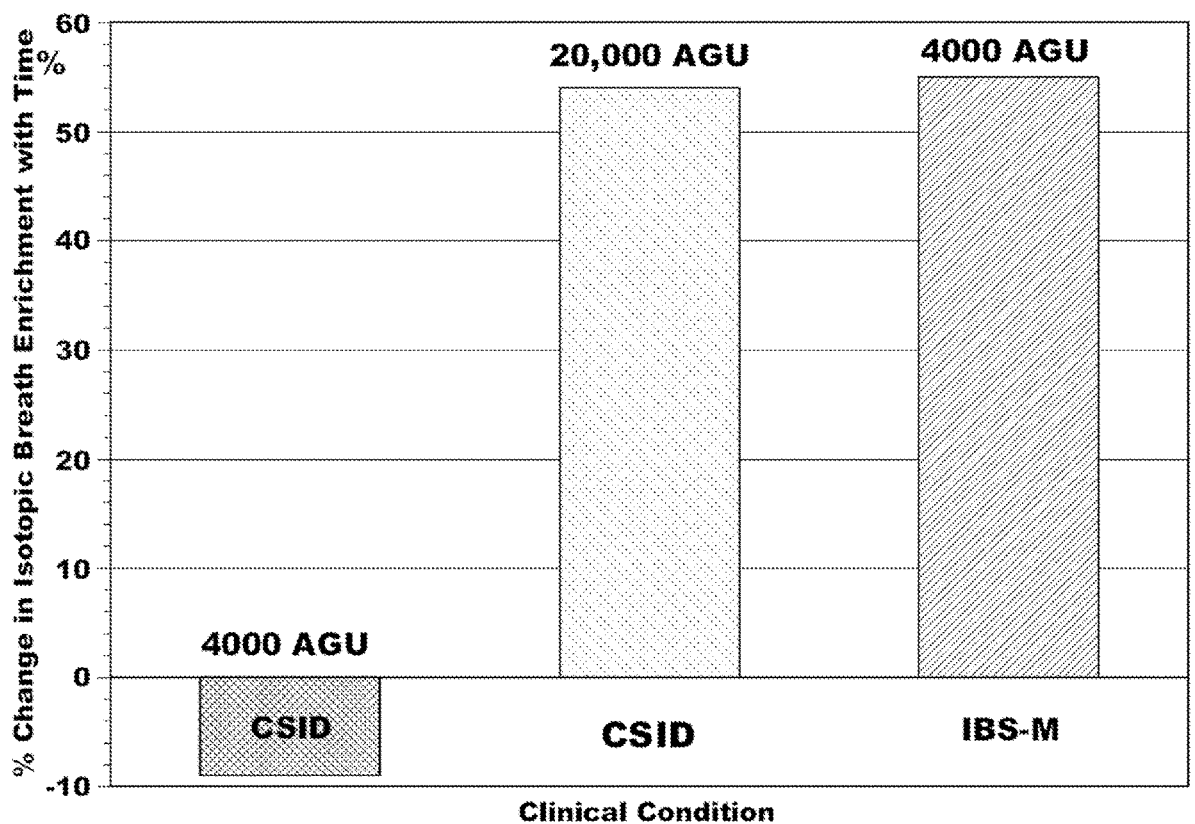
FIG. 16: The change (delta) in $^{13}$C-starch breath-test response from baseline, measured in humans at 120 minutes elapsed time, to one oral dosage of purified amyloglucosidase. Column left shows a robust response to 20,000 AGU amyloglucosidase in a patient with CSID, and indicates that a dose-response relationship exists, and column right shows a robust response to 20,000 AGU in a patient with mixed-form irritable bowel syndrome (IBS-M). The non-response (left column 4000 AGU) indicates that the response was too small to be detected or that the released glucose was assimilated into body stores and that there was no excessive glucose available for oxidation and breath test detection at 120 minutes ET.

Supplemental AMG increased starch digestion in those with CSID and IBS. Using 20K AGU dose, the area under the BT enrichment curve increased 54% (120 min) in the CSID patient ($^{13}CO_2$ Δ over the baseline; FIG. 16). Using the 4K AGU dose, the area under the enrichment curve increased 55% in the IBS patient and was slightly diminished in the CSID case. The column on the left shows a robust response to 20,000 AGU amyloglucosidase in a patient with CSID; the column in the center shows a no response to 4,000 AGU amyloglucosidase in a patient with CSID and indicates that a dose-response relationship exists, and the column on the right shows a robust response to 20,000 AGU in a patient with mixed-form irritable bowel syndrome (IBS-M). The non-response (center column 4000 AGU) indicates that the response was too small to be detected or that the released glucose was assimilated into body stores and that there was no excessive glucose available for oxidation and breath test detection at 120 minutes ET.

Figure 17:
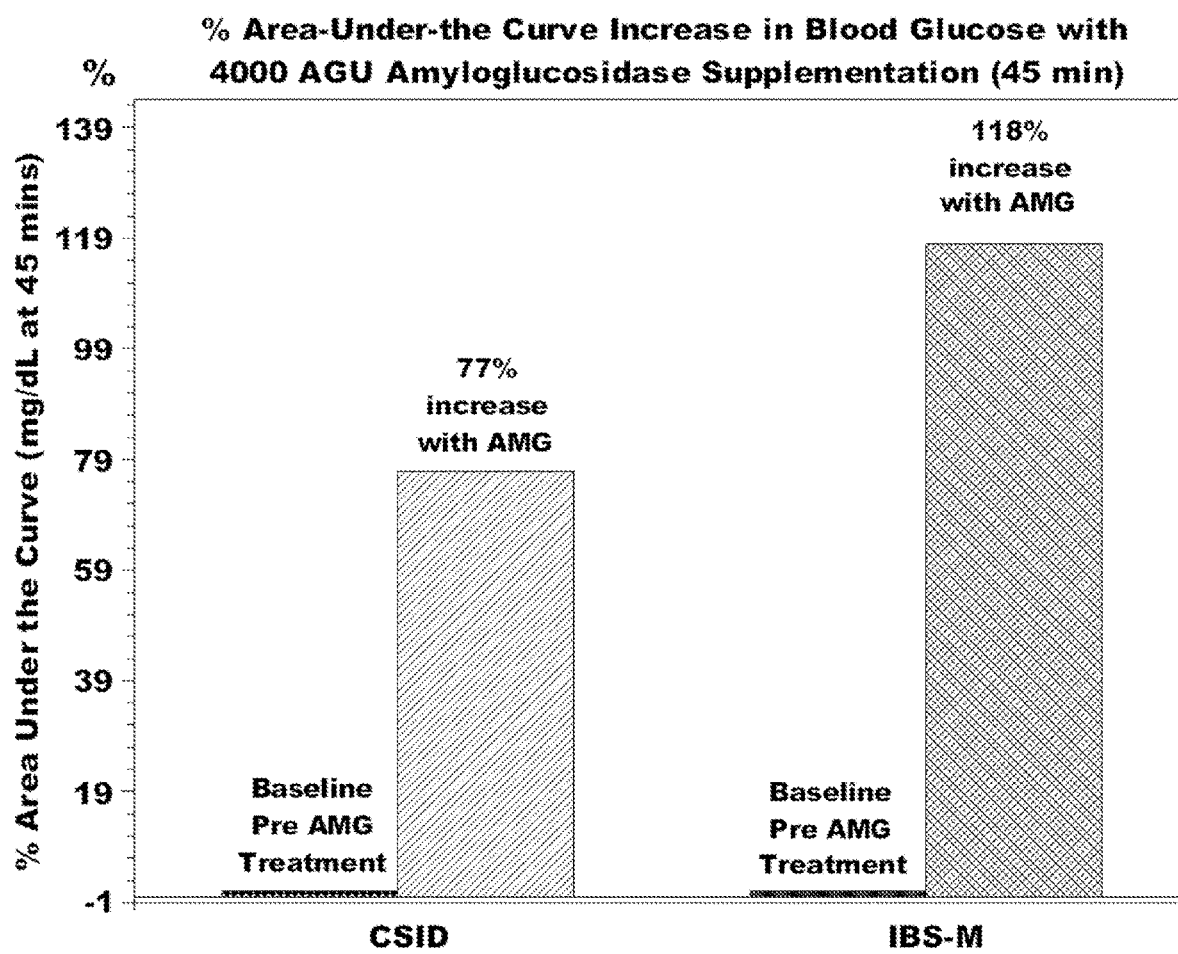
FIG. 17: The change (delta) in blood glucose concentration response from baseline, measured in humans at 45 minutes elapsed time, to one oral dosage of purified amyloglucosidase. Column-pair left shows a robust response to 4,000 AGU amyloglucosidase in a patient with CSID; and column-pair right shows a robust response to 4,000 AGU amyloglucosidase in a patient with mixed-form irritable bowel syndrome (IBS-M).

Blood glucose (FIG. 17) is presented as change (delta) in blood glucose concentration response from baseline, measured in humans at 45 minutes elapsed time, to one oral dosage of purified amyloglucosidase. There is a 118%-rise at 45 min (IBS) and 77% rise at 45 min (CSID). There were no adverse events. The column-pair on the left shows a robust response to 4,000 AGU amyloglucosidase in a patient with CSID; and the column-pair on the right shows a robust response to 4,000 AGU amyloglucosidase in a patient with mixed-form irritable bowel syndrome (IBS-M).

Thus, the 20K AGU AMG supplementation significantly improved starch digestion in the case of CSID as measured by $^{13}$C-tracer-labeled breath testing. The 4K AGU AMG supplementation improved starch digestion in the case of IBS as measured by rise breath enrichment and demonstrated a rise in blood glucose (both cases). In a particular embodiment, there is a dose-response relationship, and dosing may in at least some cases depend upon meal load and habitus. AMG treatment approach offers an effective therapy for CHO malabsorption at least in CSID IBS and other environmental enteropathy. AMG is the first therapy to address starch maldigestion in these patients.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Abarca M L, Bragulat M R, Castellá G, Cabañes F J. Ochratoxin A production by strains of *Aspergillus niger* var. *niger*. Appl Environ Microbiol. 1994; 60(7):2650-2.

Ambrus A, Füzesi I, Lantos J, Korsos I, Szathmáry M, Hatfaludi T. Application of TLC for confirmation and screening of pesticide residues in fruits, vegetables, and cereal grains: Part 2. Repeatability and reproducibility of Rf and MDQ values. J Environ Sci Health B. 2005; 40(4):485-511.

Amirul A A, Khoo S L, Nazalan M N, Razip M S, Azizan M N. Purification and properties of two forms of glucoamylase from *Aspergillus niger*. Folia Microbiol (Praha). 1996; 41(2):165-74

Andreyev J, Ross P, Donnellan C, et al. Guidance on the management of diarrhoea during cancer chemotherapy. Lancet Oncol. 2014; 15(10):e447-60.

Auricchio S, Dahlqvist A, Murset G, Parker A. Isomaltose intolerance causing decreased ability to utilize dietary starch. J Pediatr. 1963; 62:165-76.

Bennett J W, Klich M. Mycotoxins. Clin Microbiol Rev. 2003; 16(3):467-516.

Bompard-Gilles C, Rousseau P, Rougé P, Payan F. Substrate mimicry in the active center of a mammalian alpha-amylase: structural analysis of an enzyme-inhibitor complex. Structure. 1996; 4(12):1441-52.

Cambell G L and Bedford M R. Enzyme applications for monogastric feeds: a review. Can J Animal Sci. 1992; 72:449-466.

Cardani D, Sardi C, La Ferla B, et al. Sodium glucose cotransporter 1 ligand BLF501 as a novel tool for management of gastrointestinal mucositis. Molecular Cancer. 2014; 13:23.

Cass A E, Davis G, Francis G D, Hill H A, Aston W J, Higgins I J, Plotkin E V, Turner A P. Ferrocene-mediated enzyme electrode for amperometric determination of glucose. Anal Chem. 1984; 56:667-71.

Chen S, Xiong Y, Su L, Wang L, Wu J. Position 228 in *Paenibacillus macerans* cyclodextrin glycosyltransferase is critical for 2-O-D-glucopyranosyl-L-ascorbic acid synthesis. J Biotechnol. 2017; 247:18-24.

Cohen S A. The clinical consequences of sucrase-isomaltase deficiency. Mol Cell Pediatr 2016; 3:5.

Conklin K A, Yamashior K M, Gray G M. Human Intestinal-Isomaltase. J Biol Chem 1975; 250:5735-41.

Custodio H. Protozoan parasites. Pediatr Rev. 2016; 37:59-69 del Castillo Agudo L, Gozalbo D. Genes involved in the regulation of invertase production in *Saccharomyces cerevisiae*. Microbiologia. 1994; 10(4):385-94.

de Oliveira E P. Runner's diarrhea: what is it, what causes it, and how can it be prevented? Curr Opin Gastroenterol. 2017 January; 33(1):41-46.

Deng Y, Misselwitz B, Dai N, Fox M Lactose Intolerance in Adults: Biological Mechanism and Dietary Management. Nutrients 2015; 7(9):8020-35

Diaz-Sotomayor M, Quezada-Calvillo R, Avery S E, Chacko S K, Yan L K, Lin A H, et al. Maltase-glucoamylase modulates gluconeogenesis and sucrase-isomaltase dominates starch digestion glucogenesis. J Pediatr Gastroenterol Nutr. 2013; 57:704-712.

Eppley R M, Trucksess M W, Nesheim S, Thorpe C W, Wood G E, Pohland A E. Deoxynivalenol in winter wheat: thin layer chromatographic method and survey. J Assoc Off Anal Chem. 1984; 67(1):43-5.

Fearon K, Strasser F, Anker S D et al. Definition and classification of cancer cachexia: an international consensus. Lancet Oncol. 2011; 12(5):489-95

Fernandez C1, Stack M E, Musser S M. Determination of deoxynivalenol in 1991 U.S. winter and spring wheat by high-performance thin-layer chromatography. J AOAC Int. 1994; 77(3):628-30.

Galand G. Brush border membrane sucrase-isomaltase, maltase-glucoamylase and trehalase in mammals. Comparative development, effects of glucocorticoids, molecular mechanisms, an dphylogenetic implications. Com Biochem PHysiol B. 1989; 94(1):1-11.

Geng L, Li D Y, Ou W, Yang Q, Fang T, Chen P, Yang M, Gong S. Congenital sucrase-isomaltase deficiency: an under-diagnosed disease in Chinese children. BMC Pediatr. 2014; 14:11.

Gericke B, Amiri M, Naim H Y. The multiple roles of sucrase-isomaltase in the intestinal physiology. Mol Cell Pediatr. 2016; 3(1):2.

Goliński P, Grabarkiewicz-Szczesna J. Chemical confirmatory tests for ochratoxin A, citrinin, penicillic acid, sterigmatocystin, and zearalenone performed directly on thin layer chromatographic plates. J Assoc Off Anal Chem. 1984; 67:1108-10.

Gonçalvez AA1, Badiale-Furlong E, de Souza-Soares L A, Siervs S T. Enzymatic determination of soluble and insoluble dietary fiber in rice and wheat bran. Arch Latinoam Nutr. 1998; 48(4):334-8.

Guzmán-Maldonado H, Paredes-López O. Amylolytic enzymes and products derived from starch: a review. Crit Rev Food Sci Nutr. 1995; 35(5):373-403.

He C, Fan Y, Liu G, Zhang H. He C, Fan Y, Liu G, Zhang H. Isolation and identification of a strain of *Aspergillus tubingensis* with deoxynivalenol biotransformation capability. Int J Mol Sci. 2008; 9:2366-75.

Hlavsa M C, Roellig D M, Seabolt M H, et al. Using Molecular Characterization to Support Investigations of Aquatic Facility-Associated Outbreaks of Cryptosporidiosis—Alabama, Arizona, and Ohio, 2016. MMWR Morb Mortal Wkly Rep. 2017; 66:493-497.

Honda M, Miura A, Izumi Y, Kato T, Ryotokuji T, Monma K, Fujiwara J, Egashira H, Nemoto T. Doxorubicin, cisplatin, and fluorouracil combination therapy for metastatic esophageal squamous cell carcinoma. Dis Esophagus. 2010; 23(8):641-5

Jacob R, Zimmer K P Schmitz J, Naim H Y. Congenital sucrase-isomaltase deficiency arising from cleavage and secretion of a mutant form of the enzyme. J Clin Invest. 2000; 106(2): 281-7.

Karani S, Kataria M S, Barber A E. A double-blind clinical trial with a digestive enzyme product. Br J Clin Pract. 1971; 25(8):375-7.

Kasperowicz A, Stan-Glasek K, Guczynska W, Pristas P, Javorsky P, Vandzurova A, Michalowski T. β-Fructofuranosidase and sucrose phosphorylase of rumen bacterium Pseudobutyrivibrio ruminis strain 3. World J Microbiol Biotechnol. 2012; 28(3):1271-9.

Keefe M D for the FDA Center for Food Safety and Applied Nutrition FDA Agency Response Letter GRAS Notice No. GRN 000657 regarding food and ingredients;

Keefe D M, Brealey J, Goland G J, Cummins A G. Chemotherapy for cancer causes apoptosis that precedes hypoplasia in crypts of the small intestine in humans. Gut. 2000; 47(5):632-7.

Klish W J, Udall J N, Calvin R T, Nichols B L. The effect of intestinal solute load on water secretion in infants with acquired monosaccharide intolerance. Pediatr Res. 1980 December; 14(12):1343-6.

Koch P. State of the art of trichothecenes analysis. Toxicol Lett. 2004; 153(1):109-12.

Kumar P, Satyanarayana T. Microbial glucoamylases: characteristics and applications. Crit Rev Biotechnol. 2009; 29(3):225-55.

Langman J M, Rowland R. Activity of duodenal disaccharidases in relation to normal and abnormal mucosal morphology. J Clin Pathol 1990; 43(7):537-40.

Latorre-García L, Adam A C, Manzanares P, Polaina J. Improving the amylolytic activity of *Saccharomyces* cerevisiae glucoamylase by the addition of a starch binding domain. J Biotechnol. 2005; 118(2):167-76.

Li M, Hanford M J, Kim J W, Peeples T L. Amyloglucosidase enzymatic reactivity inside lipid vesicles. J Biol Eng. 2007; 1:4.

Lin L, Zhang J, Wang P, Wang Y, Chen J. Thin-layer chromatography of mycotoxins and comparison with other chromatographic methods. J Chromatogr A. 1998; 815:3-20.

Lina B A, Bar A, Subchronic oral toxicity studies with alpha-cyclodextrin in rats. Regul Toxicol Pharmacol. 2004; 39 Suppl 1:S14-26.

Mahajan P B, Kolhekar S R, Borkar P S. Purification of amyloglucosidase. Anal Biochem. 1983; 133(2):482-5.

Malir F, Severa J, Roubal T, et al. The dialysis of Ochratoxin A (OTA). Mycotoxin Res. 2001; 17 Suppl 2:129-31.

Marteau P, Flourie B. Tolerance to low-digestible carbohydrates: symptomatology and methods. Br J Nutr. 2001; 85 Suppl 1:S17-21.

Mazumder P M, Sasmal D. Mycotoxins—limits and regulations. Anc Sci Life. 2001; 20(3):1-19.

Mehra R, Khambadkone S M, Jain M K, Ganapathy S. Jejunal disaccharidases in protein energy malnutrition and recovery. Indian Pediatr. 1994; 31(11):1351-5.

Milicevic D R, Skrinjar M, Baltic T Real and perceived risks for mycotoxin contamination in foods and feeds: challenges for food safety control. Toxins 2010; 2:572-592.

Mundt A J1, Rotmensch J, Waggoner S, Quiet C, Fleming G. Phase I trial of concomitant chemoradiotherapy for cervical cancer and other advanced pelvic malignancies. Gynecol Oncol. 1999; 72(1):45-50.

Natarajan S1, Sierks M R. Functional and structural roles of the highly conserved Trp120 loop region of glucoamylase from *Aspergillus awamori*. Biochemistry. 1996; 35(9): 3050-8.

Nichols B L, Avery S E, Quezada-Calvillo R, Kilani S B, Lin A H, Burrin D G, Hodges B E, Chacko S K, Opekun A R, Hindawy M E, Hamaker B R, Oda S I. Improved Starch Digestion of Sucrase-deficient Shrews Treated With Oral Glucoamylase Enzyme Supplements. J Pediatr Gastroenterol Nutr. 2017; 65(2):e35-e42.

Nielsen A, Needham B, Leach S T, Day A S, Jaffe A, Thomas T, Ooi C Y. Disrupted progression of the intestinal microbiota with age in children with cystic fibrosis. Scientific Reports (2016); 6:24857.

Nisha M1, Satyanarayana T. Characteristics, protein engineering and applications of microbial thermostable pullulanases and pullulan hydrolases. Appl Microbiol Biotechnol. 2016 May 3.

Opekun A R, Balesh A M, Hernandez K, Shelby H T, Graham D Y. Sucrase-insufficiency-related irritable bowel syndrome. Gastroenterol. 2014; 146(5-S220)

Opekun A R, Balesh A M, Shelby H T. Use of the Biphasic $_{13}$C-Sucrose/Glucose Breath Test to Assess Sucrose Maldigestion in Adults with Functional Bowel Disorders. Biomed Res Int. 2016; 2016:7952891.

Papageorgiou M, Wells L, Williams C; White K, De Santis B, Liu Y, Debegnach F, Miano B, Moretti G, Greetham S, Brera C, Atkin S L, Hardie L J, Sathyapalan T. Assessment of Urinary Deoxynivalenol Biomarkers in UK Children and Adolescents. Toxins (Basel). 2018 Jan. 23; 10(2).

Parra F, Herrero P, Moreno F, Gascon S. Secretion of intermediate molecular forms of invertase by *Saccharomyces carlsbergensis* G-517 treated with 2-deoxy-D-glucose. FEBS Lett. 1980 Sep. 8; 118(2):330-2.

Pestka J J, Smolinski A T. Deoxynivalenol: toxicology and potential effects on humans. J Toxicol Environ Health B Crit Rev. 2005; 8(1):39-69.

Petersen J M, Forsmark C E. Chronic pancreatitis and maldigestion. Semin Gastrointest Dis. 2002; 13:191-9.

Peterson D E, Bensadoun R J, Roila F and the ESMO Guidelines Working Group Management of oral and gastrointestinal mucositis: ESMO clinical and practical guidelines. Ann Oncol. 2011; 22(s6): vi78-84

Pieters M N, Freijer J, Baars B J, Fiolet D C, van Klaveren J, Slob W Risk assessment of deoxynivalenol in food: concentration limits, exposure and effects. Adv Exp Med Biol. 2002; 504:235-48.

Puntis J W, Zamvar V. Congenital sucrase-isomaltase deficiency: diagnostic challenges and response to enzyme replacement therapy. Arch Dis Child. 2015; 100(9):869-71.

Quirce S, Fernández-Nieto M, Bartolomé B, Bombín C, Cuevas M, Sastre J. Glucoamylase: another fungal enzyme associated with baker's asthma. Ann Allergy Asthma Immunol. 2002; 89(2):197-202.

Ravich W J, Bayless T M. Carbohydrate absorption and malabsorption. Clin Gastroenterol. 1983; 12(2): 335-56.

Rather M Y, Nordberg Karlsson E1, Adlercreutz P. Complexation of alkyl glycosides with α-cyclodextrin can have drastically different effects on their conversion by glycoside hydrolases. J Biotechnol. 2015; 200:52-8.

Reis T1, Khazzaka E2, Welzel G3, Wenz F4, Hofheinz R D5, Mai S. Acute small-bowel toxicity during neoadjuvant combined radiochemotherapy in locally advanced rectal cancer: determination of optimal dose-volume cut-off value predicting grade 2-3 diarrhoea. Radiat Oncol. 2015; 10: 30

Robyt J F, White B J. Standard solutions (Chapter 2.7) in Robyt J F, White B J, Robyt. Biochemical techniques: Theory and practice. United States: Waveland Press, Prospect Heights Ill.; 1987.

Robyt J F, White B J. Thin-layer chromatography (Chapter 4.5) in Robyt J F, White B J, Robyt. Biochemical techniques: Theory and practice. United States: Waveland Press, Prospect Heights Ill.; 1987.

Robyt J F, White B J. Gel electrophoresis (Chapter 5.2) in Robyt J F, White B J, Robyt. Biochemical techniques: Theory and practice. United States: Waveland Press, Prospect Heights Ill.; 1987.

Robyt J F, White B J. Quantitative determination of carbohydrates (Chapter 7.1) in Robyt J F, White B J, Robyt. Biochemical techniques: Theory and practice. United States: Waveland Press, Prospect Heights Ill.; 1987.

Robyt J F, White B J. Determination of enzyme activity (Chapter 9.5) in Robyt J F, White B J, Robyt. Biochemical techniques: Theory and practice. United States: Waveland Press, Prospect Heights Ill.; 1987.

Roh M S, Colangelo L H, O'Connell M J, et al. Preoperative Multimodality Therapy Improves Disease-Free Survival in Patients With Carcinoma of the Rectum: NSABP R-03. J Clin Oncol. 2009; 27(31): 5124-5130.

Saha P, Manoharan P, Arthur S, Sundaram S, Kekuda R, Sundaram U. Molecular mechanism of regulation of villus cell Na—K-ATPase in the chronically inflamed mammalian small intestine. Biochim Biophys Acta. 2015; 1848(2):702-11

Sander I, Raulf-Heimsoth M, Siethoff C, Lohaus C, Meyer H E, Baur X. Allergy to *Aspergillus*-derived enzymes in the baking industry: identification of beta-xylosidase from *Aspergillus niger* as a new allergen (Asp n 14). J Allergy Clin Immunol. 1998; 102(2):256-64

Sauer J, Sigurskjold B W, Christensen U, Frandsen T P, Mirgorodskaya E, Harrison M, Roepstorff P, Svensson B. Glucoamylase: structure/function relationships, and protein engineering. Biochim Biophys Acta. 2000; 1543(2): 275-293.

Schiller L R Antidiarrheal drug therapy Curr Gastroenterol Rep 2017: 19:18

Schuster E, Dunn-Coleman N, Frisvad J C, van Dijck P W. On the safety of *Aspergillus niger*—A review. Applied Microbiology and Biotechnology 2002; 59(4-5):426-35

Sinagra E, Pompei G, Tomasello G, et al. Inflammation in irritable bowel syndrome: Myth or new treatment target? World J Gastroenterol. 2016; 22:2242-55.

Singla R K, Singh R, Dubey A K. Important Aspects of Post-Prandial Antidiabetic Drug, Acarbose. Curr Top Med Chem. 2016; 16(23):2625-33

Stoll D, Schmidt-Heydt M, Geisen R. Differences in the regulation of ochratoxin A by the HOG pathway in *Penicillium* and *Aspergillus* in response to high osmolar environments. Toxins 2013; 5:1282-98.

Stringer A M, Gibson R J, Bowen J M, Logan R M, Yeoh A S, Keefe D M. Chemotherapy-induced mucositis: the role of gastrointestinal microflora and mucins in the luminal environment. J Support Oncol. 2007; 5:259-67.

Taylor C, Hodgson K, Sharpstone D, Sigthorsson G, Coutts M, Sherwood R, Menzies I, Gazzard B, Bjarnason I. The prevalence and severity of intestinal disaccharidase deficiency in human immunodeficiency virus-infected subjects. Scand J Gastroenterol. 2000; 35(6):599-606.

Teotia S, Lata R, Khare S K, Gupta M N. One-step purification of glucoamylase by affinity precipitation with alginate. J Mol Recognit 2001; 14(5):295-9.

Trenk H L, Chu F S. Improved detection of ochratoxin A on thin layer plates. J Assoc Off Anal Chem. 1971; 54:1307-9.

Wang-Gillam A, Abrams R A, Posner M C, Pisters P W, Picozzi V J. Supportive care considerations during concurrent chemoradiotherapy for pancreatic adenocarcinoma: lessons learned from clinical experience. Am J Clin Oncol. 2013; 36(6):637-43.

Wilson D M, Mubatanhema W, Jurjevic Z. Biology and ecology of mycotoxigenic *Aspergillus* species as related to economic and health concerns. Adv Exp Med Biol. 2002; 504:3-17.

Wittekind A, Walton J. Worldwide trends in dietary sugars intake. Nutr Res Rev. 2014; 27(2):330-45.

Wright, A M, Loo D, Hirayame B A. Biology of human sodium glucose transporters. Physiol. Rev. 2011; 91:733-94.

Yuan B, Wang S A, Li F L. Improved ethanol fermentation by heterologous endoinulinase and inherent invertase from inulin by *Saccharomyces cerevisiae*. Bioresour Technol. 2013; 139:402-5.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for optimizing starch or fructans digestion in an individual, comprising the step of providing to the individual an effective amount of an amyloglucosidase composition produced by the method of extracting a crude amylglucosidase composition in the presence of an immiscible solvent, and separating a purified amyloglucosidase composition from the immiscible solvent, wherein the composition comprises amyloglucosidase in a dose that is equal to or greater than 10,000 unit releases of one gram of glucose per hour (AGU).

2. The method of claim 1, wherein the individual is in need of treatment or prevention of a condition selected from the group consisting of congenital sucrase isomaltase syndrome, functional bowel disorders, functional bowel syndrome, functional duodenal disorders, small bowel bacterial overgrowth, radiochemotherapy-induced mucositis and short-gut syndrome.

3. The method of claim 1, wherein the providing step occurs daily, weekly, monthly, or yearly.

4. The method of claim 1, wherein the individual is malnourished.

5. The method of claim 1, wherein the individual is an infant, child, adolescent, teenager, or adult.

6. The method of claim 1, wherein the composition is formulated in a comestible or beverage.

7. The method of claim 6, wherein the composition is a food supplement.

8. The method of claim 1, wherein the composition is in the form of a solid, liquid, or gel.

9. The method of claim 1, wherein the composition is a capsule, tablet, pill, film, lozenge, powder, or combination thereof.

10. The method of claim 1, wherein the immiscible solvent is absolute ethanol, acetone, Dimethyl sulfoxide, methanol, or a combination thereof.

11. The method of claim 10, wherein the solvent from which the purified amyloglucosidase composition is separated comprises one or more toxins.

12. The method of claim 1, wherein the crude amylglucosidase composition is in the form of a solid.

13. The method of claim 1, further comprising repeating the extracting and separating steps one or more times.

14. The method of claim 1, further comprising dissolving the purified amyloglucosidase composition in water to form a solution, and filtering the solution.

* * * * *